(12) United States Patent
Nazare et al.

(10) Patent No.: US 7,317,027 B2
(45) Date of Patent: Jan. 8, 2008

(54) AZAINDOLE-DERIVATIVES AS FACTOR XA INHIBITORS

(75) Inventors: Marc Nazare, Idstein (DE); Volkmar Wehner, Sandberg (DE); David William Will, Kriftel (DE); Kurt Ritter, Frankfurt am Main (DE); Matthias Urmann, Eschborn (DE); Hans Matter, Langenselbold (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 371 days.

(21) Appl. No.: 10/849,089

(22) Filed: May 19, 2004

(65) Prior Publication Data

US 2005/0009828 A1 Jan. 13, 2005

Related U.S. Application Data

(60) Provisional application No. 60/507,141, filed on Sep. 30, 2003.

(30) Foreign Application Priority Data

May 19, 2003 (EP) ................... 03011304

(51) Int. Cl.
*A61K 31/44* (2006.01)
*C07D 401/00* (2006.01)

(52) U.S. Cl. ............... 514/339; 546/277.1; 546/277.4; 548/469

(58) Field of Classification Search ............ 546/277.1, 546/277.4; 514/339; 548/469
See application file for complete search history.

(56) References Cited

U.S. PATENT DOCUMENTS

| 6,140,351 | A | 10/2000 | Arnaiz et al. |
| 6,337,344 | B1 | 1/2002 | Defossa |
| 6,436,965 | B1 * | 8/2002 | Labelle et al. ............... 514/339 |
| 6,790,853 | B2 | 9/2004 | Jacobson et al. |
| 6,906,084 | B2 * | 6/2005 | Nazare et al. ............... 514/323 |
| 6,953,857 | B2 | 10/2005 | Nazaré et al. |
| 7,067,665 | B2 | 6/2006 | Nazaré et al. |
| 7,135,469 | B2 | 11/2006 | Pinto |
| 2004/0171604 | A1 | 9/2004 | Nazaré et al. |
| 2004/0204406 | A1 | 10/2004 | Nazaré et al. |
| 2004/0235824 | A1 | 11/2004 | Nazaré et al. |
| 2005/0009827 | A1 | 1/2005 | Nazaré et al. |
| 2005/0009829 | A1 | 1/2005 | Nazaré et al. |
| 2005/0033049 | A1 | 2/2005 | Nazaré et al. |
| 2005/0043302 | A1 | 2/2005 | Nazaré et al. |

FOREIGN PATENT DOCUMENTS

| EP | 0987274 | 3/2000 |
| JP | 2004203791 A | 7/2004 |
| JP | 2004210716 A | 7/2004 |
| WO | WO92/06711 | 4/1992 |
| WO | WO95/29189 | 11/1995 |
| WO | WO96/12800 | 5/1996 |
| WO | WO97/47651 | 12/1997 |
| WO | WO01/07436 | 2/2001 |
| WO | WO 01/19788 | 3/2001 |
| WO | WO 01/64639 | 9/2001 |
| WO | WO 02/00651 | 1/2002 |
| WO | WO 02/070523 | 9/2002 |

OTHER PUBLICATIONS

Wang et al., 2002, CAS:137169502.*
U.S. Appl. No. 09/794,214, filed Feb. 28, 2001, Zhu et al.
U.S. Appl. No. 10/326,005, filed Dec. 20, 2002, Castelhano et al.
U.S. Appl. No. 10/510,046, filed Oct. 01, 2004, Cezanne et al.
U.S. Appl. No. 10/301,397, filed Nov. 21, 2002, Nazaré.
Adang, Anton E. P. et al., A New Generation of Orally Active Antithrombotics: Comparing Strategies in the GPII/IIIa, Thrombin and Factor Xa Areas, Drugs of the Future, (2000), vol. 24, No. 4, pp. 369-383.
Ball, et al., The Mechanism of Lithiation and Nitrile Insertion Reactions of beta-methylazines: evidence from the structure of 3-C5H4NCH=C(Ph)N(H)C(Ph)=NLi PMDETA, J. Organomet. Chem.; 550; 1998; pp. 457-461.
Beswick, et al., The Synthesis of 4-Substituted Indoles via Arenetricarbonylchromium(0) Complexes, Tetrahedron; 44; 1988; pp. 7325-7334.

(Continued)

*Primary Examiner*—Rei-tsang Shiao
(74) *Attorney, Agent, or Firm*—Jiang Lin

(57) ABSTRACT

The present invention relates to compounds of the formula I wherein $R^0$, $R^1$, $R^2$, $R^3$, Q, V, G and M are as defined herein. The compounds of the formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formula I, their use, in particular as active ingredients in pharmaceuticals, and pharmaceutical preparations comprising them.

10 Claims, No Drawings

OTHER PUBLICATIONS

Bornstein Joseph et al., Facile Hydrolysis of the Trifluoromethyl Group in the Presence of Base. Some Trifluoromethylated Indoles, J. Amer. Chem. Society, vol. 79, 1957, pp. 1745-1748.

Brennan Mary R et al., The Preparation and Spectral Characterization of 2-Haloindoles, 3-Haloindoles, and 2,3-Dihaloindoles, Heterocycles, 1986, vol. 24, No. 10, pp. 2879-2885.

Buchwald, et al., A General And Efficient Copper Catalyst For The Amidation Of Aryl Halides And the N-Arylation of Nitrogen Heterocycles, J. Am. Chem. Soc. 2001, 123, 7727-7729.

Bundgaard, Hans, Novel Chemical Approaches in Prodrug Design, Drugs of the Future, (1991), vol. 16, No. 5, pp. 443-458.

Burton Harold et al., The Synthesis of 5- and 6-Benzyloxyindoles and Attempts to prepare 5- and 6-Hydroxyindoles therefrom, J. Chem. Society, 1937, pp. 1726-1728.

Caddick, et al., Microwave Assisted Organic Reactions, Tetrahedron; 51; 1995; pp. 10403-10432.

Chan, et al., New N- and O-Arylations With Phenylboronic Acids And Cupric Acetate, Tetrahedron Letters 39 (1998) 2933-2936.

Chen, Cheng-yi et al., Syntheses of Indoles via a Palladium-Catalyzed Annulation between Iodoanilines and Ketones, J. Org. Chem., 1997, vol. 62, pp. 2676-2677.

Cheng, et al, Relationship Between The Inhibition Constant (KI) And The Concentation Of Inhibitor Which Causes 50 Per Cent Inhibition (I50) Of An Enzymatic Reaction, Biochem. Pharmacol. (1973), 22, 3099-3108.

Chikvaidze J Sh et al, Indole Derivatives, Khim. Geterotsikl, Soedin, 1991, Bol. 11, pp. 1508-1511 (English Abstract attached; full text English translation will be provided when and if obtained.).

Clemo, et al., A Contribution to the Study of Nicotine and the Synthesis of 7-Azaindole and Derivatives, J. Chem. Soc.; 1945; pp. 603-607.

Collot, et al., Regiospecific Functionalization of Indole-2-Carboxylates and Diastereoselective Preparation of the Corresponding Indolines, Heterocycles; 51; 12; 1999; pp. 2823-2846.

Comins Daniel L et al., N-Methyl Lithiation of N-Methylindoles Directed by a-Amino Alkoxides, Tetrahedron Letters, 1989, vol. 30, No. 33, pp. 4337-4340.

Davis, Michael L. et al., Reactions of beta-(Lithiomethyl)azines with Nitriles as a Route to Pyrrolo-pyridines, -quinolines, -pyrazines, -quinoxalines and -pyrimidines, Tetrahedron, vol. 48, No. 5, pp. 939-952, 1992.

Desarbre Eric et al., Synthesis of 2-Substituted-1H-Pyrrolo[2,3-b]Pyridines: Preparation of 7-Azaolivacine Analogue and 7-Azaindolopyridopyrimidine Derivatives, Tetrehedron, 1997, vol. 53, No. 10, pp. 3637-3648.

Dormoy Jean-Robert et al., Elaboration d'une nouvelle voie d'accés aux 6H-pyrido[4,3:b]carbazoles et analogues: A. Synthése et étude des précurseurs, Tetrahedron, 1993, vol. 49, No. 14, pp. 2885-2914.

Estel, et al., Metalation/S RN 1 Coupling in Heterocyclic Synthesis. A Convient Methodology for Ring Functionalization., J. Org. Chem.; 53; 1988; pp. 2740-2744.

Ezquerra Jesús et al., Efficient Reagents for the Synthesis of 5-, 7-, and 5,7-Substituted Indoles Starting from Aromatic Amines; Scope and Limitations, J. Org. Chem., 1996, vol. 61, pp. 5804-5812.

Fleisher, David et al., Improved Oral Drug Delivery: Solubility Limitations Overcome by the Use of Prodrugs, Advanced Drug Delivery Reviews, (1996), vol. 19, pp. 115-130.

Gray Nancy M et al., Novel Indole-2-Carboxylates as Ligands for the Strychnine-Insensitive N-Methyl-D-aspartate-Linked Glycine Receptor, J. Med. Chem., 1991, vol. 34, pp. 1283-1292.

Hands, David et al., A Convenient Method for the Preparation of 5-, 6- and 7-Azaindoles and Their Derivatives, Synthesis, Jul. 1996, pp. 877-882.

Hartwig, John, Ubergangsmetall-Katalysierte Synthese Von Arylaminen Und Arylethem Aus Arylhalogeniden Und-Triflaten: Anwendungen Und Reaktionsmechanismus, Angew. Chem. 1998, 110, 2154-2177.

Hartwig, et al., Room-Temperature Palladium-Catalyzed Amination of Aryl Bromides And Chlorides And Extended Scope Of Aromatic C-N Bond Formation With a Commercial Ligand, J. Org. Chem. (1999) 64, 5575-5580.

Hasan Iltifat et al., Synthesis and Reactions of N-Protected 2-Lithiated Pyrroles and Indoles. The tert-Butoxycarbonyl Substituent as a Protecting Group, J. Org. Chem., 1981, vol. 46, pp. 157-164.

Hiremath Shivayogi P et al., Synthesis & Reaction of Indole-1,2-Dicarboxaldehydes with Hydrazine & Hydroxylamine, Indian J. of Chemistry, 1980, vol. 19B, pp. 770-774.

Hughes, David L., Progress in the Fischer Indole Reaction, A Review, Org. Prep.Proc Int.; 25; 1993; pp. 607-632.

Khanna Ish K et al., 1,2-Diarylimidazoles as Potent, Cyclooxygenase-2 Selective, and Orally Active Antiinflammatory Agents, J. Med. Chem., 1997, vol. 40, pp. 1634-1647.

Kline Toni, Preparation of 2-Iodotryptamine and 2-Iodo-5-methoxytryptamine, J. Heterocycl. Chem., 1985, vol. 22, pp. 505-509.

Krstenansky, et al., Recent Advances in Microwave-assisted Organic Synthesis, Current Opinion in Drug Discovery & Development; 3(4); 2000; pp. 454-461.

Kuneri, Masao, Indole-related Compounds, Chem Abst.; 1962, pp. 3441i-3442b.

Kwong, et al., Copper-Catalyzed Coupling Of Alkylamines And Aryl Iodides: An Efficient System Even In An Air Atmosphere, Organic Lett. 2002, 4 (4), 581-584.

Lam, et al., New Aryl/Heteroaryl C-N Bond Cross-coupling Reactions Via Arylboronic Acid/Cupric Acetate Arylation, Tetrahedron Letters 39 (1998) 2941-2944.

Larhed, et al., Microwave-assisted high-speed chemistry: a new technique in drug discovery, Drug Discovery Today; 8; 2001; pp. 406-416.

Larock, et al., Synthesis of Indoles via Palladium-Catalyzed Heteroannulation of Internal Alkynes, J. Am. Chem. Soc.; 113; 1991; pp. 6689-6690.

Lidstrom, et al., Microwave assisted organic synthesis—a review, Tetrahedron; 57; 2001; pp. 9225-9283.

Lindwall H G et al., Synthesis and Reactions of Indole Carboxylic Acids; Pyridindolones from Indole-2-Carboxyacetalylbenzylamides, J. Org. Chem., 1953, vol. 18, pp. 345-357.

Mahadevan, et al., Synthesis of Pyrrolopyridines (Azaindoles), J. Heterecycl. Chem.; 29; 1992; pp. 359-367.

Mann, et al., Palladium-Catalyzed C-N(sp2) Bond Formation: N-Arylation Of Aromatic And Unsaturated Nitrogen And The Reductive Elimination Chemistry Of Palladium Azolyl And Methyleneamido Complexes, J. Am. Chem. Soc. (1998), 120, 827-828.

Martin, par Christian et al., Reactions Selectives de L'O. Chlorobenzonitrile : SNAr, Tetrahedron Letters, vol. 30, No. 8, pp. 935-936, 1989.

Matter, Hans et al., Design and Quantitative Structure—Activity Relationship of 3-Amidinobenzyl-1H-indole-2-carboxamides as Potent, Nonchiral, and Selective Inhibitors of Blood Congestion Factor Xa, Journal of Medicinal Chemistry, (2002), vol. 45, pp. 2749-2769.

Mederski Werner W K R et al., N-Aryl Heterocycles via Coupling Reactions with Arylboronic Acids, Tetrahedron, 1999, vol. 55, pp. 12757-12770.

Merour, et al., Synthesis and Reactivity of 7-Azaindoles (1H-Pyrrolo[2,3-b]pyridine), Current Org. Chem.; 5; 2001; pp. 471-506.

Murakami Yasuoki et al., p-Toluenesulfonic Acid and Cation Exchange Resin in Aprotic Solvent: Valuable Catalysts for Fisher Indolization, Heterocycles, 1984, vol. 22, No. 5, pp. 1210-1216.

Nichols, et al., 1-(2,5-Dimethoxy-4-(Trifluoeomethyl) Phenyl)-2-Aminopropane: A Potent Serotonin 5-HT2A/2C Agonist, J. Med. Chem. 1994,37, 4336-4351.

Noland Wayland E et al., Ethyl Indole-2-Carboxylate, Org. Synth. Coll., 1973, vol. V., J. Wiley New York, pp. 567-571.

Okada Hiroshi et al., Synthesis and Antitumor Activities of Prodrugs of Benzoylphenylureas, Chemical Pharmaceutical Bulletin, (1994), vol. 32, No. 1, pp. 57-61.

Okuda, et al., The Synthesis of 5-Azaindole, J. Org Chem.; 24; 1959; pp. 1008-1011.

Old David W et al., Efficient Palladium-Catalyzed N-Arylation of Indoles, Organic Letters, 2000, vol. 2, No. 10, pp. 1403-1406.

Ostrem James A et al., Discovery of a Novel, Potent, and Specific Family of Factor Xa Inhibitors via Combinatorial Chemistry, Biochemistry, 1998, vol. 37, pp. 1053-1059.

Powers James C, Chloroindoles, J. Org. Chem., 1966, vol. 31, pp. 2627-2631.

Rodriguez Alan Louis et al., Vielseitige Indolsynthese durch eine Kalium-oder Caesiumbasen-vermittelte 5-endo-dig-Cyclisierung, Agnew. Chem., 2000, vol. 112, No. 14, pp. 2607-2609.

Roesch, et al., Synthesis of Isoindolo[2,1-a]indoles by the Palladium-Catalyzed Annulation of Internal Acetylenes, J. Org. Chem.; 66; 2001; pp. 412-420.

Sakamoto Takao et al., Palladium-Catalyzed Coupling Reaction of 3-Iodoindoles and 3-Iodobenzo[b]thiophene with Terminal Acetylenes, Chem. Pharm. Bull, 1988, vol. 36, No. 6, pp. 2248-2252.

Sakamoto, et al., Condensed Heteroaromatic Ring Systems. Synthesis of Indoles and Pyrrolopyridines from o-Nitroarylacetylenes, Chem. Pharm, Bull.; 34(6); 1986; pp. 2362-2368.

Sakamoto, et al., Palladium-Catalyzed Cyanation Of Aryl and Heteroaryl Iodides With Copper (I) Cyanide, J. Chem. Soc. Perkin Trans I, 1999, 2323-2326.

Salituro Francesco G et al., 3-(2-Carboxyindol-3-yl)propionic Acid Derivatives: Antagonists of the Strychnine-Insensitive Glycine Receptor Associated with the N-Methyl-D-aspartate Receptor Complex, J. Med. Chem., 1990, vol. 33, pp. 2944-2946.

Santangelo, et al, A Convenient Synthesis of 9-Hydroxy-3,4,5,6-Tetrahydro-1H-Azepino [5,4,3-cd] Indole from 7-Methoxyindole, Synth. Commun.; 23; 1993; pp. 2717-2725.

Sarges Reinhard et al., A Novel Class of "GABAergic" Agents: 1-Aryl-3-(aminoalkylidene)oxindoles, J. Med. Chem., 1989, vol. 32, pp. 437-444.

Segel Irwin H, Behavior and Analysis of Rapid Equilibrium and Steady-State Enzyme Systems, Enzyme Kinetics, 1975, John Wiley & Sons, New York, pp. 100-125.

Stabler S Russell et al., Preparation of N-Arylated Heterocycles by Nucleophilic Aromatic Substitution, Synthetic Communications, 1994, vol. 24(1), pp. 123-129.

Takeuchi, et al., 1,2-Distributed Indole, Azaindole and Benzimidazole Derivatives Possessing Amine Moiety: A Novel Series of Thrombin Inhibitors, Bioorg. Med. Chem. Lett.; 20; 2000; pp. 2347-2351.

Tani Masanobu et al., Regioselective Bromination of Methoxy Derivitives of Ethyl Indole-2-Carboxylate [Synthetic Studies of Indoles and Related Compounds. XXX], Heterocycles, 1992, vol. 34, No. 12, pp. 2349-2362.

Tokmakov Gennadii P et al., Rearrangement of 1-Arylindoles to 5H-Dibenz[b,f]azepines, Tetrahedron, 1995, vol. 51, No. 7, pp. 2091-2098.

Turner, James, Regiospecific Electrophilic Substitution of Aminopyridines: Ortho Lithiation of 2-, 3-, and 4-(Pivaloylamino)pyridines, J. Org. Chem.; 48; 1983; pp. 3401-3408.

Ujjainwalla Feroze et al., Synthesis of 5-, 6- and 7-Azaindoles via Palladium-Catalyzed Heteroannulation of Internal Alkynes, Tetrahedron Lett., 1998, vol. 39, pp. 5355-5358.

Umemoto, et al., Power And Structure-Variable Fluorinating Agents. The N-Fluoropyridium Salt System, J. Am. Chem. Soc. (1990), 112, 8563-8575.

Unangst Paul C et al., Synthesis of Novel 1-Phenyl-1H-indole-2-carboxylic Acids. I. Utilization of Ullman and Dieckmann Reactions for the Preparation of 3-Hydroxy, 3-Alkoxy, and 3-Alkyl Derivatives, J. Heterocyclic Chem., 1987, vol. 24, pp. 811-815.

Wagaw Seble et al., A Palladium-Catalyzed Method for the Preparation of Indoles via the Fischer Indole Synthesis, J. Am. Chem. Soc., 1999, vol. 121, No. 44, pp. 10251-10263.

Willette, R.E., Monoazaindoles: The Pyrrolopyridines, Advances in Heterocyclic Chemistry; 9; 1968; pp. 27-105.

Wolfe, et al., Simple, Efficient Catalyst System For The Palladium-Catalyzed Amination Of Aryl Chlorides, Bromides, and Triflates, J. Org. Chem. 2000, 65, 1158-1174.

Wolter, et al., Copper-Catalyzed Coupling of Aryl Iodides with Aliphatic Alcohols, Org. Letters; 4; 6; 2002; pp. 973-976.

Yang, et al., Palladium-Catalyzed Amination Of Aryl Halides And Sulfonates, J. Organomet. Chem. 1999, 576, 125.

U.S. Appl. No. 11/469,513, filed Sep. 01, 2006 Urmann et al.

U.S. Appl. No. 11/467,277, filed Aug. 25, 2006 Bauer et al.

* cited by examiner

AZAINDOLE-DERIVATIVES AS FACTOR XA INHIBITORS

This application claims the benefit of U.S. Provisional Application No. 60/507,141, filed Sep. 30, 2003.

FIELD OF THE INVENTION

The present invention relates to compounds of formula I,

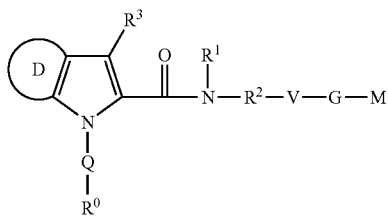

(I)

wherein $R^0$, $R^1$, $R^2$, $R^3$, Q, V, G and M have the meanings indicated below. The compounds of the formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formula I, their use, in particular as active ingredients in pharmaceuticals, and pharmaceutical preparations comprising them.

BACKGROUND OF THE INVENTION

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs (EP-A-987274). Many significant disease states are related to abnormal haemeostasis. For example, local thrombus formation due to rupture of atheroslerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. It is most desirable to develop agents that inhibit coagulation without directly inhibiting thrombin but by inhibiting other steps in the coagulation cascade like factor Xa and/or factor VIIa activity. It is now believed that inhibitors of factor Xa carry a lower bleeding risk than thrombin inhibitors (A. E. P. Adang & J. B. M. Rewinkel, Drugs of the Future 2000, 25, 369-383). Low molecular weight, factor Xa-specific blood clotting inhibitors that are effective but do not cause unwanted side effects have been described, for example, in WO-A-95/29189.

However, besides being an effective factor Xa-specific blood clotting inhibitor, it is desirable that such inhibitors also have further advantageous properties, for instance stability in plasma and liver and selectivity versus other serine proteases whose inhibition is not intended, such as thrombin. There is an ongoing need for further low molecular weight factor Xa specific blood clotting inhibitors, which are effective and have the above advantages as well.

Specific inhibition of the factor VIIa/tissue factor catalytic complex using monoclonal antibodies (WO-A-92/06711) or a protein such as chloromethyl ketone inactivated factor VIIa (WO-A-96/12800, WO-A-97/47651) is an extremely effective means of controlling thrombus formation caused by acute arterial injury or the thrombotic complications related to bacterial septicemia There is also experimental evidence suggesting that inhibition of factor VIIa/tissue factor activity inhibits restenosis following balloon angioplasty. Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition. Certain inhibitors of factor VIIa have already been described. EP-A-987274, for example discloses compounds containing a tripeptide unit, which inhibit factor VIIa. However, the property profile of these compounds is still not ideal, and there is an ongoing need for further low molecular weight factor VIIa inhibitory blood clotting inhibitors The present invention satisfies the above needs by providing novel compounds of the formula I, which exhibit better factor Xa and/or factor VIIa inhibitory activity and are favorable agents with high bioavailability.

SUMMARY OF THE INVENTION

The present invention relates to a compound of formula I,

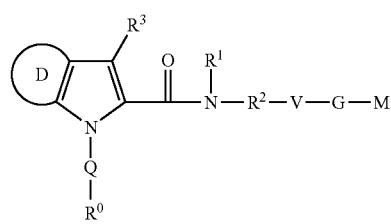

(I)

wherein
$R^0$ is
1) a monocyclic or bicyclic 6- to 14-membered aryl, wherein aryl is mono-, di- or trisubstituted independently of one another by R8,
2) a monocyclic or bicyclic 4- to 15-membered heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or
3) a monocyclic or bicyclic 4- to 15-membered heterocyclyl, containing one, two, three or four heteroatoms chosen from nitrogen, sulfur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulfur or oxygen, wherein heterocyclyl is unsubstituted or mono-, di- or trisubstituted independently of one another by R8, R8 is
1) halogen,
2) —$NO_2$,
3) —CN,
4) —C(O)—$NH_2$,
5) —OH,
6) —$NH_2$,
7) —O—$CF_3$
8) a monocyclic or bicyclic 6- to 14-membered aryl, wherein aryl is mono-, di- or trisubstituted independently of one another by halogen or —O—($C_1$-$C_8$)-alkyl,
9) —($C_1$-$C_8$)-alkyl, wherein alkyl is unsubstituted or mono-, di- or trisubstituted independently of one another by halogen, $NH_2$, —OH or a methoxy residue,
10) —O—($C_1$-$C_8$)-alkyl, wherein alkyl is unsubstituted or mono-, di- or trisubstituted independently of one another by halogen, $NH_2$, —OH or a methoxy residue,
11) —$SO_2$—$CH_3$ or
12) —$SO_2$—$CF_3$, provided that R8 is at least one halogen, —C(O)—$NH_2$ or —O—($C_1$-$C_8$)-alkyl residue, if $R^0$ is a monocyclic or bicyclic 6- to 14-membered aryl, the substructure

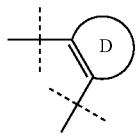

in formulae I is a 4-to 8 membered saturated, partially unsaturated or aromatic cyclic group containing zero, 1, 2, 3 or 4 heteroatoms chosen from nitrogen, sulfur or oxygen and is unsubstituted or substituted 1, 2, 3, 4, 5 or 6 times by R3, or substituted 1 or 2 times by=O, provided that said cyclic group is not a phenyl residue, Q is a direct bond, —($C_0$-$C_2$)-alkylene-C(O)—$NR^{10}$—, —$NR^{10}$—C(O)—$NR^{10}$—, —$NR^{10}$—C(O)—, —$SO_2$—, —($C_1$-$C_6$)-alkylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$-$C_3$)-alkylene-O—($C_0$-$C_3$)-alkylene-, —($C_2$-$C_3$)-alkylene-S(O)—, —($C_2$-$C_3$)-alkylene-S(O)$_2$—, —$(CH_2)_m$—$NR^{10}$—C(O)—O—$(CH_2)_n$—, —($C_2$-$C_3$)-alkylene-S(O)$_2$—NH—($R^{10}$)—, —($C_2$-$C_3$)-alkylene-N($R^{10}$)— or —($C_0$-$C_3$)-alkylene-C(O)—O—$(CH_2)_m$—,
wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or
—($C_3$-$C_6$)-cycloalkylen, wherein cycloalkylen is unsubstituted or mono-, di- or trisubstituted independently of one another by halogen, —$NH_2$ or —OH;

$R^1$ is a hydrogen atom, —($C_1$-$C_4$)-alkyl, wherein alkyl is unsubstituted or substituted one to three times by R13; —($C_1$-$C_3$)-alkylene-C(O)—NH—$R^0$, —($C_1$-$C_3$)-alkylene-C(O)—O—$R^{15}$, a monocyclic or bicyclic 6- to 14-membered aryl, wherein aryl is mono-, di- or trisubstituted independently of one another by R8, wherein R8 is as defined above; a monocyclic or bicyclic 4- to 15-membered heterocyclyl, containing one, two, three or four heteroatoms chosen from nitrogen, sulfur or oxygen; —($C_1$-$C_3$)-perfluoroalkylene, —($C_1$-$C_3$)-alkylene-S(O)—($C_1$-$C_4$)-alkyl, —($C_1$-$C_3$)-alkylene-S(O)$_2$—($C_1$-$C_3$)-alkyl, —($C_1$-$C_3$)-alkylene-S(O)$_2$—N($R^{4'}$)—$R^{5'}$, —($C_1$-$C_3$)-alkylene-O—($C_1$-$C_4$)-alkyl, —($C_0$-$C_3$)-alkylene-($C_3$-$C_8$)-cycloalkyl, or —($C_0$-$C_3$)-alkylene-het, wherein het is a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, $R^{4'}$ and $R^{5'}$ are independent of one another are identical or different and are hydrogen atom or —($C_1$-$C_4$)-alkyl, $R^2$ is a direct bond or —($C_1$-$C_4$)-alkylene, or $R^1$ and $R^3$ together with the atoms to which they are bonded can form a 6- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, or $R^1$—N—$R^2$—V can form a 4- to 7-membered cyclic group, containing 1, 2, 3 or 4 heteroatoms chosen from nitrogen, sulfur or oxygen, wherein said cyclic group is unsubstituted or mono-, di- or trisubstituted independently of one another by R14, R14 is halogen, —OH, =O, —($C_1$-$C_8$)-alkyl, —($C_1$-$C_4$)-alkoxy, —$NO_2$, —C(O)—OH, —CN, —$NH_2$, —C(O)—O—($C_1$-$C_4$)-alkyl, —($C_0$-$C_8$)-alkyl-$SO_2$—($C_1$-$C_4$)-alkyl, —($C_0$-$C_8$)-alkyl-$SO_2$—($C_1$-$C_3$)-perfluoroalkyl, —($C_0$-$C_8$)-alkyl-$SO_2$—N($R^{18}$)—$R^{21}$, —C(O)—NH—($C_1$-$C_8$)-alkyl, —C(O)—N—[($C_1$-$C_8$)-alkyl]$_2$, —$NR^{18}$—C(O)—NH—($C_1$-$C_8$)-alkyl, —C(O)—$NH_2$, —S—$R^{18}$, or —$NR^{18}$—C(O)—NH—[($C_1$-$C_8$)-alkyl]$_2$,
wherein $R^{18}$ and $R^{21}$ are independently from each other hydrogen atom, —($C_1$-$C_3$)-perfluoroalkyl or —($C_1$-$C_6$)-alkyl, V is 1) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14,
2) a 6- to 14-membered aryl, wherein aryl is unsubstituted or mono-, di- or trisubstituted independently of one another by R14, or
3) a monocyclic or bicyclic 4- to 15-membered heterocyclyl, wherein said heterocyclyl is unsubstituted or mono-, di- or trisubstituted independently of one another by R14, G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—$(CH_2)_n$—, —$(CH_2)_m$—C(O)—$NR^{10}$—$(CH_2)_n$—, —$(CH_2)_m$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C (O)—(CH₂)ₙ—, —(CH₂)ₘ—C(O)—(CH₂)ₙ—, —(CH₂)—S—(CH₂)ₙ—, —(CH₂)ₘ—SO₂—NR¹⁰—(CH₂)ₙ—, —(CH₂)ₘ—NR¹⁰—SO₂—(CH₂)ₙ—, —(CH₂)ₘ—NR¹⁰—, —(CH₂)ₘ—O—C(O)—NR¹⁰—(CH₂)ₙ— or —(CH₂)ₘ—NR¹⁰—C(O)—O—(CH₂)ₙ—, n and m are independently of one another identical or different and are the integers zero, 1, 2, 3, 4, 5 or 6, M is
1) a hydrogen atom,
2) —(C₁-C₈)-alkyl, wherein alkyl is unsubstituted or mono-, di- or trisubstituted independently of one another by R14,
3) —C(O)—N(R11)—R12,
4) —(CH₂)ₘ—NR¹⁰,
5) a 6- to 14-membered aryl, wherein aryl is unsubstituted or mono-, di- or trisubstituted independently of one another by R14,
6) a monocyclic or bicyclic 4- to 15-membered heterocyclyl, wherein heterocyclyl is unsubstituted or mono-, di- or trisubstituted independently of one another by R14,
7) —(C₃-C₈)-cycloalkyl, wherein said cycloalkyl is unsubstituted or mono-, di- or trisubstituted independently of one another by R14, or
8) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14, wherein R14 is defined above, R3 is
1) hydrogen atom,
2) halogen,
3) —(C₁-C₄)-alkyl, wherein alkyl is unsubstituted or mono-, di- or trisubstituted independently of one another by R13,
4) —(C₁-C₃)-perfluoroalkyl,
5) phenyl, wherein phenyl is unsubstituted or mono-, di- or trisubstituted independently of one another by R13,
6) —(C₀-C₄)-alkylene-O—R19, wherein R19 is
  a) hydrogen atom,
  b) —(C₁-C₄)-alkyl, wherein alkyl is unsubstituted or mono-, di- or trisubstituted independently of one another by R13,
  c) —CF₃, or
  d) —CHF₂,
7) —NO₂,
8) —CN,
9) —SOₛ—R¹¹, wherein s is 1 or 2,
10) —SOₜ—N(R¹¹)—R¹², wherein t is 1 or 2,
11) —(C₀-C₄)-alkylene-C(O)—R¹¹,
12) —(C₀-C₄)-alkylene-C(O)—O—R¹¹,
13) —(C₀-C₄)-alkylene-C(O)—N(R¹¹)—R¹²,
14) —(C₀-C₄)-alkylene-N(R¹¹)—R¹²,
15) —NR¹⁰—SO₂—R¹⁰,
16) —S—R¹⁰,
17) —(C₀-C₂)alkylene-C(O)—O—(C₂-C₄)-alkylene-O—C(O)—(C₁-C₄)-alkyl,
18) —C(O)—O—C(R15, R16)-O—C(O)—R17,
19) —(C₀-C₂)alkylene-C(O)—O—(C₂-C₄)-alkylene-O—C(O)—O—(C₁-C₆)-alkyl,
20) —C(O)—O—C(R15, R16)-O—C(O)—O—R17,
21) —(C₀-C₄)-alkylene-(C₆-C₁₄)-aryl, wherein aryl is mono-, di- or trisubstituted independently of one another by R13,
22) —(C₀-C₄)-alkylene-(C₄-C₁₅)-heterocyclyl, wherein heterocyclyl is unsubstituted or mono-, di- or trisubstituted independently of one another by R13
23) —(C₀-C₄)-alkylene-(C₃-C₈)-cycloalkyl, wherein cycloalkyl is unsubstituted or mono-, di- or trisubstituted independently of one another by R13,
24) —(C₀-C₄)-alkylene-het, wherein het is unsubstituted or mono-, di- or trisubstituted independently of one another by R13,
25) —(C₀-C₄)-alkylene-O—CH₂—(C₁-C₃)-perfluoro-alkylene-CH₂—O—(C₀-C₄)-alkyl,
26) —SOw—N(R¹¹)—R¹³, wherein w is 1 or 2,
27) —(C₀-C₄)-alkylene-C(O)—N(R¹¹)—R¹³,
28) —(C₀-C₄)-alkylene-N(R¹¹)—R¹³, or
29) a residue from the following list

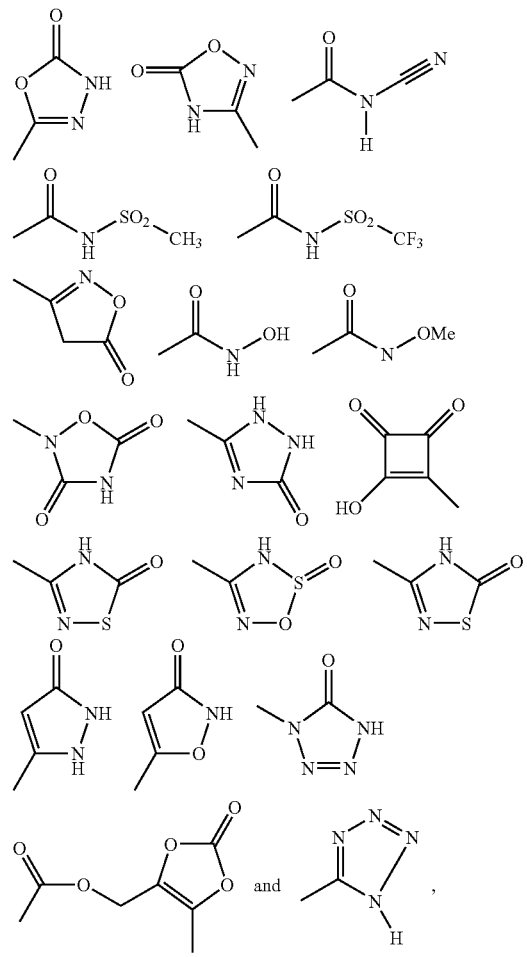

wherein Me is methyl, or
if two —OR19 residues are attached to adjacent atoms they can form together with the atoms which they are attached to a 5- or 6- membered ring, which is unsubstituted or substituted one, two, three or four times by R13, R11 and R12 are independently of one another identical or different and are
1) hydrogen atom,
2) —(C₁-C₆)-alkyl, wherein alkyl is unsubstituted or mono-, di- or trisubstituted independently of one another by R13,
3) —(C₀-C₆)-alkyl-(C₃-C₈)-cycloalkyl,
4) —SOₜ—R¹⁰, wherein t is 1 or 2, 5) —(C₀-C₆)-alkyl-(C₆-C₁₄)-aryl, wherein alkyl and aryl independently from one another are unsubstituted or mono-, di- or trisubstituted by R13,
6) —(C₁-C₃)-perfluoroalkyl,
7) —O—R¹⁷, or
8) —(C₀-C₆)-alkyl-(C₄-C₁₅)-heterocyclyl, wherein alkyl and heterocyclyl independently from one another are unsubstituted or mono-, di- or trisubstituted by R13, or R11 and R12 together with the nitrogen atom to which they are bonded can form a 4- to 7-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13, R13 is halogen, —NO₂, —CN, =O, —OH, —CF₃, —C(O)—O—R¹⁰, —C(O)—N(R¹⁰)—R²⁰, —N(R¹⁰)—R²⁰, —(C₃-C₈)-cycloalkyl, —(C₀-C₃)-alkylene-O—R¹⁰, —Si—(CH₃)₃, —N(R¹⁰)—S(O)ᵤ—R¹⁰, wherein u is 1 or 2, —S—R¹⁰, —SOᵣ—R¹⁰, wherein r is 1 or 2, —S(O)ᵥ—N(R¹⁰)—R²⁰, wherein v is 1 or 2, —C(O)—R¹⁰, —(C₁-C₈)-alkyl, —(C₁-C₈)-alkoxy, phenyl, phenyloxy-, —O—CF₃, —(C₀-C₄)-alkyl-C(O)—O—C(R15, R16)-O—C(O)—R17, —(C₁-C₄)-alkoxy-phenyl, —(C₀-C₄)-alkyl-C(O)—O—C(R15, R16)-O—C(O)—O—R17, —(C₁-C₃)-perfluoroalkyl, —O—R15, —NH—C(O)—NH—R¹⁰, —NH—C(O)—O—R¹⁰, or a residue from the following list

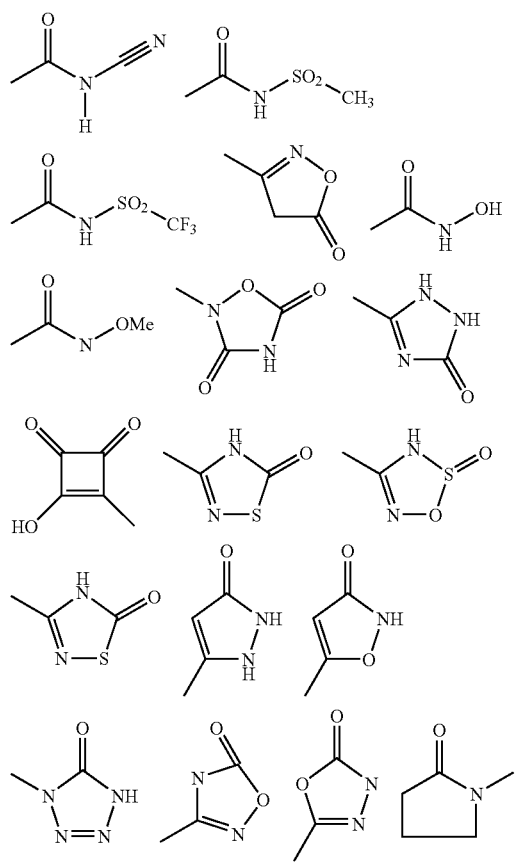

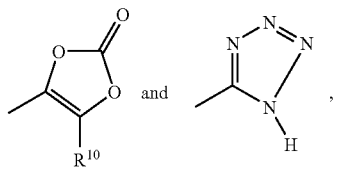

wherein Me is methyl,

R¹⁰ and R²⁰ are independently of one another hydrogen, —(C₁-C₆)-alkyl, —(C₀-C₄)-alkyl-OH, —(C₀-C₄)-alkyl-O—(C₁-C₄)-akyl or —(C₁-C₃)-perfluoroalkyl, R15 and R16 are independently of one another hydrogen, —(C₁-C₆)-alkyl, or together with the carbon atom to which they are bonded they can form a 3- to 6 membered carbocyclic ring which is unsubstituted or substituted one to three times by R¹⁰, and R17 is —(C₁-C₆)-alkyl, —(C₁-C₆)-alkyl-OH, —(C₁-C₆)-alkyl-O—(C₁-C₆)-alkyl, —(C₃-C₈)-cycloalkyl, —(C₁-C₆)-alkyl-O—(C₁-C₈)-alkyl-(C₃-C₈)-cycloalkyl, —(C₁-C₆)-alkyl-(C₃-C₈)-cycloalkyl, wherein said cycloalkyl ring is unsubstituted or substituted one, two or three times by —OH, —O—(C₁-C₄)-alkyl or R¹⁰, in all its stereoisomeric forms and mixtures thereof in any ratio, and its physiologically tolerable salts.

DETAILED DESCRIPTION OF THE INVENTION

Defintion of Terms

As used above, and throughout the description of the invention, the following terms, unless otherwise indicated, shall be understood to have the following meanings.

As used herein, the term alkyl is to be understood in the broadest sense to mean hydrocarbon residues which can be linear, i. e. straight-chain, or branched and which can be acyclic or cyclic residues or comprise any combination of acyclic and cyclic subunits. Further, the term alkyl as used herein expressly includes saturated groups as well as unsaturated groups which latter groups contain one or more, for example one, two or three, double bonds and/or triple bonds, provided that the double bonds are not located within a cyclic alkyl group in such a manner that an aromatic system results. All these statements also apply if an alkyl group occurs as a substituent on another residue, for example in an alkyloxy residue, an alkyloxycarbonyl residue or an arylalkyl residue. Examples of "—(C₁-C₈)-alkyl" or "—(C₁-C₈)-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. The term "—(C₀-C₆)-alkyl" or "—(C₀-C₈)-alkylene" is a hydrocarbon residue containing 1, 2, 3, 4, 5, 6, 7 or 8 carbon atoms. The term "—C₀-alkyl" or "—C₀-alkylene" is a covalent bond.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl. Alkyl residues can also be unsaturated when they are substituted.

Examples of —$(C_3-C_8)$-cycloalkyl cyclic alkyl residues are cycloalkyl residues containing 3, 4, 5, 6, 7 or 8 ring carbon atoms like cyclopropyl, cyclobutyl, cyclopentyl, cyclohexyl, cyloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom.

The terms "a monocyclic or bicyclic 6- to 14-membered aryl" or "—$(C_6-C_{14})$-aryl" are understood as meaning aromatic hydrocarbon radicals containing from 6 to 14 carbon atoms in the ring. Examples of —$(C_6-C_{14})$-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The terms "mono- or bicyclic 4- to 15-membered heterocyclyl" or "—$(C_4-C_{15})$-heterocyclyl" refer to heterocycles in which one or more of the 4 to 15 ring carbon atoms are replaced by heteroatoms such as nitrogen, oxygen or sulfur.

Examples are acridinyl, 8-aza-bicyclo[3.2.1]oct-3-yl, aza-indole (1H-pyrrolopyridinyl), azabenzimidazolyl, azapirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, 1λ6-thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

Preferred are heterocyclyls, such as benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl and 3-thienyl.

Also preferred are:

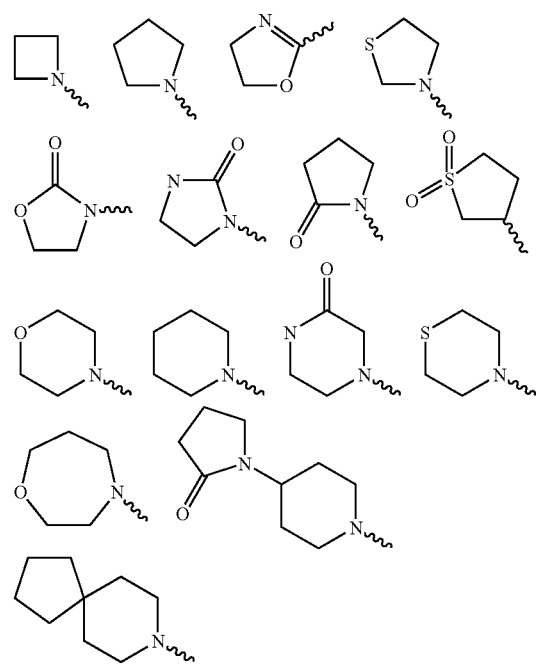

The terms "het" or "a 3- to 7-membered cyclic residue, containing up to 1, 2, 3 or 4 heteroatoms" refer to structures of heterocycles which can be derived from compounds such as azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "$R^1$—N—$R^2$—V can form a 4- to 7-membered cyclic group " or "$R^{11}$ and $R^{12}$ together with the nitrogen atom to which they are bonded can form a 4- to 7-membered monocyclic heterocyclic ring which in addition to the nitrogen atom can contain one or two identical or different ring heteroatoms chosen from oxygen, sulfur and nitrogen" refer to structures of heterocycles which can be derived from compounds such as azepane, azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole.

The term "$R^{15}$ and $R^{16}$ together with the carbon atom to which they are bonded can form a 3- to 6 membered carbocyclic ring" refer to structures, which can be derived from compounds such as cyclopropyl, cyclobutyl, cyclopentyl or cyclohexyl.

The term "substructure

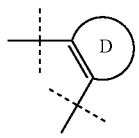

in formula I or the "substructure D" is a 4-to 8 membered saturated, partially unsaturated or aromatic cyclic group containing zero, 1, 2, 3 or 4 heteroatoms chosen from nitrogen, sulfur or oxygen" refer to structures, which can be derived from compounds such as azepane, azetidine, azetine, azocane, azocane-2-one, cyclobutyl, cyclooctane, cyclooctene, cyclopentyl, cyclohexyl, cycloheptyl, cyclooctyl, 1,2-diazepane, 1,2-diazepine, 1,3-diazepine, 1,4-diazepine, [1,4]diazocane, [1,2]diazocan-3-one, [1,3]diazocan-2-one, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxaazepane, 1,2-oxa-thiepane, 1,2-oxathiolan, 1,2-oxazine, 1,3-oxazine, 1,4-oxazine, oxazole, [1,4]oxazocane, [1,3]oxazocan-2-one, oxetan, oxocane, oxocan-2-one, piperazine, piperidine, phenyl, pyran, pyrazine, pyrazole, pyrazoline, pyrazolidine, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, thiadiazine thiadiazole, 1,2-thiazine, 1,3-thiazine, 1,4-thiazine, 1,3-thiazole, thiazole, thiazolidine, thiazoline, thietan, thiocane, thiocane-1,1-dioxide, thiocane-1-oxide, thiocan-2-one, thiomorpholine, thiopyran, 1,2,3-triazine, 1,2,4-triazine, 1,3,5-triazine, 1,2,3-triazole or 1,2,4-triazole. The term "substructure D" is a 5 to 6 membered saturated, partially unsaturated or aromatic cyclic group containing zero, 1, 2, 3 or 4 heteroatoms chosen from nitrogen, sulfur or oxygen" refer to structures, which can be derived from compounds such as cyclopentyl, cyclohexyl, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxathiolan, 1,2-oxazine, 1,3-oxazine, 1,4-oxazine, oxazole, piperazine, piperidine, phenyl, pyran, pyrazine, pyrazole, pyrazoline, pyrazolidine, pyrazine, pyrazinone, pyridazine, pyridazone, pyridine, pyridone, pyrimidine, pyrimidone, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thiomorpholine, thiopyran, tetrazine, tetrazole, 1,2,3-triazine, 1,2,4-triazine, 1,3,5-triazine, 1,2,3-triazole or 1,2,4-triazole.

The term "$R^1$ and $R^3$ together with the atoms to which they are bonded can form a 6- to 8-membered cyclic group, containing up to 1, 2, 3 or 4 heteroatoms chosen from nitrogen, sulfur or oxygen" refers to structures of heterocycles which can be derived from compounds such as azocane, azocane-2-one, cyloheptyl cyclohexyl, cyclooctane, cyclooctene, 1,4-diazepane, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxa-thiepane, 1,4-oxazepane, 1,2-oxazine, 1,3-oxazine, 1,4-oxazine, [1,4]oxazocane, [1,3]oxazocan-2-one, oxocane, oxocan-2-one, phenyl, piperazine, piperidine, pyran, pyrazine, pyridazine, pyrimidine, 5,6,7,8-tetrahydro-1H-azocin-2-one or thiomorpholine.

The fact that many of the before-listed names of heterocycles are the chemical names of unsaturated or aromatic ring systems does not imply that the, the 4-15 membered mono- or polycyclic group could only be derived from the respective unsaturated ring system. The names here only serve to describe the ring system with respect to ring size and the number of the heteroatoms and their relative positions. As explained above, the 4-15 membered mono- or polycyclic group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which this group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline or 1,2,3,4-tetrahydroisoquinoline.

The term "—$(C_1$-$C_3)$-perfluoroalkyl" is a partial or totally fluorinated alkyl-residue, which can be derived from residues such as —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "—$(C_1$-$C_3)$-perfluoroalkylene" is a partial or totally fluorinated alkylene-residue, which can be derived from residues such as —$CF_2$—, —$CHF$—, —$CHF$—$CHF_2$—, —$CHF$—$CHF$—, —$CH_2$—$CF_2$—, —$CH_2$—$CHF$—, —$CF_2$—$CF_2$—, —$CF_2$—$CHF$—, —$CH_2$—$CHF$—$CF_2$—, —$CH_2$—$CHF$—$CHF$—, —$CH_2$—$CH_2$—$CF_2$—, —$CH_2$—$CH_2$—$CHF$—, —$CH_2$—$CF_2$—$CF_2$—, —$CH_2$—$CF_2$—$CHF$—, —$CHF$—$CHF$—$CF_2$—, —$CHF$—$CHF$—$CHF$—, —$CHF$—$CH_2$—$CF_2$—, —$CHF$—$CH_2$—$CHF$—, —CHF—CF$_2$—CF$_2$—, —CHF—CF$_2$—CHF—, —CF$_2$—CHF—CF$_2$—, —CF$_2$—CHF—CHF—, —CF$_2$—CH$_2$—CF$_2$—, —CF$_2$—CH$_2$—CHF—, —CF$_2$—CF$_2$—CF$_2$—, or —CF$_2$—CF$_2$—CHF—.

The term "oxo-residue" or "=O" refers to residues such as carbonyl (—C(O)—) or nitroso (—N=O).

Halogen is fluorine, chlorine, bromine or iodine, preferably fluorine, chlorine or bromine, particularly preferably chlorine or bromine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

Physiologically tolerable salts of the compounds of formula I are nontoxic salts that are physiologically acceptable, in particular pharmaceutically utilizable salts. Such salts of compounds of the formula I containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formula I, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I, which simultaneously contain a basic group and an acidic group, for example a guanidino group and a carboxyl group, can also be present as zwitterions (betaines) which are likewise included in the present invention.

Patient includes both human and other mammals.

Pharmaceutically effective amount means an amount of the compound according to the invention effective in producing the desired therapeutic effect.

PARTICULAR OR PREFERRED EMBODIMENTS

One particular embodiment of the present invention relates to compound of the formula I, wherein R$^0$ is
1) a monocyclic or bicyclic 6- to 14-membered aryl out of the group phenyl, naphthyl, biphenylyl, anthryl or fluorenyl, wherein aryl is mono-, di- or trisubstituted independently of one another by R8,
2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or
3) a heterocyclyl, wherein heterocyclyl is selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl,
  wherein said heterocyclyl is unsubstituted or mono-, di- or trisubstituted independently of one another by R8, and which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein heterocyclyl is unsubstituted or mono-, di- or trisubstituted independently of one another by R8, R8 is
1) halogen,
2) —NO$_2$,
3) —CN,
4) —C(O)—NH$_2$,
5) —OH,
6) —NH$_2$,
7) —O—CF$_3$,
8) a monocyclic or bicyclic 6- to 14-membered aryl, wherein aryl is as defined above and wherein aryl is mono-, di- or trisubstituted independently of one another by halogen or —O—(C$_1$-C$_8$)-alkyl,
9) —(C$_1$-C$_8$)-alkyl, wherein alkyl is unsubstituted or mono-, di- or trisubstituted independently of one another by halogen, NH$_2$, —OH or a methoxy residue, or
10) —O—(C$_1$-C$_8$)-alkyl, wherein alkyl is unsubstituted or mono-, di- or trisubstituted independently of one another by halogen, NH$_2$, —OH or a methoxy residue,
11) —SO$_2$—CH$_3$ or
12) —SO$_2$—CF$_3$, provided that R8 is at least one halogen, —C(O)—NH$_2$ or —O—(C$_1$-C$_8$)-alkyl residue, if R$^0$ is a monocyclic or bicyclic 6- to 14-membered aryl, wherein aryl is as defined above, substructure D is a residue selected out of the group azetidine, azetine, azocane, azocane-2-one, cyclobutyl, cyclooctane, cyclooctene, cyclopentyl, cyclohexyl, cycloheptyl, cyclooctyl, 1,4-diazepane, 1,2-diazepine, 1,3-diazepine, 1,4-diazepine, [1,4]diazocane, [1,2]diazocan-3-one, [1,3]diazocan-2-one, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolan, 1,2-oxazine, 1,3-oxazine, 1,4-oxazine, oxazole, [1,4]oxazocane, [1,3]oxazocan-2-one, oxetan, oxocane, oxocan-2-one, piperazine, piperidine, pyran, pyrazine, pyrazole, pyrazoline, pyrazolidine, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, thiadiazine, thiadiazole, 1,2-thiazine, 1,3-thiazine, 1,4-thiazine, 1,3-thiazole, thiazole, thiazolidine, thiazoline, thietan, thiocane, thiocane-1,1-dioxide, thiocane-1-oxide, thiocan-2-one, thiomorpholine, thiophene, thiopyran, 1,2,3-triazine, 1,2,4-triazine, 1,3,5-triazine, 1,2,3-triazole or 1,2,4-triazole and is unsubstituted or substituted 1, 2, 3, 4, 5 or 6 times by R3, or is substituted 1 or 2 times by =O, Q is a direct bond, —(C$_0$-C$_2$)-alkylene-C(O)—NR$^{10}$—, —NR$^{10}$—C(O)—NR$^{10}$—, —NR$^{10}$—C(O)—, —SO$_2$—, —(C$_1$-C$_6$)-alkylene, —(CH$_2$)$_m$—NR$^{10}$—C(O)—NR$^{10}$—(CH$_2$)$_n$—, —(CH$_2$)$_m$—NR$^{10}$—C(O)—(CH$_2$)$_n$—, —(CH$_2$)$_m$—S—(CH$_2$)$_n$—, —(CH$_2$)$_m$—C(O)—(CH$_2$)$_n$—, —(CH$_2$)$_m$—SO$_2$—NR$^{10}$—(CH$_2$)$_n$—, —(CH$_2$)$_m$—NR$^{10}$—SO$_2$—(CH$_2$)$_n$—, —(CH$_2$)$_m$—NR$^{10}$—SO$_2$—NR$^{10}$—(CH$_2$)$_n$—, —(CH$_2$)$_m$—CH(OH)—(CH$_2$)$_n$—, —(CH$_2$)$_m$—O—C(O)—NR$^{10}$—(CH$_2$)$_n$—, —(C$_2$-C$_3$)-alkylene-O—(C$_0$-C$_3$)-alkylene-, —(C$_2$-C$_3$)-alkylene-S(O)—, —(C$_2$-C$_3$)-alkylene-S(O)$_2$—, —(CH$_2$)$_m$—NR$^{10}$—C(O)—O—(CH$_2$)$_n$—, —(C$_2$-C$_3$)-alkylene-S(O)$_2$—NH—(R$^{10}$)—, —(C$_2$-C$_3$)-alkylene-N(R$^{10}$)— or —(C$_0$-C$_3$)-alkylene-C(O)—O—, wherein R$^{10}$ is as defined below, and wherein n and m are independently of one another identical or different and are the integers zero, 1, 2, 3, 4, 5 or 6, wherein the alkylene residues which are formed by —(CH$_2$)$_m$— or —(CH$_2$)$_n$— are unsubstituted or mono-, di- or trisubstituted independently of one another by halogen, —NH$_2$ or —OH; or —(C$_3$-C$_6$)-cycloalkylen, wherein cycloalkylen is unsubstituted or mono-, di- or trisubstituted independently of one another by halogen, —NH$_2$ or —OH;

R$^1$ is a hydrogen atom, —(C$_1$-C$_4$)-alkyl, wherein alkyl is unsubstituted or substituted one to three times by R13; —(C$_1$-C$_3$)-alkylene-C(O)—NH—R$^0$, —(C$_1$-C$_3$)-alkylene-C(O)—O—R15, an aryl out of the group phenyl, naphthyl, biphenylyl, anthryl or fluorenyl, wherein aryl is mono-, di- or trisubstituted independently of one another by R8, wherein R8 is as defined above; a monocyclic or bicyclic 4- to 15-membered heterocyclyl, which is as defined above; —(C$_1$-C$_3$)-perfluoroalkylene, —(C$_1$-C$_3$)-alkylene-S(O)—(C$_1$-C$_4$)-alkyl, —(C$_1$-C$_3$)-alkylene-S(O)$_2$—(C$_1$-C$_3$)-alkyl, —(C$_1$-C$_3$)-alkylene-S(O)$_2$—N(R$^{4'}$)—R$^{5'}$, —(C$_1$-C$_3$)-alkylene-O—(C$_1$-C$_4$)-alkyl, —(C$_0$-C$_3$)-alkylene-(C$_3$-C$_8$)-cycloalkyl, or —(C$_0$-C$_3$)-alkylene-het, wherein het is a residue selected out of the group azepine, azetidine, aziridine, azirine, 1,4-diazapane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, 1,2-oxa-thiepane, 1,2-oxathiolane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, $R^{4'}$ and $R^{5'}$ are independent of one another are identical or different and are hydrogen atom or —$(C_1$-$C_4)$-alkyl, $R^2$ is a direct bond or —$(C_1$-$C_4)$-alkylene, $R^1$ and R3 together with the atoms to which they are bonded can form a 6- to 8-membered cyclic residue selected out of the group azocane, azocane-2-one, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxazine, 1,3-oxazine, 1,4-oxazine, [oxocane, oxocan-2-one, piperazine, piperidine, pyran, pyrazine, pyridazine, pyrimidine or 5,6,7,8-tetrahydro-1H-azocin-2-one, wherein said cyclic group is unsubstituted or mono-, di- or trisubstituted independently of one another by R14, or $R^1$—N—$R^2$—V can form a 4- to 7-membered cyclic group selected out of the group azepine, azetidine, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is fluorine, chlorine, bromine, iodine, —OH, =O, —$(C_1$-$C_8)$-alkyl, —$(C_1$-$C_4)$-alkoxy, —$NO_2$, —C(O)—OH, —CN, —$NH_2$, —C(O)—O—$(C_1$-$C_4)$-alkyl, —$(C_0$-$C_8)$-alkyl-$SO_2$—$(C_1$-$C_4)$-alkyl, —$(C_0$-$C_8)$-alkyl-$SO_2$—$(C_1$-$C_3)$-perfluoroalkyl, —$(C_0$-$C_8)$-alkyl-$SO_2$—$N(R^{18})$—$R^{21}$, —C(O)—NH—$(C_1$-$C_8)$-alkyl, —C(O)—N—$[(C_1$-$C_8)$-alkyl$]_2$, —$NR^{18}$—C(O)—NH—$(C_1$-$C_8)$-alkyl, —C(O)—$NH_2$, —S—$R^{18}$, or —$NR^{18}$—C(O)—NH—$(C_1$-$C_8)$-alkyl$]_2$, wherein $R^{18}$ and $R^{21}$ are independently from each other hydrogen atom, —$(C_1$-$C_3)$-perfluoroalkyl or —$(C_1$-$C_6)$-alkyl, V is 1) a monocyclic or bicyclic 6- to 14-membered aryl out of the group phenyl, naphthyl, biphenylyl, anthryl or fluorenyl, wherein aryl is mono-, di- or trisubstituted independently of one another by R14, 2) a heterocyclyl out of the group acridinyl, 8-aza-bicyclo[3.2.1]oct-3-yl, azaindole (1H-pyrrolopyridine), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 1,4-diazepane, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, 1λ6-thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R14, G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_m$— or —$(CH_2)_m$—$NR^{10}$—C(O)—O—$(CH_2)_n$—, n and m are independently of one another identical or different and are the integers zero, 1, 2, 3, 4, 5 or 6, M is 1) a hydrogen atom, 2) —$(C_1$-$C_8)$-alkyl, wherein alkyl is unsubstituted or mono-, di- or trisubstituted independently of one another by R14,

3) —C(O)—N(R11)-R12,

4) —$(CH_2)_m$—$NR^{10}$,

5) —$(C_6$-$C_{14})$-aryl, wherein aryl is as defined above and wherein aryl is unsubstituted or mono-, di- or trisubstituted independently of one another by R14, 6) —$(C_4$-$C_{15})$-heterocyclyl, wherein heterocyclyl is as defined above and is unsubstituted or mono-, di- or trisubstituted independently of one another by R14, or 7) —(C$_3$-C$_8$)-cycloalkyl, wherein said cycloalkyl is unsubstituted or mono-, di- or trisubstituted independently of one another by R14, R3 is
1) hydrogen atom,
2) halogen,
3) —(C$_1$-C$_4$)-alkyl, wherein alkyl is unsubstituted or mono-, di- or trisubstituted independently of one another by R13,
4) —(C$_1$-C$_3$)-perfluoroalkyl,
5) phenyl, wherein phenyl is unsubstituted or mono-, di- or trisubstituted independently of one another by R13,
6) —(C$_0$-C$_4$)-alkylene-O—R19, wherein R19 is
   a) hydrogen atom,
   b) —(C$_1$-C$_4$)-alkyl, wherein alkyl is unsubstituted or mono-, di- or trisubstituted independently of one another by R13,
   c) —CF$_3$, or
   d) —CHF$_2$,
7) —NO$_2$,
8) —CN,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —NR$^{10}$—SO$_2$—R$^{10}$,
16) —S—R$^{10}$,
17) —(C$_0$-C$_2$)alkylene-C(O)—O—(C$_2$-C$_4$)-alkylene-O—C(O)—(C$_1$-C$_4$)-alkyl,
18) —C(O)—O—C(R15, R16)-O—C(O)—R17,
19) —(C$_0$-C$_2$)alkylene-C(O)—O—(C$_2$-C$_4$)-alkylene-O—C(O)—O—(C$_1$-C$_6$)-alkyl,
20) —C(O)—O—C(R15, R16)-O—C(O)—O—R17,
21) —(C$_0$-C$_4$)-alkylene-(C$_6$-C$_{14}$)-aryl, wherein aryl is mono-, di- or trisubstituted independently of one another by R13,
22) —(C$_0$-C$_4$)-alkylene-(C$_4$-C$_{15}$)-heterocyclyl, wherein heterocyclyl is unsubstituted or mono-, di- or trisubstituted independently of one another by R13
23) —(C$_0$-C$_4$)-alkylene-(C$_3$-C$_8$)-cycloalkyl, wherein cycloalkyl is unsubstituted or mono-, di- or tri substituted independently of one another by R13,
24) —(C$_0$-C$_4$)-alkylene-het, wherein het is unsubstituted or mono-, di- or trisubstituted independently of one another by R13,
25) —(C$_0$-C$_3$)-alkylene-O—CH$_2$—(C$_1$-C$_3$)-perfluoroalkylene-CH$_2$—O—(C$_0$-C$_3$)-alkyl,
26) —SO$_w$—N(R$^{11}$)—R$^{13}$, wherein w is 1 or 2,
27) —(C$_0$-C$_4$)-alkylene-C(O)—N(R$^{11}$)—R$^{13}$,
28) —(C$_0$-C$_4$)-alkylene-N(R$^{11}$)—R$^{13}$, or
29) a residue from the following list

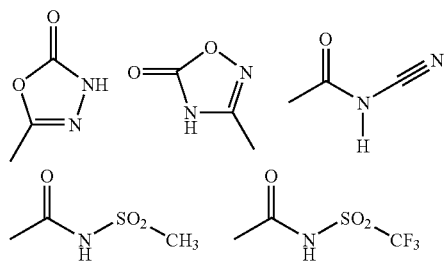

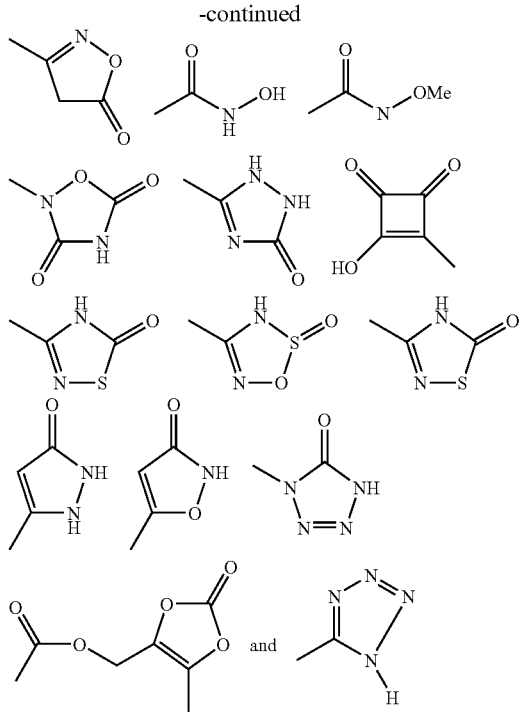

wherein Me is methyl, or if two —OR19 residues are attached to adjacent atoms they can form together with the atoms which they are attached to a 1,3-dioxole ring or a 2,3-dihydro-[1,4]dioxine ring, which is substituted one, two, three or four times by R13, R11 and R12 are independently of one another identical or different and are
1) hydrogen atom,
2) —(C$_1$-C$_6$)-alkyl, wherein alkyl is unsubstituted or mono-, di- or trisubstituted independently of one another by R13,
3) —(C$_0$-C$_6$)-alkyl-(C$_3$-C$_8$)-cycloalkyl,
4) —SO$_t$—R$^{10}$, wherein t is 1 or 2,
5) —(C$_0$-C$_6$)-alkyl-(C$_6$-C$_{14}$)-aryl, wherein alkyl and aryl independently from one another are unsubstituted or mono-, di- or trisubstituted by R13,
6) —(C$_1$-C$_3$)-perfluoroalkyl,
7) —O—R$^{17}$, or
8) —(C$_0$-C$_6$)-alkyl-(C$_4$-C$_{15}$)-heterocyclyl, wherein alkyl and heterocyclyl are as defined above and are independently from one another unsubstituted or mono-, di- or trisubstituted by R13, or R11 and R12 together with the nitrogen atom to which they are bonded form a heterocyclic ring out of the group azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R13, R13 is halogen, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_8$)-cycloalkyl, —(C$_0$-C$_3$)-alkylene-O—R$^{10}$, —Si—(CH$_3$)$_3$, —N(R$^{10}$)—S(O)$_u$—R$^{10}$, wherein u is 1 or 2, —S—R$^{10}$, —SO$_r$—R$^{10}$, wherein r is 1 or 2, —S(O)$_v$—N(R$^{10}$)—R$^{20}$, wherein v is 1 or 2, —C(O)—R$^{10}$, —(C$_1$-C$_8$)-alkyl, —(C$_1$-C$_8$)-alkoxy, phenyl, phenyloxy-, —O—CF$_3$, —(C$_0$-C$_4$)-alkyl-C(O)—O—C(R15, R16)-O—C(O)—R17, —(C$_1$-C$_4$)-alkoxy-phenyl, —(C$_0$-C$_4$)-alkyl-C(O)—O—C(R15, R16)-O—C(O)—O—R17, —(C$_1$-C$_3$)-perfluoroalkyl, —O—R15, —NH—C(O)—NH—R$^{10}$, —NH—C(O)—O—R$^{10}$, or a residue from the following list

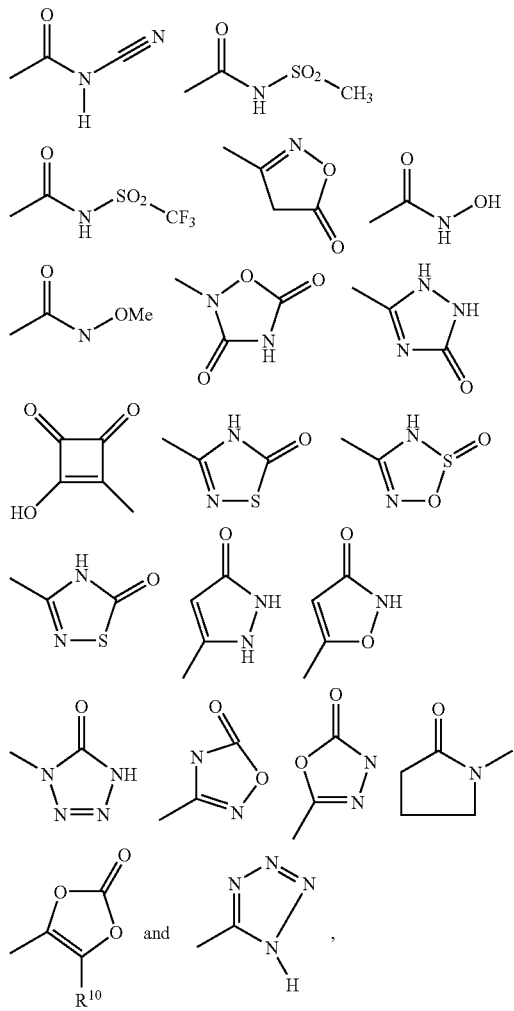

wherein Me is methyl,

R$^{10}$ and R$^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-akyl or —(C$_1$-C$_3$)-perfluoroalkyl, R15 and R16 are independently of one another hydrogen, —(C$_1$-C$_6$)-alkyl, cyclopropyl, cyclobutyl, cyclopentyl or cyclohexyl, wherein each ring is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts Another particular embodiment of the present invention relates to the compound of the formula I, wherein R$^0$ is 1) a monocyclic or bicyclic 6- to 14-membered aryl out of the group phenyl, naphthyl, biphenyl, anthryl or fluorenyl, wherein aryl is mono-, di- or trisubstituted independently of one another by R8, 2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or 3) a heterocyclyl out of the group azabenzimidazolyl, benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl or 3-thienyl, which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4- oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein heterocyclyl is unsubstituted or mono-, di- or trisubstituted independently of one another by R8, R8 is
1) fluorine, chlorine or bromine,
2) —$NO_2$,
3) —CN,
4) —C(O)—$NH_2$,
5) —OH,
6) —$NH_2$,
7) —$OCF_3$,
8) a monocyclic or bicyclic 6- to 14-membered aryl, wherein aryl is as defined above and is mono-, di- or trisubstituted independently of one another by halogen or —O—($C_1$-$C_8$)-alkyl,
9) —($C_1$-$C_8$)-alkyl, wherein alkyl is unsubstituted or mono-, di- or trisubstituted independently of one another by halogen, $NH_2$, —OH or a methoxy residue, or
10) —O—($C_1$-$C_8$)-alkyl, wherein alkyl is unsubstituted or mono-, di- or trisubstituted independently of one another by halogen, $NH_2$, —OH or a methoxy residue,
11) —$SO_2CH_3$ or
12) —$SO_2CF_3$, provided that R8 is at least one halogen, —C(O)—$NH_2$ or —O—($C_1$-$C_8$)-alkyl residue, if R0 is a aryl or a heterocyclyl, which are as defined above, substructure D is a residue selected out of the group pyridyl, pyridyl-N-oxide pyridyl, pyrrolyl, furyl, thienyl, imidazolyl, pyrazolyl, oxazolyl, isoxazolyl, thiazolyl, triazolyl, isothiazolyl, thiadiazolyl, pyrimidinyl, pyridazinyl, pyrazinyl and is unsubstituted or substituted 1, 2, 3 or 4 times by R3, or is substituted 1 or 2 times by =O, Q is a direct bond, —($C_0$-$C_2$)-alkylene-C(O)—$NR^{10}$—, —$NR^{10}$—C(O)—$NR^{10}$—, —$NR^{10}$—C(O)—, —$SO_2$—, or —($C_1$-$C_6$)-alkylene, $R^1$ is a hydrogen atom, —($C_1$-$C_4$)-alkyl, wherein alkyl is unsubstituted or substituted one to three times by R13; —($C_1$-$C_3$)-alkylene-C(O)—NH—$R^0$, —($C_1$-$C_3$)-alkylene-C(O)—O—R15, —($C_1$-$C_3$)-perfluoroalkylene, —($C_1$-$C_3$)-alkylene-S(O)—($C_1$-$C_4$)-alkyl, —($C_1$-$C_3$)-alkylene-S(O)$_2$—($C_1$-$C_3$)-alkyl, —($C_1$-$C_3$)-alkylene-S(O)$_2$—N($R^{4'}$)—$R^{5'}$, —($C_1$-$C_3$)-alkylene-O—($C_1$-$C_4$)-alkyl, —($C_0$-$C_3$)-alkylene-($C_3$-$C_8$)-cycloalkyl, or —($C_0$-$C_3$)-alkylene-het, wherein het is a residue selected out of the group azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, $R^{4'}$ and $R^{5'}$ are independent of one another are identical or different and are hydrogen atom or —($C_1$-$C_4$)-alkyl, $R^2$ is a direct bond or —($C_1$-$C_4$)-alkylene, or $R^1$—N—$R^2$—V form a 4- to 7-membered cyclic group selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is fluorine, chlorine, bromine, iodine, —OH, =O, —($C_1$-$C_8$)-alkyl, —($C_1$-$C_4$)-alkoxy, —$NO_2$, —C(O)—OH, —CN, —$NH_2$, —C(O)—O—($C_1$-$C_4$)-alkyl, —($C_0$-$C_8$)-alkyl-$SO_2$—($C_1$-$C_4$)-alkyl, —($C_0$-$C_8$)-alkyl-$SO_2$—($C_1$-$C_3$)-perfluoroalkyl, —($C_0$-$C_8$)-alkyl-$SO_2$—N($R^{18}$)—$R^{21}$, —C(O)—NH—($C_1$-$C_8$)-alkyl, —C(O)—N—[($C_1$-$C_8$)-alkyl]$_2$, —$NR^{18}$—C(O)—NH—($C_1$-$C_8$)-alkyl, —C(O)—$NH_2$, —S—$R^{18}$ or —$NR^{18}$—C(O)—NH—[($C_1$-$C_8$)-alkyl]$_2$, wherein $R^{18}$ and $R^{21}$ are independently from each other hydrogen atom, —($C_1$-$C_3$)-perfluoroalkyl or —($C_1$-$C_6$)-alkyl, V is
1) a het residue out of the group azaindole (1H-pyrrolopyridine), azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine, thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, which is as defined above and wherein het is unsubstituted or mono-, di- or trisubstituted independently of one another by R14, or
2) phenyl, wherein phenyl is unsubstituted or mono-, di- or trisubstituted independently of one another by R14, G is a direct bond, —($CH_2$)$_m$—$NR^{10}$—$SO_2$—$NR^{10}$—(C$H_2$)$_n$—, —($CH_2$)$_m$—CH(OH)—($CH_2$)$_n$—, —($CH_2$)$_m$—, —($CH_2$)$_m$—O—($CH_2$)$_n$—, —($CH_2$)$_m$—C(O)—$NR^{10}$—($CH_2$)$_n$—, —($CH_2$)$_m$—$SO_2$—($CH_2$)$_n$—, —($CH_2$)$_m$—$NR^{10}$—C(O)—$NR^{10}$—($CH_2$)$_n$—, —($CH_2$)$_m$—$NR^{10}$—C —(O)—(CH$_2$)$_n$—, —(CH$_2$)$_m$—C(O)—(CH$_2$)$_n$—, —(CH$_2$)—S—(CH$_2$)$_n$—, —(CH$_2$)$_m$—SO$_2$—NR$^{10}$—(CH$_2$)$_n$—, —(CH$_2$)$_m$—NR$^{10}$—SO$_2$—(CH$_2$)$_n$—, —(CH$_2$)$_m$—NR$^{10}$—, —(CH$_2$)$_m$—O—C(O)—NR$^{10}$—(CH$_2$)$_n$— or —(CH$_2$)$_m$—NR$^{10}$—C(O)—O—(CH$_2$)$_n$—, n and m are independently of one another identical or different and are the integers zero, 1, 2, 3, 4, 5 or 6, M is
1) a hydrogen atom,
2) —(C$_1$-C$_8$)-alkyl, wherein alkyl is unsubstituted or mono-, di- or trisubstituted independently of one another by R14,
3) —C(O)—N(R11)—R12,
4) —(CH$_2$)$_m$—NR$^{10}$,
5) phenyl or naphthyl, wherein phenyl or naphthyl are unsubstituted or mono-, di- or trisubstituted independently of one another by R14,
6) heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiophene, thiomorpholine, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14, or
7) —(C$_3$-C$_8$)-cycloalkyl, wherein said cycloalkyl is unsubstituted or mono-, di- or trisubstituted independently of one another by R14, R3 is
1) hydrogen atom,
2) halogen,
3) —(C$_1$-C$_4$)-alkyl, wherein alkyl is unsubstituted or mono-, di- or trisubstituted independently of one another by R13,
4) —(C$_1$-C$_3$)-perfluoroalkyl,
5) phenyl, wherein phenyl is unsubstituted or mono-, di- or trisubstituted independently of one another by R13,
6) —(C$_0$-C$_4$)-alkylene-O—R19, wherein R19 is
  a) hydrogen atom,
  b) —(C$_1$-C$_4$)-alkyl, wherein alkyl is unsubstituted or mono-, di- or trisubstituted independently of one another by R13,
  c) —CF$_3$, or
  d) CHF$_2$,
7) —CN,
8) —(C$_0$-C$_4$)-alkylene-(C$_4$-C$_{15}$)-heterocyclyl, wherein heterocyclyl is as defined above and is unsubstituted or mono-, di- or trisubstituted independently of one another by R13,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —NR$^{10}$—SO$_2$—R$^{10}$,
16) —(C$_0$-C$_4$)-alkylene-het, wherein het is as defined above and is unsubstituted or mono-, di- or trisubstituted independently of one another by R13,
17) —(C$_0$-C$_2$)alkylene-C(O)—O—(C$_2$-C$_4$)-alkylene-O—C(O)—(C$_1$-C$_4$)-alkyl,
18) —C(O)—O—C(R15, R16)-O—C(O)—R17,
19) —(C$_0$-C$_2$)alkylene-C(O)—O—(C$_2$-C$_4$)-alkylene-O—C(O)—O—(C$_1$-C$_6$)-alkyl,
20) —C(O)—O—C(R15, R16)-O—C(O)—O—R17,
21) —(C$_0$-C$_4$)-alkylene-(C$_6$-C$_{14}$)-aryl, wherein aryl is as defined above and is mono-, di- or trisubstituted independently of one another by R13,
22) —(C$_0$-C$_4$)-alkylene-(C$_3$-C$_8$)-cycloalkyl, wherein cycloalkyl is unsubstituted or mono-, di- or trisubstituted independently of one another by R13,
23) —(C$_0$-C$_3$)-alkylene-O—CH$_2$—CF$_2$—CH$_2$—O—(C$_0$-C$_3$)-alkyl,
24) —(C$_0$-C$_3$)-alkylene-O—CH$_2$—CF$_2$—CF$_2$—CH$_2$—O—(C$_0$-C$_3$)-alkyl,
25) —(C$_0$-C$_3$)-alkylene-O—CH$_2$—(C$_1$-C$_3$)-perfluoroalkylene-CH$_2$—OH,
26) —SO$_w$—N(R$^{11}$)—R$^{13}$, wherein w is 1 or 2,
27) —(C$_0$-C$_4$)-alkylene-C(O)—N(R$^{11}$)—R$^{13}$,
28) —(C$_0$-C$_4$)-alkylene-N(R$^{11}$)—R$^{13}$, or
29) a residue from the following list

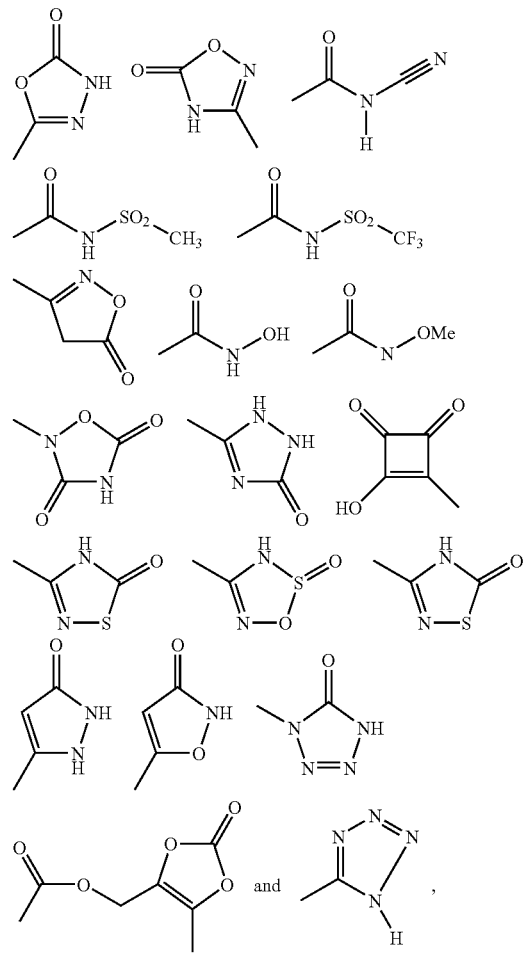

wherein Me is methyl,
if two —OR19 residues are attached to adjacent atoms they can form together with the atoms which they are attached to a 1,3-dioxole ring or a 2,3-dihydro-[1,4]dioxine ring, which is substituted one, two, three or four times by R13, R11 and R12 are independently of one another identical or different and are
1) hydrogen atom,
2) —(C$_1$-C$_6$)-alkyl, wherein alkyl is unsubstituted or mono-, di- or trisubstituted independently of one another by R13,
3) —(C$_0$-C$_6$)-alkyl-(C$_6$-C$_{14}$)-aryl, wherein aryl is as defined above and wherein alkyl and aryl are independently from one another unsubstituted or mono-, di- or trisubstituted by R13,
4) —O—R$^{17}$, or
5) —(C$_0$-C$_6$)-alkyl-(C$_4$-C$_{15}$)-heterocyclyl, wherein alkyl and heterocyclyl is as defined above and independently from one another are unsubstituted or mono-, di- or trisubstituted by R13, or R11 and R12 together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, which is unsubstituted or mono-, di- or trisubstituted independently of one another by R13, R13 is fluorine, chlorine, bromine, iodine, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_0$-C$_3$)-alkylene-O—R$^{10}$, —Si—(CH$_3$)$_3$, —N(R$^{10}$)—S(O)$_2$—R$^{10}$, —S—R$^{10}$, —SO$_2$—R$^{10}$, —S(O)$_2$—N(R$^{10}$)—R$^{20}$, —C(O)—R$^{10}$, —(C$_1$-C$_8$)-alkyl, —(C$_1$-C$_8$)-alkoxy, phenyl, phenyloxy-, —O—CF$_3$, —(C$_1$-C$_3$)-perfluoroalkyl, —(C$_0$-C$_4$)-alkyl-C(O)—O—C(R15, R16)-O—C(O)—R17, —(C$_1$-C$_4$)-alkoxy-phenyl, —(C$_0$-C$_4$)-alkyl-C(O)—O—C(R15, R16)-O—C(O)—O—R17, —O—R15, —NH—C(O)—NH—R$^{10}$, —NH—C(O)—O—R$^{10}$, or a residue from the following list

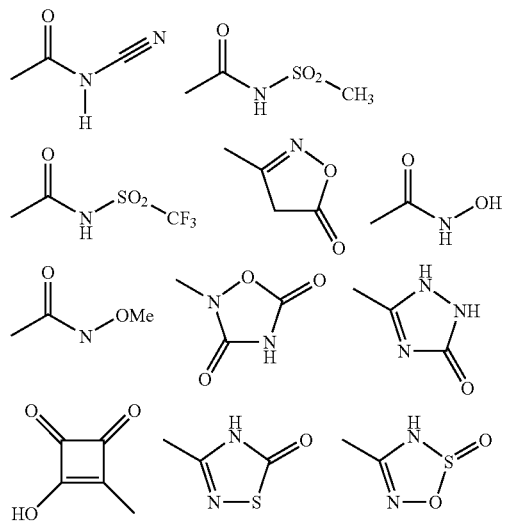

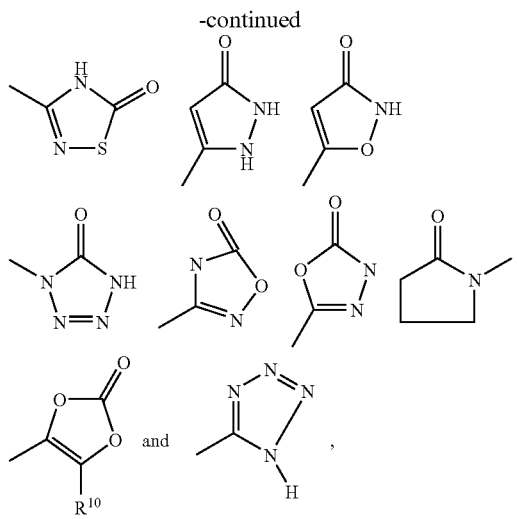

wherein Me is methyl,
R$^{10}$ and R$^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-akyl or —(C$_1$-C$_3$)-perfluoroalkyl,
R15 and R16 are independently of one another hydrogen, —(C$_1$-C$_6$)-alkyl, or together form a ring out of the droup cyclopropyl, cyclobutyl, cyclopentyl or cyclohexyl, wherein each ring is unsubstituted or substituted one to three times by R$^{10}$, and
R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

Another particular embodiment of the present invention relates to the compound of the formula I, wherein
R$^0$ is
1) phenyl, wherein phenyl is unsubstituted or mono-, di- or trisubstituted independently of one another by R8,
2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or
3) a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8, and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8

R8 is
1) F, Cl, Br or J,
2) —C(O)—NH$_2$,
3) —(C$_1$-C$_4$)-alkyl, wherein alkyl is unsubstituted or mono-, di- or trisubstituted independently of one another by halogen, —OH or a methoxy residue, or
4) —O—(C$_1$-C$_4$)-alkyl, wherein alkyl is unsubstituted or mono-, di- or trisubstituted independently of one another by halogen or a methoxy residue,
provided that R8 is at least one halogen, —C(O)—NH$_2$ or —O—(C$_1$-C$_8$)-alkyl residue, if R0 is a aryl or a heterocyclyl, which are as defined above, substructure D is a residue selected out of the group pyridyl, pyridyl-N-oxide, pyrrolyl, furyl, thienyl, imidazolyl, pyrazolyl, oxazolyl, isoxazolyl, thiazolyl, triazolyl, isothiazolyl, thiadiazolyl, pyrimidinyl, pyridazinyl, pyrazinyl and is unsubstituted or substituted 1, 2, 3 or 4 times by R3, or is substituted 1 or 2 times by =O, Q is a direct bond, —C(O)—; —SO$_2$—, —(C$_1$-C$_6$)-alkylene, or —(C$_0$-C$_2$)-alkylene-C(O)—NR$^{10}$—, R$^1$ is hydrogen atom, —(C$_1$-C$_2$)-alkyl, —(C$_1$-C$_3$)-alkylene-C(O)—NH—R0, —(C$_1$-C$_3$)-perfluoroalkylene, —(C$_1$-C$_3$)-alkylene-C(O)—O—R$^{15}$, —(C$_1$-C$_3$)-alkylene-S(O)$_2$—(C$_1$-C$_3$)-alkyl or —(C$_1$-C$_3$)-alkylene-S(O)$_2$—N(R$^{4'}$)—R$^{5'}$, wherein R$^{4'}$ and R$^{5'}$ are independent of one another are identical or different and are hydrogen atom or —(C$_1$-C$_4$)-alkyl, R$^2$ is a direct bond or —(C$_1$-C$_2$)-alkylene, R$^1$—N—R$^2$—V can form a 4- to 7- membered cyclic group out of the group azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazepane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14, R14 is fluorine, chlorine, —OH, =O, —(C$_1$-C$_8$)-alkyl, —C(O)—OH, —CN, —NH$_2$, —C(O)—O—(C$_1$-C$_4$)-alkyl, —C(O)—NH—(C$_1$-C$_8$)-alkyl, —C(O)—N—[(C$_1$-C$_8$)-alkyl]$_2$, —C(O)—NH$_2$ or —N(R$^{18}$)—R$^{21}$, wherein R$^{18}$ and R$^{21}$ are independently from each other hydrogen atom, —(C$_1$-C$_3$)-perfluoroalkyl or —(C$_1$-C$_4$)-alkyl, V is 1) a cyclic residue out of the group containing compounds which are derived from azaindole (1H-pyrrolopyridine), aziridine, azirine, azetidine, azetidinone, 1,4-diazepane, pyrrole, pyrrolidine, pyridonyl, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, tetrazole, azepine, diazirine, 1,2-diazepine, 1,3-diazepine, 1,4-diazepine, pyridazine, piperidine, piperazine, pyrrolidinone, ketopiperazine, furan, pyran, dioxole, 1,4-oxazepane, oxazole, isoxazole, 2-isoxazoline, isoxazolidine, morpholine, oxirane, oxaziridine, 1,3-dioxolene, 1,3-dioxolane, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiodiazole, thiopyran, 1,2-thiazine, 1,3-thiazole, 1,3-thiazine, 1,4-thiazine, thiadiazine or thiomorpholine, wherein said cyclic residue is unsubstituted or mono-, di- or trisubstituted independently of one another by R14, or 2) phenyl, wherein phenyl is unsubstituted or mono-, di- or trisubstituted independently of one another by R14, or G is a direct bond, —(CH$_2$)$_m$—, or —(CH$_2$)$_m$—NR$^{10}$—, m is the integers zero, 1, 2, 3 or 4, M is
1) a hydrogen atom,
2) heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiomorpholine, thiophene, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14,
3) —(C$_1$-C$_6$)-alkyl, wherein alkyl is unsubstituted or mono-, di- or trisubstituted independently of one another by R14,
4) (C$_3$-C$_6$)-cycloalkyl or
5) —C(O)—N(R$^{11}$)—R$^{12}$, R3 is
1) hydrogen atom,
2) halogen,
3) —(C$_1$-C$_4$)-alkyl, wherein alkyl is unsubstituted or mono-, di- or trisubstituted independently of one another by R13,
4) —(C$_1$-C$_3$)-perfluoroalkyl,
5) phenyl, wherein phenyl is unsubstituted or mono-, di- or trisubstituted independently of one another by R13,
6) —(C$_0$-C$_4$)-alkylene-O—R19, wherein R19 is
   a) hydrogen atom,
   b) —(C$_1$-C$_4$)-alkyl, wherein alkyl is unsubstituted or mono-, di- or trisubstituted independently of one another by R13,
   c) —CF$_3$, or
   d) CHF$_2$,
7) —CN,
8) —NR$^{10}$—SO$_2$—R$^{10}$,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —(C$_0$-C$_2$)alkylene-C(O)—O—(C$_2$-C$_4$)-alkylene-O—C(O)—(C$_1$-C$_4$)-alkyl,
16) —C(O)—O—C(R15, R16)-O—C(O)—R17,
17) —(C$_0$-C$_2$)alkylene-C(O)—O—(C$_2$-C$_4$)-alkylene-O—C(O)—O—(C$_1$-C$_6$)-alkyl,
18) —C(O)—O—C(R15, R16)-O—C(O)—O—R17,
19) —(C$_0$-C$_3$)-alkylene-O—CH$_2$—CF$_2$—CH$_2$—O—(C$_0$-C$_3$)-alkyl,
20) —(C$_0$-C$_3$)-alkylene-O—CH$_2$—CF$_2$—CF$_2$—CH$_2$—O—(C$_0$-C$_3$)-alkyl,
21) —(C$_0$-C$_3$)-alkylene-O—CH$_2$—(C$_1$-C$_3$)-perfluoroalkylene-CH$_2$—OH,
22) —SO$_w$—N(R$^{11}$)—R$^{13}$, wherein w is 1 or 2,
23) —(C$_0$-C$_4$)-alkylene-C(O)—N(R$^{11}$)—R$^{13}$, 24) —(C₀-C₄)-alkylene-N(R¹¹)—R¹³, or
25) a residue from the following list

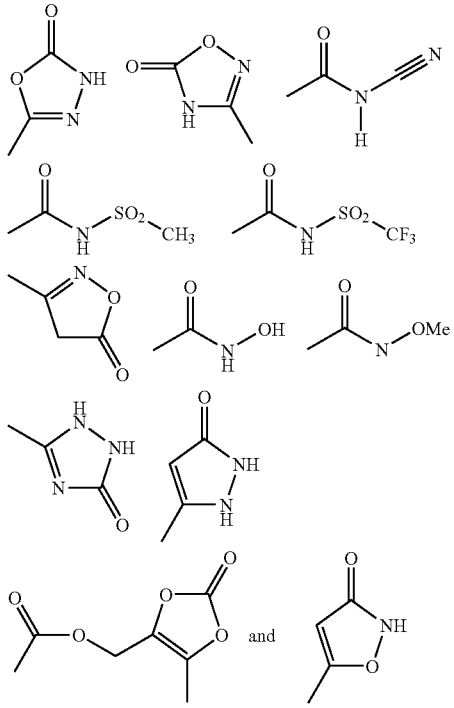

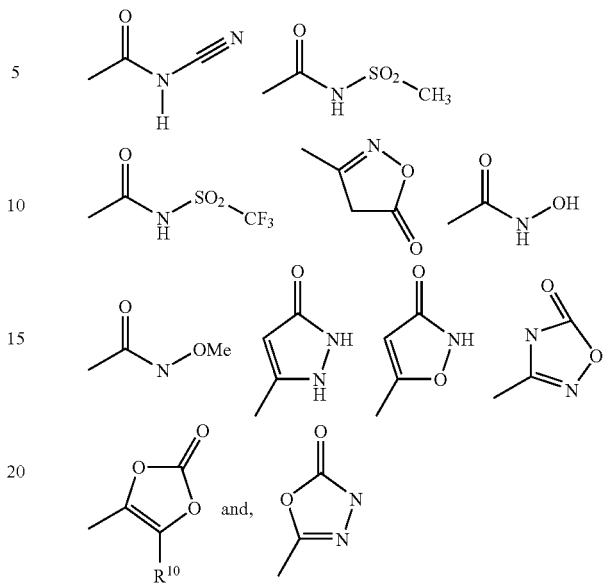

and, wherein Me is methyl, if two —OR19 residues are attached to adjacent atoms they can form together with the atoms which they are attached to a 1,3-dioxole ring or a 2,3-dihydro-[1,4]dioxine ring, which is substituted one, two, three or four times by R13, R¹¹ and R¹² together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said ring is unsubstituted or mono-, di- or trisubstituted independently of one another by R13, R13 is fluorine, chlorine, —NO₂, —CN, =O, —OH, —CF₃, —C(O)—O—R¹⁰, —C(O)—N(R¹⁰)—R²⁰, —N(R¹⁰)—R²⁰, —(C₀-C₃)-alkylene-O—R¹⁰, —Si—(CH₃)₃, —N(R¹⁰)—S(O)₂—R¹⁰, —S—R¹⁰, —SO₂—R¹⁰, —S(O)₂—N(R¹⁰)—R²⁰, —C(O)—R¹⁰, —(C₁-C₈)-alkyl, —(C₁-C₈)-alkoxy, phenyl, phenyloxy-, —O—CF₃, —(C₁-C₃)-perfluoroalkyl, —NH—C(O)—NH—R¹⁰, —(C₀-C₄)-alkyl-C(O)—O—C(R15, R16)-O—C(O)—R17, —(C₁-C₄)-alkoxy-phenyl, —(C₀-C₄)-alkyl-C(O)—O—C(R15, R16)-O—C(O)—O—R17, —O—R15, —NH—C(O)—O—R¹⁰, or a residue from the following list wherein Me is methyl, R¹⁰ and R²⁰ are independently of one another hydrogen, —(C₁-C₆)-alkyl, —(C₀-C₄)-alkyl-OH, —(C₀-C₄)-alkyl-O—(C₁-C₄)-akyl or —(C₁-C₃)-perfluoroalkyl, R15 and R16 are independently of one another hydrogen, —(C₁-C₆)-alkyl, or together form a ring out of the droup cyclopropyl, cyclobutyl, cyclopentyl or cyclohexyl, wherein each ring is unsubstituted or substituted one to three times by R¹⁰, and R17 is —(C₁-C₆)-alkyl, —(C₁-C₆)-alkyl-OH, —(C₁-C₆)-alkyl-O—(C₁-C₆)-alkyl, —(C₃-C₈)-cycloalkyl, —(C₁-C₆)-alkyl-O—(C₁-C₈)-alkyl-(C₃-C₈)-cycloalkyl, —(C₁-C₆)-alkyl-(C₃-C₈)-cycloalkyl, wherein said cycloalkyl ring is unsubstituted or substituted one, two or three times by —OH, —O—(C₁-C₄)-alkyl or R¹⁰, in all its stereoisomeric forms and mixtures thereof in any ratio, and its physiologically tolerable salts.

Another particular embodiment of the present invention relates to the compounds of the formula I, wherein R⁰ is
1) phenyl, wherein phenyl is unsubstituted or mono-, di- or trisubstituted independently of one another by R8,
2) a heterocyclyl selected out of the group indolyl, isoindolyl, benzofuranyl, benzothiophenyl, 1,3-benzodioxolyl, indazolyl, benzimidazolyl, benzoxazolyl, benzothiazolyl, quinolinyl, isoquinolinyl, chromanyl, isochromanyl, cinnolinyl, quinazolinyl, quinoxalinyl, phthalazinyl, pyridoimidazolyl, pyridopyridinyl, pyridopyrimidinyl, pyridyl, purinyl and pteridinyl, wherein said heterocyclyl is unsubstituted or mono-, di- or trisubstituted independently of one another by R8,
3) a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8, and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8

R8 is
1) is F, Cl, Br, J,
2) —C(O)—NH$_2$,
3) —(C$_1$-C$_4$)-alkyl, wherein alkyl is unsubstituted or mono-, di- or trisubstituted independently of one another by halogen, —OH or a methoxy residue, or
4) —O—(C$_1$-C$_4$)-alkyl, wherein alkyl is unsubstituted or mono-, di- or trisubstituted independently of one another by halogen or a methoxy residue,
provided that R8 is at least one halogen, —C(O)—NH$_2$ or —O—(C$_1$-C$_8$)-alkyl residue, if R0 is a aryl or a heterocyclyl, which are as defined above, substructure D is a residue selected out of the group pyridyl, pyridyl-N-oxide, pyrrolyl, furyl, thienyl, imidazolyl, pyrazolyl, oxazolyl, isoxazolyl, thiazolyl, triazolyl, isothiazolyl, thiadiazolyl, pyrimidinyl, pyridazinyl, pyrazinyl and is unsubstituted or substituted 1, 2, 3 or 4 times by R$^3$, or is substituted 1 or 2 times by =O, Q is a direct bond, —C(O)—; —SO$_2$—, —(C$_1$-C$_6$)-alkylen, or
—(C$_0$-C$_2$)-alkylen-C(O)—NR$^{10}$—, R$^1$ is hydrogen atom or —(C$_1$-C$_2$)-alkyl,
R$^2$ is a direct bond or —(C$_1$-C$_2$)-alkylen, or
R$^1$—N—R$^2$—V can form a 4- to 7- membered cyclic group out of the group piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14, R14 is fluorine, chlorine, =O, —(C$_1$-C$_4$)-alkyl or —NH$_2$,
V is
1) a cyclic residue out of the group containing compounds, which are derived from azaindolyl (1H-pyrrolopyridyl), azetidine, azepine, aziridine, azirine, 1,4-diazepane, 1,2-diazepine, 1,3-diazepine, 1,4-diazepine, diazirine, 1,3-dioxolane, dioxazole, furan, imidazole, isoquinoline, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, quinazoline, quinoline, tetrazine, tetrazole, thiadiazine, 1,2-thiazine, 1,3-thiazine, 1,4-thiazine, 1,3-thiazole, thietan, thiomorpholine, thiophene, thiopyran, 1,2,3-triazine, 1,2,4-triazine, 1,3,5-triazine, 1,2,3-triazole or 1,2,4-triazole,
wherein said cyclic residue is unsubstituted or mono-, di- or trisubstituted independently of one another by R14, or
2) phenyl, wherein phenyl is unsubstituted or mono-, di- or trisubstituted independently of one another by R14, G is a direct bond, —(CH$_2$)$_m$—, or —(CH$_2$)$_m$—NR$^{10}$—,
m is the integers zero, 1, 2, 3 or 4, M is
1) a hydrogen atom,
2) heterocyclyl, wherein heterocyclyl is a residue out of the group which can be derived from 1,4-diazepane, ketomorpholine, thiophene, pyridazone, piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, 1,4,5,6-tetrahydro-pyridazinyl, thiadiazole or thiomorpholine, wherein said heterocyclyl is unsubstituted or mono-, di- or trisubstituted independently of one another by R14,
3) —(C$_1$-C$_6$)-alkyl, wherein alkyl is unsubstituted or mono-, di- or trisubstituted independently of one another by R14, or
4) (C$_3$-C$_6$)-cycloalkyl, R3 is
1) hydrogen atom,
2) halogen,
3) —(C$_1$-C$_4$)-alkyl, wherein alkyl is unsubstituted or mono-, di- or trisubstituted independently of one another by R13,
4) —(C$_1$-C$_3$)-perfluoroalkyl,
5) phenyl, wherein phenyl is unsubstituted or mono-, di- or trisubstituted independently of one another by R13,
6) —(C$_0$-C$_4$)-alkylene-O—R19, wherein R19 is
 a) hydrogen atom,
 b) —(C$_1$-C$_4$)-alkyl, wherein alkyl is unsubstituted or mono-, di- or trisubstituted independently of one another by R13,
 c) —CF$_3$ or
 d) —CHF$_2$,
7) —CN,
8) —NR$^{10}$—SO$_2$—R$^{10}$,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —(C$_0$-C$_2$)alkylene-C(O)—O—(C$_2$-C$_4$)-alkylene-O—C(O)—(C$_1$-C$_4$)-alkyl,
16) —C(O)—O—C(R15, R16)-O—C(O)—R17,
17) —(C$_0$-C$_2$)alkylene-C(O)—O—(C$_2$-C$_4$)-alkylene-O—C(O)—O—(C$_1$-C$_6$)-alkyl,
18) —C(O)—O—C(R15, R16)-O—C(O)—O—R17, or
19) a residue from the following list

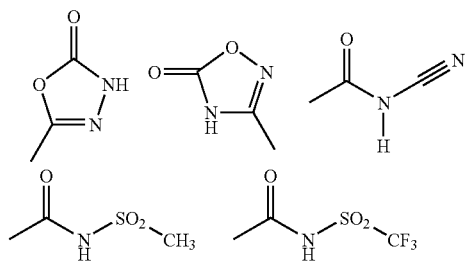

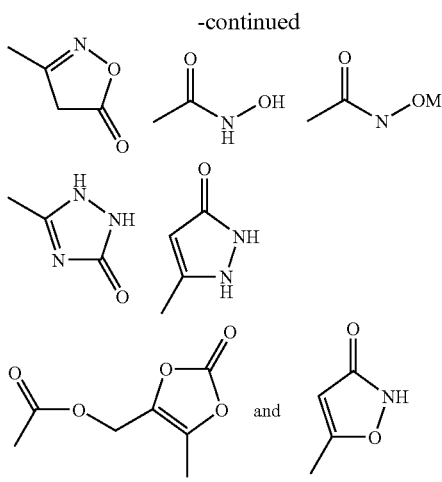

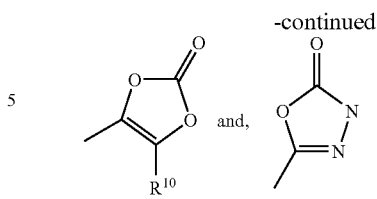

wherein Me is methyl,
R11 and R12 are independently of one another identical or different and are
1) hydrogen atom,
2) —($C_1$-$C_4$)-alkyl, wherein alkyl is unsubstituted or mono-, di- or trisubstituted independently of one another by R13,
3) —($C_0$-$C_6$)-alkyl-($C_3$-$C_6$)-cycloalkyl,
4) —O—$R^{17}$, or
5) —($C_0$-$C_6$)-alkyl-($C_4$-$C_{15}$)-heterocyclyl, wherein alkyl and heterocyclyl independently from one another are unsubstituted or mono-, di- or trisubstituted by R13 and wherein heterocyclyl is selected out of the group azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine or thiomorpholine, or R11 and R12 together with the nitrogen atom to which they are bonded form a heterocyclic ring, which is selected out of the group azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine or thiomorpholine, R13 is fluorine, —CN, =O, —OH, —$CF_3$, —C(O)—O—$R^{10}$, —C(O)—N($R^{10}$)—$R^{20}$, —N($R^{10}$)—$R^{20}$, —($C_3$-$C_6$)-cycloalkyl, —($C_0$-$C_3$)-alkylene-O—$R^{10}$, —Si—($CH_3$)$_3$, —S—$R^{10}$, —$SO_2$—$R^{10}$, —($C_1$-$C_3$)-perfluoroalkyl, or a residue from the following list

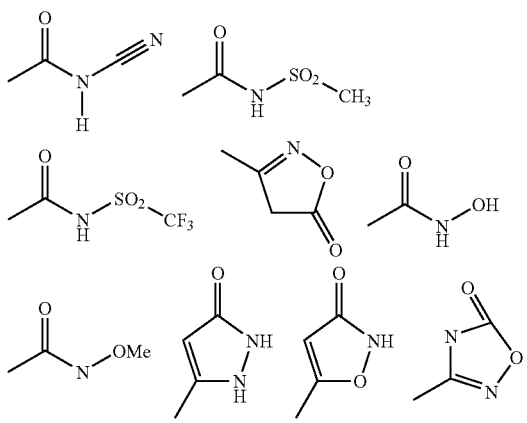

wherein Me is methyl,
$R^{10}$ and $R^{20}$ are independently of one another hydrogen, —($C_1$-$C_4$)-alkyl or —($C_1$-$C_3$)-perfluoroalkyl,
$R^{15}$ and $R^{16}$ are independently of one another hydrogen, —($C_1$-$C_4$)-alkyl, or together form a ring out of the droup cyclopropyl, cyclobutyl, cyclopentyl or cyclohexyl, wherein each ring is unsubstituted or substituted one to three times by $R^{10}$, and
R17 is —($C_1$-$C_6$)-alkyl, —($C_1$-$C_6$)-alkyl-OH, —($C_1$-$C_6$)-alkyl-O—($C_1$-$C_6$)-alkyl, —($C_1$-$C_6$)-alkyl-O—($C_1$-$C_8$)-alkyl-($C_3$-$C_8$)-cycloalkyl, —($C_0$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or $R^{10}$, in all its stereoisomeric forms and mixtures thereof in any ratio, and its physiologically tolerable salts.

Another particular embodiment of the present invention relates to the compound of the formula I, wherein
$R^0$ is
1) phenyl, wherein phenyl is unsubstituted or mono- or disubstituted independently of one another by R8,
2) pyridyl or benzothiophenyl, wherein pyridyl and benzothiophenyl are unsubstituted or mono- or disubstituted independently of one another by R8, or
3) a heterocyclyl out of the group thienyl, thiadiazolyl, isoxazolyl and thiazolyl, wherein said heterocyclyl is substituted by a residue selected out of the group thienyl, 2-thienyl and 3-thienyl, wherein said residue is unsubstituted or mono- or disubstituted independently of one another by R8,
R8 is F, Cl, Br, —$OCH_3$ or —C(O)—$NH_2$,
substructure D is a residue selected out of the group pyridyl, pyridyl-N-oxide, pyrrolyl, thienyl, imidazolyl, pyrazolyl, oxazolyl, isoxazolyl, thiazolyl, isothiazolyl, thiadiazolyl, pyrimidinyl, pyridazinyl or pyrazinyl and is unsubstituted or substituted 1, 2, 3 or 4 times by R3, or is substituted 1 or 2 times by =O,
Q is a direct bond, —C(O)—; —$SO_2$—, —$CH_2$—C(O)—NH—, methylene or ethylene,
$R^1$ is hydrogen atom,
$R^2$ is a direct bond or methylene,
$R^1$—N—$R^2$—V can form a 4- to 7-membered cyclic group out of the group azetidine, pyrrolidine, piperidine and piperazine,
R14 is fluorine, chlorine, =O, methyl, ethyl or —$NH_2$,
V is
1) a residue out of the group containing compounds which is derived from azaindolyl (1H-pyrrolopyridyl), azetidine, 1,4-diazepane, isoxazole, isoquinoline, piperazine, piperidine, pyrazine, pyridazine, pyrimidine, pyrrolidine, quinazoline, quinoline or tetrahydropyrane, wherein said cyclic residue is unsubstituted or mono- or disubstituted independently of one another by R14, or
2) phenyl, wherein phenyl is unsubstituted or mono- or disubstituted independently of one another by R14, G is a direct bond, —(CH$_2$)$_m$—, or —(CH$_2$)$_m$—NR$^{10}$, m is the integers zero, 1 or 2, M is a hydrogen atom, (C$_2$-C$_4$)-alkyl, azepanyl, cyclopropyl, cyclobutyl, cyclopentyl, cyclohexyl, imidazolyl, ketomorpholinyl, morpholinyl, [1,4]Oxazepanyl, piperidinyl, piperidonyl, pyrazinyl, pyrazolyl, pyridazinyl, pyridyl, pyrimidyl, pyrrolidinyl, 1,4,5,6-tetrahydro-pyridazinyl, or tetrahydropyranyl, wherein the residues are unsubstituted or mono- or disubstituted independently of one another by R14

R3 is
1) hydrogen atom,
2) fluorine, chlorine,
3) —(C$_1$-C$_4$)-alkyl, wherein alkyl is unsubstituted or mono-, di- or trisubstituted independently of one another by R13,
4) —(C$_1$-C$_3$)-perfluoroalkyl,
5) phenyl, wherein phenyl is unsubstituted or mono-, di- or trisubstituted independently of one another by R13,
6) —(C$_0$-C$_2$)-alkylene-O—R19, wherein R19 is
   a) hydrogen atom,
   b) —(C$_1$-C$_4$)-alkyl, wherein alkyl is unsubstituted or mono-, di- or trisubstituted independently of one another by R13,
   c) —CF$_3$, or
   d) —CHF$_2$,
7) —CN,
8) —NR$^{10}$—SO$_2$—R$^{10}$,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —(C$_0$-C$_2$)alkylene-C(O)—O—(C$_2$-C$_4$)-alkylene-O—C(O)—(C$_1$-C$_4$)-alkyl,
16) —C(O)—O—C(R15, R16)-O—C(O)—R17,
17) —(C$_0$-C$_2$)alkylene-C(O)—O—(C$_2$-C$_4$)-alkylene-O—C(O)—O—(C$_1$-C$_6$)-alkyl, or
18) —C(O)—O—C(R15, R16)-O—C(O)—O—R17, R11 and R12 are independently of one another identical or different and are
1) hydrogen atom,
2) —(C$_1$-C$_4$)-alkyl, wherein alkyl is unsubstituted or mono-, di- or trisubstituted independently of one another by R13,
3) —(C$_0$-C$_6$)-alkyl-(C$_3$-C$_6$)-cycloalkyl,
4) —O—R$^{17}$, or
5) —(C$_0$-C$_6$)-alkyl-heterocyclyl, wherein alkyl and heterocyclyl independently from one another are unsubstituted or mono-, di- or trisubstituted by R13 and wherein heterocyclyl is selected out of the group azetidine, imidazolidine, morpholine, (1,4)-oxazepane or pyrrolidine or R11 and R12 together with the nitrogen atom to which they are bonded can form a ring, which is selected out of the group azetidine, imidazolidine, morpholine, (1,4)-oxazepane piperazine, piperidine, pyrrolidine or thiomorpholine, R13 is fluorine, —CN, ═O, —OH, —CF$_3$, —C(O)—O—R$^{10}$, —C(O)—N(R$^{10}$)—R$^{20}$, —N(R$^{10}$)—R$^{20}$, —(C$_3$-C$_6$)-cycloalkyl, —(C$_0$-C$_3$)-alkylene-O—R$^{10}$, —Si—(CH$_3$)$_3$, —S—R$^{10}$, —SO$_2$—R$^{10}$, or —(C$_1$-C$_3$)-perfluoroalkyl, R$^{10}$ and R$^{20}$ are independently of one another hydrogen, —(C$_1$-C$_4$)-alkyl or —(C$_1$-C$_3$)-perfluoroalkyl, R$^{15}$ and R$^{16}$ are independently of one another hydrogen, —(C$_1$-C$_4$)-alkyl, or together form a ring out of the droup cyclopropyl, cyclobutyl, cyclopentyl or cyclohexyl, wherein each ring is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_1$-C$_6$)-alkyl-O—(C$_1$-C$_8$)-alkyl-(C$_3$-C$_8$)-cycloalkyl, —(C$_0$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

Another particular embodiment of the present invention relates to the compound of the formula I, wherein R0 is
1) pyridyl or benzothiophenyl, wherein pyridyl and benzothiophenyl are unsubstituted or mono- or disubstituted independently of one another by R8, or
2) a heterocyclyl out of the group thienyl, thiadiazolyl, isoxazolyl and thiazolyl, wherein said heterocyclyl is substituted by a residue selected out of the group thienyl, 2-thienyl and 3-thienyl, wherein said residue is unsubstituted or mono- or disubstituted independently of one another by R8, R8 is F, Cl, Br, —OCH$_3$ or —C(O)—NH$_2$, substructure D is pyridyl and is unsubstituted or substituted 1, 2, 3 or 4 times by R3, or is substituted 1 or 2 times by ═O, Q is —CH$_2$—C(O)—NH— or methylene, R$^1$ is hydrogen atom, R$^2$ is a direct bond, R14 is fluorine, chlorine, ═O, methyl, ethyl or —NH$_2$, V is piperidine, wherein piperidine is unsubstituted or mono- or disubstituted independently of one another by R14, or G is a direct bond, M is a hydrogen atom, (C$_2$-C$_4$)-alkyl, isopropyl, or pyridyl, wherein the residue is unsubstituted or mono- or disubstituted independently of one another by R14

R3 is
1) hydrogen atom,
2) fluorine, chlorine,
3) —(C$_1$-C$_4$)-alkyl, wherein alkyl is unsubstituted or mono-, di- or trisubstituted independently of one another by R13,
4) —(C$_0$-C$_2$)-alkylene-O—R19, wherein R19 is
   a) hydrogen atom or
   b) —(C$_1$-C$_4$)-alkyl, wherein alkyl is unsubstituted or mono-, di- or trisubstituted independently of one another by R13,
5) —(C$_0$-C$_4$)-alkylene-C(O)—O—R$^{11}$ or
6) —(C$_0$-C$_4$)-alkylene-C(O)—N(R$^{11}$)—R$^{12}$, R11 and R12 are independently of one another identical or different and are
1) hydrogen atom or
2) —(C$_1$-C$_4$)-alkyl, wherein alkyl is unsubstituted or mono-, di- or trisubstituted independently of one another by R13, or R11 and R12 together with the nitrogen atom to which they are bonded can form a ring, which is selected out of the group azetidine, imidazolidine, morpholine, (1,4)-oxazepane piperazine, piperidine, pyrrolidine or thiomorpholine, R13 is fluorine, ═O, —OH, —CF$_3$, —C(O)—O—R$^{10}$, —C(O)—N(R$^{10}$)—R$^{20}$, —N(R$^{10}$)—R$^{20}$, or —(C$_0$-C$_3$)-alkylene-O—R$^{10}$, R$^{10}$ and R$^{20}$ are independently of one another hydrogen, —(C$_1$-C$_4$)-alkyl or —(C$_1$-C$_3$)-perfluoroalkyl, in all its stereoisomeric forms and mixtures thereof in any ratio, and its physiologically tolerable salts.

Another particular embodiment of the present invention relates to the compound of the formula I, which is 1-[5-(5-Chloro-thiophen-2-yl)-isoxazol-3-ylmethyl]-1H-pyrrolo[2,3-b]pyridine-2-carboxylic acid (1-isopropyl-piperidin-4-yl)-amide, 1-[5-(5-Chloro-thiophen-2-yl)-isoxazol-3-ylmethyl]-2-(1-isopropyl-piperidin-4-ylcarbamoyl)-1H-pyrrolo[2,3-b]pyridine-5-carboxylic acid methyl ester, 1-[5-(5-Chloro-thiophen-2-yl)-isoxazol-3-ylmethyl]-2-(1-isopropyl-piperidin-4-ylcarbamoyl)-1H-pyrrolo[2,3-b]pyridine-5-carboxylic acid, 1-[5-(5-Chloro-thiophen-2-yl)-isoxazol-3-ylmethyl]-1H-pyrrolo[2,3-b]pyridine-2,5-dicarboxylic acid 5-amide 2-[(1-isopropyl-piperidin-4-yl)-amide], 1-[5-(5-Chloro-thiophen-2-yl)-isoxazol-3-ylmethyl]-1H-pyrrolo[3,2-b]pyridine-2-carboxylic acid (1-isopropyl-piperidin-4-yl)-amide, 1-[5-(5-Chloro-thiophen-2-yl)-isoxazol-3-ylmethyl]-2-(1-isopropyl-piperidin-4-ylcarbamoyl)-1H-pyrrolo[3,2-b]pyridine-5-carboxylic acid, 1-[5-(5-Chloro-thiophen-2-yl)-isoxazol-3-ylmethyl]-5-oxo-4,5-dihydro-1H-pyrrolo[3,2-b]pyridine-2-carboxylic acid (1-isopropyl-piperidin-4-yl)-amide, 1-[5-(5-Chloro-thiophen-2-yl)-isoxazol-3-ylmethyl]-2-(3,4,5,6-tetrahydro-2H-[1,4']bipyridinyl-4-ylcarbamoyl)-1H-pyrrolo[3,2-b]pyridine-5-carboxylic acid methyl ester, 1-[5-(5-Chloro-thiophen-2-yl)-isoxazol-3-ylmethyl]-2-(3,4,5,6-tetrahydro-2H-[1,4']bipyridinyl-4-ylcarbamoyl)-1H-pyrrolo[3,2-b]pyridine-5-carboxylic acid, 1-[5-(5-Chloro-thiophen-2-yl)-isoxazol-3-ylmethyl]-5-(2-methoxy-ethoxy)-1H-pyrrolo[2,3-c]pyridine-2-carboxylic acid (1-isopropyl-piperidin-4-yl)-amide, 1-[5-(5-Chloro-thiophen-2-yl)-isoxazol-3-ylmethyl]-5-(2-hydroxy-ethoxy)-1H-pyrrolo[2,3-c]pyridine-2-carboxylic acid (1-isopropyl-piperidin-4-yl)-amide, 1-[(5-Chloro-pyridin-2-ylcarbamoyl)-methyl]-5-(2-methoxy-ethoxy)-1H-pyrrolo[2,3-c]pyridine-2-carboxylic acid (1-isopropyl-piperidin-4-yl)-amide, 1-[(5-Chloro-pyridin-2-ylcarbamoyl)-methyl]-5-(2-hydroxy-ethoxy)-1H-pyrrolo[2,3-c]pyridine-2-carboxylic acid (1-isopropyl-piperidin-4-yl)-amide, 1-(6-Chloro-benzo[b]thiophen-2-ylmethyl)-5-(2-methoxy-ethoxy)-1H-pyrrolo[2,3-c]pyridine-2-carboxylic acid (1-isopropyl-piperidin-4-yl)-amide, or 1-(6-Chloro-benzo[b]thiophen-2-ylmethyl)-5-(2-hydroxy-ethoxy)-1H-pyrrolo[2,3-c]pyridine-2-carboxylic acid (1-isopropyl-piperidin-4-yl)-amide.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The present invention furthermore includes all solvates of compounds of the formula I, for example hydrates or adducts with alcohols.

The invention also includes derivatives and modifications of the compounds of the formula I, for example prodrugs, protected forms and other physiologically tolerable derivatives, as well as active metabolites of the compounds of the formula I. The invention relates in particular to prodrugs and protected forms of the compounds of the formula I, which can be converted into compounds of the formula I under physiological conditions. Suitable prodrugs for the compounds of the formula I, i. e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443 which are all incorporated herein by reference. Suitable prodrugs for the compounds of the formula I are especially acyl prodrugs and carbamate prodrugs of acylatable nitrogen-containing groups such as amino groups and the guanidino group and also ester prodrugs and amide prodrugs of carboxylic acid groups which may be present in compounds of the formula I. In the acyl prodrugs and carbamate prodrugs one or more, for example one or two, hydrogen atoms on nitrogen atoms in such groups are replaced with an acyl group or a carbamate, preferably a —($C_1$-$C_6$)-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, ($C_1$-$C_{18}$)-alkyl, ($C_3$-$C_8$)-cycloalkyl, ($C_3$-$C_8$)-cycloalkyl-($C_1$-$C_4$)-alkyl-, ($C_6$-$C_{14}$)-aryl, Het-, ($C_6$-$C_{14}$)-aryl-($C_1$-$C_4$)-alkyl- or Het-($C_1$-$C_4$)-alkyl- and in which $R^{p2}$ has the meanings indicated for $R^{p1}$ with the exception of hydrogen.

Especially preferred compounds of the formula I are those wherein two or more residues are defined as indicated before for preferred compounds of the formula I, or residues can have one or some of the specific denotations of the residues given in their general definitions or in the definitions of preferred compounds before. All possible combinations of definitions given for preferred definitions and of specific denotations of residues explicitly are a subject of the present invention.

Also with respect to all preferred compounds of the formula I all their stereoisomeric forms and mixtures thereof in any ratio and their physiologically acceptable salts explicitly are a subject of the present invention, as well as are their prodrugs. Similarly, also in all preferred compounds of the formula I, all residues that are present more than one time in the molecule are independent of each other and can be identical or different.

The compounds of the formula I can be prepared by utilising procedures and techniques, which per se are well known and appreciated by one of ordinary skill in the art. Starting materials or building blocks for use in the general synthetic procedures that can be applied in the preparation of the compounds of formula I are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, compounds of the formula I can be prepared, for example in the course of a convergent synthesis, by linking two or more fragments which can be derived retrosynthetically from the formula I. More specifically, suitably substituted starting azaindole derivatives are employed as building blocks in the preparation of the compounds of formula I. Although various synthetic aspects of the azaindole chemistry are considerably different to the indole chemistry many procedures describing the synthesis and functionalisation of indoles can be modified and adopted by those skilled in the art. Therefore literature describing transformations and the synthesis of indoles are highly instructive and applicable to the azaindole chemistry. If not commercially available, such azaindole derivatives can be prepared according to the well-known standard procedures for the formation of the azaindole ring system such as, for example, the Fischer indole synthesis, the Bischler indole synthesis, or the Reissert indole synthesis. By choosing suitable precursor molecules, these azaindole syntheses allow the introduction of a variety of substituents into the various positions of the azaindole system, which can then be chemically modified in order to finally arrive at the molecule of the formula I having the desired substituent pattern. As one of the comprehensive reviews in which numerous details and literature references on the chemistry of indoles and on synthetic procedures for their preparation can be found, W. J. Houlihan (ed.), "Indoles, Part one", volume 25, 1972, out of the series "The Chemistry of Heterocyclic Compounds", A. Weissberger and E. C. Taylor (ed.), John Wiley & Sons; R. E. Willette, Advances in Heterocyclic Chemistry 9 (1968) 27; J.-Y. Mérour Curr. Org. Chem. 5 (2001) 471; H. Döpp et al. in Houben-Weyl, "Methoden der Organischen Chemie" (Methods of Organic Chemistry), Georg Thieme Verlag, Stuttgart, Germany 1994, Vol E6a,b part 2a Hetarene I, is referred to.

If starting azaindole derivatives are to be synthesized this can be done, for example, according to the well-known azaindole syntheses mentioned above. In the following they are explained briefly, however, they are standard procedures comprehensively discussed in the literature, and are well known to one skilled in the art.

The Fischer indole synthesis comprises the acid cyclization of heteroarylhydrazones, for example of the general formula 2,

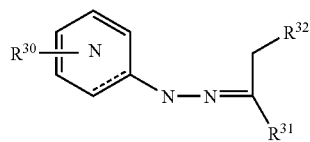

2 which can be obtained by various methods and in which $R^{30}$, $R^{31}$ and $R^{32}$ can have a wide variety of denotations. Besides hydrogen and alkyl, $R^{31}$ and $R^{32}$ can especially denote ester groups or methyl or ethyl groups or 2,2,2-trifluoroethyl groups carrying an ester group as substituent thus allowing the introduction into the azaindole molecule of the $(CH_2)_p$—CO moiety occurring in the groups $R^2$ and/or $R^3$ in the compounds of the formula I. As examples of the many literature references describing the synthesis of azaindole derivatives according to the Fischer synthesis, besides the above-mentioned book edited by Houlihan, the following articles are mentioned: F. G. Salituro et al., J. Med. Chem. 33 (1990) 2944; N. M. Gray et al., J. Med. Chem. 34 (1991) 1283; J. Sh. Chikvaidze et al., Khim. Geterotsikl. Soedin. (1991) 1508; S. P. Hiremath et al., Indian J. Chem. 19 (1980) 770; J. Bornstein, J. Amer. Chem. Soc. 79 (1957) 1745; S. Wagaw, B. Yang and S. Buchwald, J. Am. Chem. Soc. 121 (1999) 10251 or by Y. Murakami, Y. Yokoyama, T. Miura, H. Hirasawa Y. Kamimura and M. Izaki, Heterocycles 22 (1984) 1211; D. L. Hughes, Org. Prep. Proc. 25 (1993) 607.

The Reissert indole synthesis comprises the reductive cyclization of o-nitrophenylpyruvic acids or esters thereof, for example of the general formula 3,

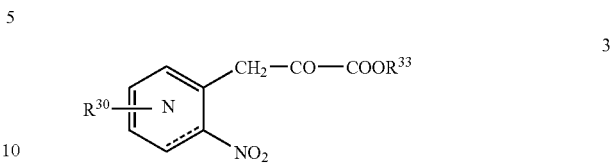

3 in which the groups $R^{30}$ can have a wide variety of denotations and can be present in all positions of the aromatic ring. The Reissert indole synthesis leads to derivatives of azaindole-2-carboxylic acids. The pyruvic acid derivatives of the formula 3 can be obtained by condensation of oxalic acid esters with substituted o-nitromethylazabenzenes. As literature references, besides the above-mentioned book edited by Houlihan and the literature articles mentioned therein, for example the articles by H. G. Lindwall and G. J. Mantell, J. Org. Chem. 18 (1953) 345 or by H. Burton and J. L. Stoves, J. Chem. Soc. (1937) 1726 or by W. Noland, F. Baude, Org. Synth Coll. Vol. V, J. Wiley, New York, (1973) 567 are mentioned.

Another method to gain regioselective access to the azaindole structure involves palladium catalysis, for example o-haloanilines (X=Cl, Br, I) or o-trifluoromethanesulfonyloxyanilines (X=OTf) of the general formula 4 can be cyclized to azaindoles utilizing several alkynes by adopting procedures described by J. Ezquerra, C. Pedregal. C. Lamas, J. Barluenga, M. Pérez, M. Garcia-Martin, J. Gonzalez, J. Org. Chem. 61 (1996) 5805; or F. Ujjainwalla, D. Warner, Tetrahedron Lett. 39 (1998) 5355 and furthermore A. Rodriguez, C. Koradin, W. Dohle, P. Knochel, Angew. Chem. 112 (2000) 2607; or R. Larock, E. Yum, M. Refvik, J. Org. Chem. 63 (1998) 7653; R. Larock, E. Yum, J. Am. Chem. Soc. 113 (1991) 6689; K. Roesch; R Larock, J. Org. Chem. 66 (2001) 412

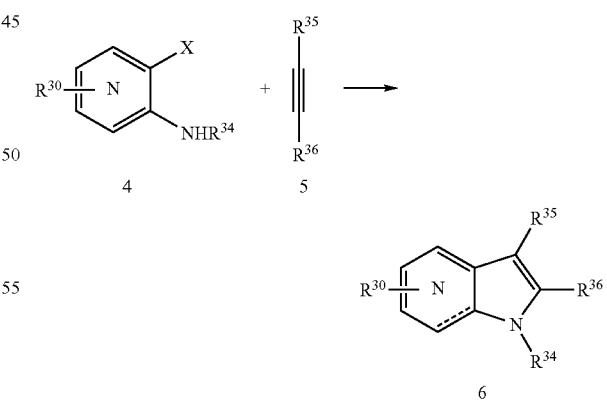

Alternatively the azaindole structure can be built up by employment of a variety of ketones under palladium catalysis by adopting and modifying a procedure described by C. Chen, D. Liebermann, R. Larsen, T. Verhoeven and P. Reider J. Org. Chem. 62 (1997) 2676 as indicated below were X=Cl, Br, I or OTf:

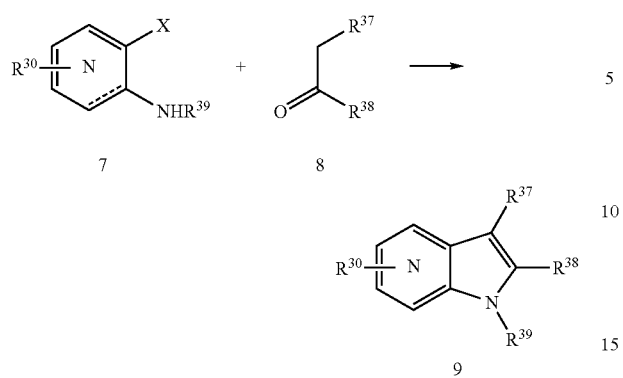

According to the Bischler indole synthesis ∀-aza-anilinoketones, for example of the general formula 10,

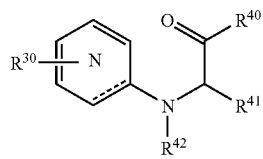

can be cyclized to azaindole derivatives.

A further route to specifically substituted azaindole derivatives proceeds via 2,3-dihydroazaindoles (azaindolines) which can be easily obtained by reduction of azaindoles, for example by hydrogenation, or by cyclization of suitable azaphenylethylamine derivatives. Azaindolines can undergo a variety of electrophilic aromatic substitution reaction allowing the introduction of various substituents into the aromatic nucleus which cannot directly be introduced by such reactions into the aromatic nucleus of the azaindole molecule. The azaindolines can then be dehydrogenated to the corresponding azaindoles, for example with reagents like chloranil, or palladium together with a hydrogen acceptor. Again, details on these syntheses can be found in the above-mentioned book edited by Houlihan.

Moreover 2-H-azaindoles can be converted into the corresponding carboxylic acids or carboxylic esters by lithiation of the 2-position of the azaindoles of the general formula 13 and subsequent reaction with carbon dioxide or alkylchloroformate according to I. Hasan, E. Marinelli, L. Lin, F. Fowler, A. Levy, J. Org. Chem. 46 (1981) 157; T. Kline J. Heterocycl. Chem. 22 (1985) 505; J.-R Dormoy, A. Heymes, Tetrahedron 49, (1993) 2885; E. Desarbre, S. Coudret, C. Meheust, J.-Y. Mérour, Tetrahedron 53 (1997) 3637 as indicated below:

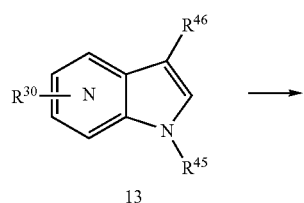

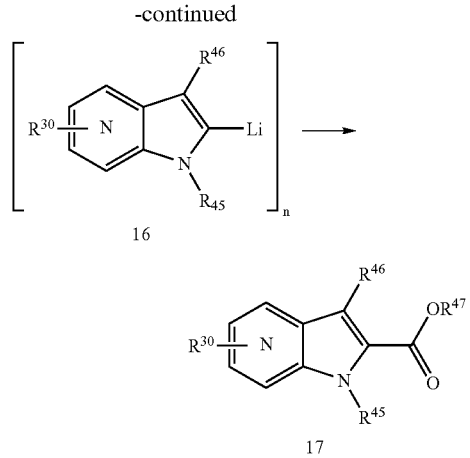

$R^{45}$ denotes hydrogen or a protecting group like for example benzenesulfonyl or tert-butoxycarbonyl. In the following further procedures of particuluar interest for the embodiment of this invention are listed and referenced briefly, however, they are standard procedures comprehensively discussed in the literature, and are well known to one skilled in the art.

1) T. Sakamoto et al., Chem. Pharm. Bull. 34 (1986) 2362.

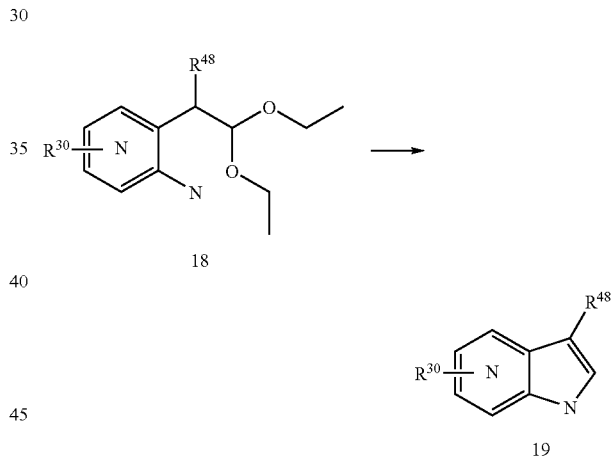

2) a) I. Mahadevan et al., J. Heterocycl. Chem. 29 (1992) 359
   b) J.-R. Dormoy et al., Tetrahedron 49 (1993) 2885

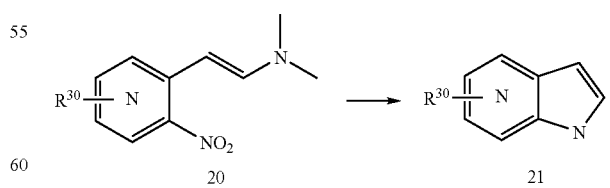

3) a) L. Estel et al., J. Org. Chem. 53 (1988) 2740
   b) D. Hands et al., Synthesis (1996) 877
   c) T. Kumiko et al., Bioorg. Med. Chem. Lett. 20 (2000) 2347

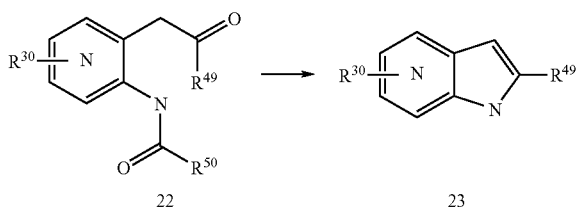

22    23

4) a) S. Clemo et al., J. Chem. Soc. (1945) 603
   b) R. Okuda, J. Org. Chem. 24 (1959) 1008
   c) J. Turner, J. Org. Chem. 48 (1983) 3401

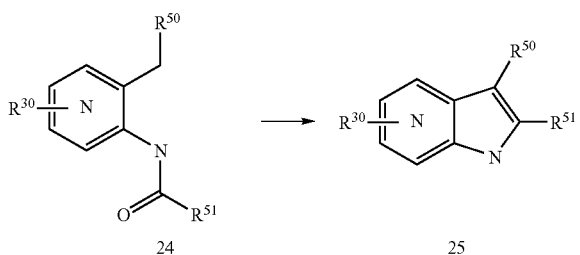

24    25

5) a) M. Davis et al., Tetrahedron 48 (1992) 939
   b) C. Martin et al., Tetrahedron Lett. 30 (1989) 935
   c) S. Ball et al., J. Organomet. Chem. 550 (1998) 457

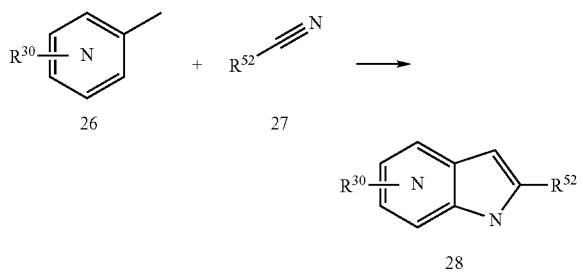

26    27

28

Depending on the substituents in the starting materials, in certain azaindole syntheses mixtures of positional isomers may be obtained which, however, can be separated by modem separation techniques like, for example, preparative HPLC.

Further, in order to obtain the desired substituents in the nucleus of the azaindole ring system in the formula I, the functional groups introduced into the ring system during the azaindole synthesis can be chemically modified. For example, azaindoles carrying a hydrogen atom in the 2-position or the 3-position can also be obtained by saponification and subsequent decarboxylation of azaindoles carrying an ester group in the respective position. Carboxylic acid groups and acetic acid groups in the 2-position and the 3-position can be converted into their homologues by usual reactions for chain elongation of carboxylic acids. Halogen atoms can be introduced into the 2-position or the 3-position, for example by reacting the respective azaindolinone with a halogenating agent such as phosphorus pentachloride analogously to the method described by J. C. Powers, J. Org. Chem. 31 (1966) 2627. The starting azaindolinones for such a synthesis can be obtained from 2-aminoheteroaryl acetic acids. Starting azaindole derivatives for the preparation of compounds of the formula I carrying a halogen substituent in the 3-position can also be obtained according to procedures described in the literature like the following. For the fluorination of 1H-azaindole-2-carboxylic acid ethyl ester derivatives in the 3-position N-fluoro-2,4,6-trimethylpyridinium triflate is the reagent of choice (T. Umemoto, S. Fukami, G. Tomizawa, K. Harasawa, K. Kawada, K. Tomita J. Am. Chem. Soc. 112 (1990) 8563). Chlorination of 1H-azaindole-2-carboxylic acid ethyl ester derivatives in the 3-position by reaction with sulfuryl chloride in benzene yields 3-chloro-1H-azaindole-2-carboxylic acid ethyl ester (Chem. Abstr. 1962, 34411-3442b); the same result can obtained by means of NCS (D. Comins, M. Killpack, Tetrahedron Lett. 33 (1989) 4337; M. Brennan, K. Erickson, F. Szmlac, M. Tansey, J. Thornton, Heterocycles 24 (1986) 2879). Bromination of 1H-azaindole-2-carboxylic acid ethyl ester derivatives in the 3-position can be achieved by reaction with NBS (M. Tani, H. Ikegami, M. Tashiro, T. Hiura, H. Tsukioka, Heterocycles 34 (1992) 2349). Analogously to the procedures described above NIS can be used efficiently for the iodination in the of 1H-azaindole-2—Carboxylic acid ethyl ester derivatives in the 3-position. Furthermore the iodination of 1H-azaindole-2-carboxylic acid ethyl ester derivatives in the 3-position the use of iodine is efficient (T. Sakamoto, T. Nagano, Y. Kondo, H. Yamanaka Chem. Pharm. Bull. 36 (1988) 2248).

Especially the groups present in the azaindole ring system can be modified by a variety of reactions and thus the desired residues $R^{3a}$ and $R^{30}$ can be obtained. For example, nitro groups can be reduced to amino group with various reducing agents, such as sulfides, dithionites, complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce or derive the residues $R^{3a}$ and $R^{30}$, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides. Carboxylic acids, carboxylic acid chlorides or carboxylic acid esters can be introduced by procedures described by F. Santangelo, C. Casagrande, G. Norcini, F. Gerli, Synth. Commun. 23 (1993) 2717; P. Beswick, C. Greenwood, T. Mowlem, G. Nechvatal, D. Widdowson, Tetrahedron 44 (1988) 7325; V. Collot, M. Schmitt, P. Marwah, J. Bourguignon, Heterocylces 51 (1999) 2823. Halogens or hydroxy groups—via the triflate or nonaflate—or primary amines—via its diazonium salt—or after interconversion to the corresponding stannane, or boronic acid—present in the azaindole structure can be converted into a variety of other functional groups like for example —CN, —CF$_3$, ethers, acids, esters, amides, amines, alkyl- or aryl groups mediated by means of transition metals, namely palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J.

Hartwig, Angew. Chem. 110 (1998) 2154; B. Yang, S. Buchwald, J. Organomet. Chem. 576 (1999) 125; T. Sakamoto, K. Ohsawa, J. Chem. Soc. Perkin Trans I, (1999), 2323; D. Nichols, S. Frescas, D. Marona-Lewicka, X. Huang, B. Roth, G. Gudelsky, J. Nash, J. Med. Chem, 37 (1994), 4347; P. Lam, C. Clark, S. Saubern, J. Adams, M. Winters, D. Chan, A. Combs, Tetrahedron Lett., 39 (1998) 2941; D. Chan, K. Monaco, R. Wang, M. Winters, Tetrahedron Lett. 39 (1998) 2933; V. Farina, V. Krishnamurthy, W. Scott, The Stille Reaction, Wiley, 1994; A. Klaspars, X. Huang, S. Buchwald, J. Am. Chem. Soc. 124 (2002) 7421; F. Kwong, A. Klapars, S. Buchwald, Org. Lett. 4 (2002) 581; M Wolter, G. Nordmann, G. Job, S. Buchwald, 4 (2002) 973)

Ester groups present in the azaindole nucleus can be hydrolyzed to the corresponding carboxylic acids, which after activation can then be reacted with amines or alcohols under standard conditions. Furthermore these ester or acid groups can be reduced to the corresponding alcohols by many standard procedures. Ether groups present at the azaindole nucleus, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups $R^{54}$ or $R^{8'}$ attached to the azaindole ring system by application of parallel synthesis methodology, beside a variety of reactions, the palladium or copper salt catalysis can be extremely useful. Such reactions are described for example in F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 110 (1998), 2154; B. Yang, S. Buchwald, J. Organomet. Chem. 576 (1999) 125; P. Lam, C. Clark, S. Saubern, J. Adams, M. Winters, D. Chan, A. Combs, Tetrahedron Lett. 39 (1998) 2941; D. Chan, K. Monaco, R. Wang, M. Winters, Tetrahedron Lett. 39 (1998) 2933; J. Wolfe, H. Tomori, J. Sadight, J. Yin, S. Buchwald, J. Org. Chem. 65 (2000) 1158; V. Farina, V. Krishnamurthy, W. Scott, The Stille Reaction, Wiley, 1994; A. Klaspars, X. Huang, S. Buchwald, J. Am. Chem. Soc. 124 (2002) 7421; F. Kwong, A. Klapars, S. Buchwald, Org. Lett. 4 (2002) 581; M Wolter, G. Nordmann, G. Job, S. Buchwald, 4 (2002) 973).

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996) in which details on the reactions and primary source literature can be found. Due to the fact that in the present case the functional groups are attached to an azaindole system it may in certain cases become necessary to specifically adapt reaction conditions or to choose specific reagents from a variety of reagents that can in principle be employed in a conversion reaction, or otherwise to take specific measures for achieving a desired conversion, for example to use protecting group techniques. However, finding out suitable reaction variants and reaction conditions in such cases does not cause any problems for one skilled in the art.

The structural elements present in the residues in the 1-position of the azaindole ring in the compounds of the formula I and in the $COR^{8'}$ group present in the 2-position and/or in the 3-position of the azaindole ring can be introduced into the starting azaindole derivative obtainable as outlined above by consecutive reaction steps using synthesis methodologies like those outlined below using procedures which per se are well known to one skilled in the art.

The residues $R^{8'}$ that can be introduced in formula 29, for example, by condensing a corresponding carboxylic acid of the formula 29 with a compound of the formula $HR^{8'}$, i. e. with an amine of the formula $HN(R^{1'})R^{2'}$—V-G-M to give a compound of the formula 30. The compound of the formula 30 thus obtained can already contain the desired final groups, i. e. the groups $R^{8'}$ and $R^{54}$ can be the groups —$N(R^{1})R^{2}$—V-G-M and $R^{0}$-Q- as defined in the formula I, or optionally in the compound of the formula 30 thus obtained subsequently the residue or the residues $R^{8'}$ and the residue $R^{54}$ are converted into the residues —$N(R^{1})R^{2}$—V-G-M and $R^{0}$-Q-, respectively, to give the desired compound of the formula I.

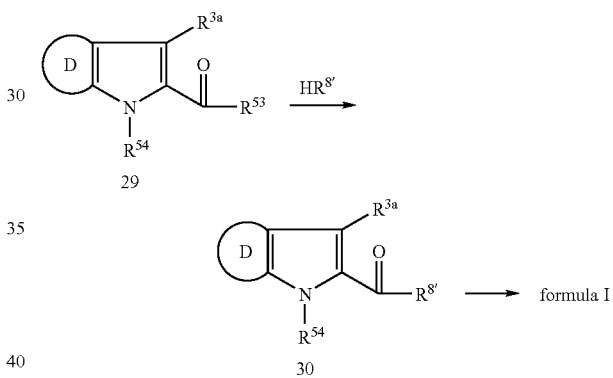

Thus, the residues $R^{8'}$ and the residues $R^{1'}$ and $R^{2'}$—V-G-M contained therein can have the denotations of $R^{1}$ and $R^{2}$—V-G-M, respectively, given above or in addition in the residues $R^{1'}$ and $R^{2'}$—V-G-M functional groups can also be present in the form of groups that can subsequently be transformed into the final groups $R^{1}$ and $R^{2}$—V-G-M, i. e. functional groups can be present in the form of precursor groups or of derivatives, for example in protected form. In the course of the preparation of the compounds of the formula I it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). As examples of precursor groups cyano groups and nitro groups may be mentioned. The cyano groups can in a later step be transformed into carboxylic acid derivatives or by reduction into aminomethyl groups, or the nitro groups which may be transformed by reduction like catalytic hydrogenation into amino groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York: Wiley, 2000). For example, a phenolic hydroxy group can be attached to a trityl-polystyrene resin, which serves as a protecting group, and the molecule is cleaved from this resin by treatment with TFA at a later stage of the synthesis.

The residue $R^{54}$ in the compounds of the formulae 29 and 30 can denote the group -Q-$R^0$ as defined above which finally is to be present in the desired target molecule of the formula I, or it can denote a group which can subsequently be transformed into the group -Q-$R^0$, for example a precursor group or a derivative of the group -Q-$R^0$ in which functional groups are present in protected form, or $R^{54}$ can denote a hydrogen atom or a protective group for the nitrogen atom of the azaindole ring. Similarly, the residues $R^{3a}$ and $R^{30}$ in the formulae 29 and 30 have the corresponding definitions of $R^3$ in formula I as defined above, however, for the synthesis of the compounds of the formula I these residues, too, can in principle be present at the stage of the condensation of a compound of the formula 29 with a compound of the formula $R^{8'}$ giving a compound of the formula 30 in the form of precursor groups or in protected form.

The residues $R^{53}$ in the compounds of the formula 29 which can be identical or different, can be, for example, hydroxy or ($C_1$-$C_4$)-alkoxy, i. e., the groups $COR^{53}$ present in the compounds of the formula 29 can be, for example, the free carboxylic acids or esters thereof like alkyl esters as can be the groups $COR^{8'}$ in the compounds of the formula I. The groups $COR^{53}$ can also be any other activated derivative of a carboxylic acid which allows amide formation, ester formation or thioester formation with a compound of the formula $HR^{8'}$. The group $COR^{53}$ can be, for example, an acid chloride, an activated ester like a substituted phenyl ester, an azolide like an imidazolide, an azide or a mixed anhydride, for example a mixed anhydride with a carbonic acid ester or with a sulfonic acid, which derivatives can all be prepared from the carboxylic acid by standard procedures and can be reacted with an amine, an alcohol or a mercaptan of the formula $HR^{8'}$ under standard conditions. A carboxylic acid group COOH representing $COR^{53}$ in a compound of the formula 29 can be obtained, for example, from an ester group introduced into the azaindole system during an azaindole synthesis by standard hydrolysis procedures.

Compounds of the formula I in which a group $COR^8$ is an ester group can also be prepared from compounds of the formula 29 in which $COR^{53}$ is a carboxylic acid group by common esterification reactions like, for example, reacting the acid with an alcohol under acid catalysis, or alkylation of a salt of the carboxylic acid with an electrophile like an alkyl halogenide, or by transesterification from another ester. Compounds of the formula I in which a group $COR^8$ is an amide group can be prepared from amines and compounds of the formula 29 in which $COR^{53}$ is a carboxylic acid group or an ester thereof by common amination reactions. Especially for the preparation of amides the compounds of the formula 29 in which $COR^{53}$ is a carboxylic acid group can be condensed under standard conditions with compounds of the formula $HR^{8'}$ which are amines by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl) and many others.

If the residue -Q-$R^0$ present in an azaindole of the formula I or the residue $R^{54}$ present in an azaindole of the formula 29, or a residue in which functional groups within the residue -Q-$R^0$ or $R^{54}$ are present in protected form or in the form of a precursor group, have not already been introduced during a preceding step, for example during a synthesis of the azaindole nucleus, these residues can, for example, be introduced into the 1-position of the azaindole system by conventional literature procedures well known to one skilled in the art for N-alkylation, reductive amination, N-arylation, N-acylation or N-sulfonylation of ring nitrogen atoms of heterocycles. The starting azaindole derivative that is to be employed in such a reaction carries a hydrogen atom in the 1-position. N-Alkylation of a ring nitrogen atom can, for example, be performed under standard conditions, preferably in the presence of a base, using an alkylating compound of the formula LG-Q-$R^0$ or of the formula $R^{54}$-LG, wherein the atom in the group Q or in the group $R^{54}$ bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. LG may, for example, also be a hydroxy group which, in order to achieve the alkylation reaction, is activated by a conventional activating agent. For the preparation of compounds in which A is a direct linkage and an aromatic group is directly bonded to the 1-position of the azaindole system, conventional arylation procedures can be used. For example aryl fluorides like alkyl fluorobonzoates or 4-fluorophenyl methyl sulfones can be employed as arylating agents. Such processes are described, for example, By S. Stabler, Jahangir, Synth. Commun. 24 (1994) 123; I. Khanna, R. Weier, Y. Yu, X. Xu. F. Koszyk, J. Med. Chem. 40 (1997) 1634. Alternatively a wide variety of substituted aryl iodides, aryl bromides or aryl triflates can serve as arylating agents at the 1-position of the azaindole system in a copper salt or palladium mediated reaction according to R. Sarges, H. Howard, K. Koe, A. Weissmann, J. Med. Chem, 32 (1989) 437; P. Unangst, D. Connor, R. Stabler, R. Weikert, J. Heterocycl. Chem, 24 (1987) 811; G. Tokmakov, I. Grandberg, Tetrahedron 51 (1995) 2091; D. Old, M. Harris, S. Buchwald, Org. Lett. 2 (2000) 1403, G. Mann, J. Hartwig, M.

Driver, C. Fernandez-Rivas, J. Am. Chem. Soc. 120 (1998) 827; J. Hartwig, M. Kawatsura, S. Hauk, K. Shaughnessy, L. J. Org. Chem. 64 (1999) 5575. Moreover such arylations can also be accomplished by reaction of a wide range of substituted aryl boronic acids as demonstrated for example by W. Mederski, M. Lefort, M. Germann, D. Kux, Tetrahedron 55 (1999) 12757.

In the course of the synthesis the employment of microwave assistance for speeding-up, facilitating or enabling reactions may be beneficial or even required in many cases. Some reactions are for example described by J. L. Krstenansky, I. Cotteril, Curr. Opin. Drug. Disc. & Development, 4(2000), 454; P. Lidstrom, J. Tierney, B. Wathey, J. Westman, Tetrahedron, 57(2001), 9225; M. Larhed, A. Hallberg, Drug Discovery Today, 8 (2001) 406; S. Caddick, Tetrahedron, 51 (1995) 10403.

Preferred methods include, but are not limited to those described in the examples. The compounds of the present invention are serine protease inhibitors, which inhibit the activity of the blood coagulation enzyme factors Xa and/or factor VIIa In particular, they are highly active inhibitors of factor Xa. They are specific serine protease inhibitors inasmuch as they do not substantially inhibit the activity of other proteases whose inhibition is not desired. The activity of the compounds of the formula I can be determined, for example, in the assays described below or in other assays known to those skilled in the art. With respect to factor Xa inhibition, a preferred embodiment of the invention comprises compounds which have a Ki<1 mM for factor Xa inhibition as determined in the assay described below, with or without concomitant factor VIIa inhibition, and which preferably do not substantially inhibit the activity of other proteases involved in coagulation and fibrinolysis whose inhibition is not desired (using the same concentration of the inhibitor). The compounds of the invention inhibit factor Xa catalytic activity either directly, within the prothrombinase complex or as a soluble subunit, or indirectly, by inhibiting the assembly of factor Xa into the prothrombinase complex.

As inhibitors of factor Xa and/or factor VIIa the compounds of the formula I and their physiologically tolerable salts and their prodrugs are generally suitable for the therapy and prophylaxis of conditions in which the activity of factor Xa and/or factor VIIa plays a role or has an undesired extent, or which can favorably be influenced by inhibiting factor Xa and/or factor VIIa or decreasing their activities, or for the prevention, alleviation or cure of which an inhibition of factor Xa and/or factor VIIa or a decrease in their activity is desired by the physician. As inhibition of factor Xa and/or factor VIIa influences blood coagulation and fibrinolysis, the compounds of the formula I and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound I or a physiologically tolerable salt or a prodrug thereof, as well as pharmaceutical preparations therefor.

The present invention also relates to the compounds of the formula I and/or their physiologically tolerable salts and/or their prodrugs for use as pharmaceuticals (or medicaments), to the use of the compounds of the formula I and/or their physiologically tolerable salts and/or their prodrugs for the production of pharmaceuticals for inhibition of factor Xa and/or factor VIIa or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses. The invention also relates to the use of the compounds of the formula I and/or their physiologically tolerable salts and/or their prodrugs for the inhibition of factor Xa and/or factor VIIa or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formula I and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the present invention can also be used to reduce an inflammatory response. Examples of specific disorders for the treatment or prophylaxis of which the compounds of the formula I can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration. The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formula I and/or its (their) physiologically tolerable salts and/or its (their) prodrugs. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 mg to about 1000 mg, preferably from about 1 mg to about 500 mg.

In addition to the active ingredients of the formula I and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their physiologically tolerable salts and/or their prodrugs. In case a pharmaceutical preparation contains two or more compounds of the formula I, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or a physiologically tolerable salt and/or its prodrug, the pharmaceutical preparations can also contain one or more other therapeutically or prophylactically active ingredients.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formula I can also advantageously be used as an anticoagulant outside an individual. For example, an effective amount of a compound of the invention can be contacted with a freshly drawn blood sample to prevent coagulation of the blood sample. Further, a compound of the formula I or its salts can be used for diagnostic purposes, for example in in vitro diagnoses, and as an auxiliary in biochemical investigations. For example, a compound of the formula I can be used in an assay to identify the presence of factor Xa and/or factor VIIa or to isolate factor Xa and/or factor VIIa in a substantially purified form. A compound of the invention can be labeled with, for example, a radioisotope, and the labeled compound bound to factor Xa and/or factor VIIa is then detected using a routine method useful for detecting the particular label. Thus, a compound of the formula I or a salt thereof can be used as a probe to detect the location or amount of factor Xa and/or factor VIIa activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention our outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

| Abbreviations used: | |
|---|---|
| tert-Butyl | tBu |
| 2,2'-bis(diphenylphoshino-1,1'-binaphthyl | Binap |
| Bis-(oxo-3-oxazolidinyl)-phosphoryl chloride | BOP-Cl |
| dibenzylidenacetone | dba |
| Dichloromethane | DCM |
| Dicyclohexyl-carbodiimide | DCC |
| Diethylphosphoryl cyanide | DEPC |
| 4-Dimethyaminopyridine | DMAP |
| N,N-Dimethylformamide | DMF |
| Dimethylsulfoxide | DMSO |
| 1,1'-Bis(diphenylphosphino)ferrocene | DPPF |
| O-(7-Azabenzotriazol-1-yl)-N,N,N',N'-tetramethyluronium-hexafluorophosphate | HATU |
| N-Bromosuccinimide | NBS |
| N-Chlorosuccinimide | NCS |
| N-Iodosuccinimide | NIS |
| N-Ethylmorpholine | NEM |
| Methanol | MeOH |
| Room temperature 20° C. to 25° C. | RT |
| Saturated | sat. |
| Tetrahydrofuran | THF |
| Trifluoroacetic acid | TFA |
| O-((Ethoxycarbonyl)cyanomethyleneamino)-N,N,N',N'-tetramethyluronium tetrafluoroborate | TOTU |

Example 1

1-[5-(5-Chloro-thiophen-2-yl)-isoxazol-3-ylmethyl]-1H-pyrrolo[2,3-b]pyridine-2-carboxylic acid (1-isopropyl-piperidin-4-yl)-amide (i) 1H-Pyrrolo[2,3-b]pyridine-2-carboxylic acid methyl ester 0.495 g (1.64 mmol) of 1-benzenesulfonyl-1H-pyrrolo[2,3-b]pyridine-2-carboxylic acid was dissolved in 5 mL of methanol and 3 mL of 2N aqueous sodium hydroxide. The reaction was stirred at 40° C. for 8 h. The solvent was removed under reduced pressure. Residual volatiles were removed by twice codistilling with toluene. The residue was suspended in methanolic hydrochloric acid and stirred for 16 h at RT. The solvent was removed under reduced pressure. The residue was dissolved in ethyl acetate and washed with saturated aqueous sodium bicarbonate solution, and saturated aqueous sodium chloride solution. The organic phase was dried with sodium sulfate, filtered and the solvent was removed under reduced pressure.

Yield 0.201 g. MS (CI+): m/e=177 (M+H$^+$).

(ii) 1-[5-(5-Chloro-thiophen-2-yl)-isoxazol-3-ylmethyl]-1H-pyrrolo[2,3-b]pyridine-2-carboxylic acid 0.195 g (1.1 mmol) of 1H-pyrrolo[2,3-b]pyridine-2-carboxylic acid methyl ester was dissolved in 4 mL of DMF and 48.7 mg (1.2 mmol) of sodium hydride (60% in mineral oil) was added. The reaction was stirred at RT for 20 min, cooled to −78° C. then 324 mg (1.2 mmol) of 3-bromomethyl-5-(5-chloro-thiophen-2-yl)-isoxazole [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R; Lau, Wan F.; Poli, Gregory B; PCT Int. Appl. (2001) 460 pp. WO 0107436 A2] was added. The reaction was allowed to warm to RT overnight. 0.3 mL of 2N aqueous sodium hydroxide was added and the reaction was stirred at RT for 24 h. The product was purified by preparative RP-HPLC eluting with a gradient of 0-100% acetonitrile in water (+0.01% trifluoroacetic acid). After lyophilization the product was obtained as a solid.

Yield 280 mg. MS(TOF MS ES+): m/e=359 (M$^+$).

(iii) (1-Isopropyl-piperidin-4-yl)-carbamic acid tert-butyl ester

To a solution of 5.0 g Piperidin-4-yl-carbamic acid tert-butyl ester in 15 mL methanol, 7.34 mL acetone, 3.14 g Na(CN)BH$_3$ and 0.3 mL acetic acid were added. After stirring for 16 h at RT the solvent was removed under reduced pressure and the residue was partitioned between 30 mL of water and 30 mL of ethyl acetate. The organic layer was washed with saturated Na$_2$CO$_3$ solution, water and then dried over Na$_2$SO$_4$. Following filtration, the solvent was removed under reduced pressure to yields a white solid. Yield: 4.8 g MS (ES$^+$): m/e=243.

(iv) 1-Isopropyl-piperidin-4-ylamine

To 4.8 g (1-Isopropyl-piperidin-4-yl)-carbamic acid tert-butyl ester in 15 mL methanol, 20 mL methanolic hydrochloric acid (8M) were added and the mixture was stirred for 16 h. Removal of the solvent under reduced pressure yielded a white solid, which was coevaporated twice with 20 mL toluene. The product was obtained as its hydrochloride. Yield: 5.42 g MS (ES$^+$): m/e=143.

(v) 1-[5-(5-Chloro-thiophen-2-yl)-isoxazol-3-ylmethyl]-1H-pyrrolo[2,3-b]pyridine-2-carboxylic acid (1-isopropyl-piperidin-4-yl)-amide 0.135 g (0.4 mmol) of 1-[5-(5-Chloro-thiophen-2-yl)-isoxazol-3-ylmethyl]-1H-pyrrolo[2,3-b]pyridine-2-carboxylic acid, 0.432 g (3.8 mmol) of NEM and 135 mg (0.4 mmol) of TOTU were dissolved in 3 mL of DMF and stirred at RT for 20 min. 89 mg (0.4 mmol) of 1-Isopropyl-piperidin-4-ylamine dihydrochloride salt was added to the reaction solution and stirred at RT for 4 h. The product was purified by preparative RP-HPLC eluting with a gradient of 0-100% acetonitrile in water (+0.01% trifluoroacetic acid). After lyophilization the product was obtained as a solid.

Yield: 156 mg MS (TOF MS ES+): m/e=484 (M$^+$).

Example 2

1-[5-(5-Chloro-thiophen-2-yl)-isoxazol-3-ylmethyl]-2-(1-isopropyl-piperidin-4-ylcarbamoyl)-1H-pyrrolo[2,3-b]pyridine-5-carboxylic acid methyl ester (i) 6-Amino-nicotinic acid methyl ester To a solution of 10 g 6-Amino-nicotinic acid in 100 mL MeOH, 0.8 mL concentrated H$_2$SO$_4$ were added and the mixture was heated to 60° C. for 12 h. Then the reaction mixture was concentrated under reduced pressure. After addition of 50 mL ice water the mixture was brought to pH 8 by addition of K$_2$CO$_3$. The aqueous phase was extracted with ethyl acetate (3×100 ml) and the combined organic layers were dried over MgSO$_4$. Removal of the solvent yielded 5.5 g of the desired product which was subjected to the following reaction without further purification.

Yield: 5.5 g.

(ii) 6-Amino-5-iodo-nicotinic acid methyl ester

To 5 g 6-Amino-nicotinic acid methyl ester and 16.2 g Bis(pyridine)iodonium(I) tetrafluoroborate in 250 mL DCM, 7.6 mL Trifluoromethanesulfonic acid were added dropwise at 0° C. The mixture was stirred for 24 h at RT. Then additional 3.2 g Bis(pyridine)iodoniun(I) tetrafluoroborate and 1.5 mL Trifluoromethanesulfonic acid were added. After stirring for 2 h at RT the reaction mixture was concentrated under reduced pressure and then taken-up with concentrated aqueous Na$_2$SO$_3$ solution and brought to pH 8 with concentrated aqueous ammonia. The mixture was extracted with ethyl acetate (2×150 ml). The combined organic layers were washed with brine and then dried over MgSO$_4$. After filtration the solvent was removed under reduced pressure and the residue was codestilled with 100 mL toluene. Yield: 9.6 g.

(iii) 1H-Pyrrolo[2,3-b]pyridine-2,5-dicarboxylic acid 5-methyl ester

A solution of 5.6 g 6-Amino-5-iodo-nicotinic acid methyl ester, 5.3 g 2-Oxo-propionic acid, 11.1 g NEt$_3$, 4.2 g Triphenylphosphine and 1.1 g Pd(OAc)$_2$ in 100 mL DMF was heated under argon to 100° C. After 10 h the reaction mixture was concentrated under reduced pressure and the residue was stirred with 250 mL water for 1 h. The precipitated product was collected by filtration and washed with water. The crude product was subjected to the next reaction step without further purification.

Yield: 10 g.

(iv) 2-(1-Isopropyl-piperidin-4-ylcarbamoyl)-1H-pyrrolo[2,3-b]pyridine-5-carboxylic acid methyl ester To a solution of 9.5 g 1H-Pyrrolo[2,3-b]pyridine-2,5-dicarboxylic acid 5-methyl ester in 120 mL DMF and 23.9 mL NEt$_3$, 9.2 g 1-Isopropyl-piperidin-4-ylamine hydrochloride and 11 g BOP-Cl were added at RT and the mixture was stirred for 3 h. After addition of 20 mL of water the reaction mixture was extracted with ethyl acetate (3×150 ml). The combined organic layers were washed with brine (1×50 ml) and then dried over MgSO$_4$. After filtration the solvent was removed under reduced pressure and the residue was purified by chromatography on silica gel eluting with EtOAc/MeOH 9:7->EtOAc/MeOH/NH3(aq.) 6:4:0.04. The fractions containing the product were evaporated and codestilled with toluene. Yield: 7.2 g.

(v) 1-[5-(5-Chloro-thiophen-2-yl)-isoxazol-3-ylmethyl]-2-(1-isopropyl-piperidin-4-ylcarbamoyl)-1H-pyrrolo[2,3-b]pyridine-5-carboxylic acid methyl ester To a solution of 1.2 g 2-(1-Isopropyl-piperidin-4-ylcarbamoyl)-1H-pyrrolo[2,3-b]pyridine-5-carboxylic acid methyl ester in 20 mL DMF, 91 mg sodium hydride (95%) were added at 0° C. Then the reaction mixture was warmed to RT and stirred for 30 min. After cooling again to 0° C., 967 mg 3-Bromomethyl-5-(5-chloro-thiophen-2-yl)-isoxazole [prepared by adopting a procedure described by Ewing, William F.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001), 460 pp. WO 0107436 A2] were added and the mixture was stirred for 2 h at RT. Then 50 mL of water were added and the precipitate was collected by filtration to yield 630 mg pure product. The filtrate was concentrated under reduced pressure and the residue purified by preparative RP-HPLC eluting with a gradient of 0-100% acetonitrile in water (+0.01% trifluoroacetic acid). After lyophilization further 371 mg of product were obtained as a solid.

Yield: 1.0 g MS (ES$^+$): m/e=542, chloro pattern.

Example 3

1-[5-(5-Chloro-thiophen-2-yl)-isoxazol-3-ylmethyl]-2-(1-isopropyl-piperidin-4-ylcarbamoyl)-1H-pyrrolo[2,3-b]pyridine-5-carboxylic acid To a solution of 630 mg of 1-[5-(5-Chloro-thiophen-2-yl)-isoxazol-3-ylmethyl]-2-(1-isopropyl-piperidin-4-ylcarbamoyl)-1H-pyrrolo[2,3-b]pyridine-5-carboxylic acid methyl ester in 60 mL MeOH, 8.7 mL of a 1M aqueous NaOH solution were added. The reaction mixture was heated to 60° C. for 3 h. After cooling to RT 8.8 mL of a 1M aqueous HCl were added and the solvents were removed under reduced pressure. The residue was stirred with water/MeCN 2:1 and the precipitated product was collected by filtration.

Yield: 276 mg MS (ES$^+$): m/e=528, chloro pattern.

Example 4

1-[5-(5-Chloro-thiophen-2-yl)-isoxazol-3-ylmethyl]-1H-pyrrolo[2,3-b]pyridine-2,5-dicarboxylic acid 5-amide 2-[(1-isopropyl-piperidin-4-yl)-amide]

To a solution of 100 mg 1-[5-(5-Chloro-thiophen-2-yl)-isoxazol-3-ylmethyl]-2-(1-isopropyl-piperidin-4-ylcarbamoyl)-1H-pyrrolo[2,3-b]pyridine-5-carboxylic acid in 1 mL DMF, 62 mg TOTU, 0.2 mL DIPEA and 10 mg NH$_4$Cl were added at RT and stirred for 16 h. Then the sovent was removed under reduced pressure and the crude material purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 16 mg MS (ES$^+$): m/e=527, chloro pattern.

Example 5

1-[5-(5-Chloro-thiophen-2-yl)-isoxazol-3-ylmethyl]-1H-pyrrolo[3,2-b]pyridine-2-carboxylic acid (1-isopropyl-piperidin-4-yl)-amide (i) 1H-Pyrrolo[3,2-b]pyridine-2-carboxylic acid 1.22 mL 2-oxo-propionic acid, 0.26 g palladium acetate and 3.20 mL triethylamine were added to a solution of 1.00 g 2-bromo-pyridin-3-yl amine and 1.21 g triphenyl-phosphine in 10 mL N,N-dimethylformamide. The reaction mixture was stirred for 4 hours at 100° C. After removal of the solvent under reduced pressure, the residue was purified by column chromatography on silica gel with dichloromethane/methanol as eluent. Yield: 260 mg MS(ES$^+$): m/e=163.

1H-NMR (400 MHz, DMSO/TMS): δ=13.30 (s, 1H); 12.00 (s, 1H); 8.45 (d, 1H); 7.82 (d, 1H); 7.25 (dd, 1H); 7.14 (s, 1H).

(ii) 1H-Pyrrolo[3,2-b]pyridine-2-carboxylic acid methyl ester

A solution of 130 mg 1H-pyrrolo[3,2-b]pyridine-2-carboxylic acid in 5 mL of a 8 N solution of hydrochloric acid in methanol was stirred at 60° C. for 6 hours. Removal of the solvent under reduced pressure yielded a white solid, which was coevaporated twice with 5 mL toluene. The product was obtained as its hydrochloride. Yield: 150 mg MS(ES$^+$): m/e=177.

1H-NMR (400 MHz, DMSO/TMS): δ=13.60 (s, 1H); 8.86 (d, 1H); 8.59 (d, 1H); 7.82 (dd, 1H); 7.41 (s, 1H); 3.99 (s, 3H).

(iii) 1-[5-(5-Chloro-thiophen-2-yl)-isoxazol-3-ylmethyl]-1H-pyrrolo[3,2-b]pyridine-2-carboxylic acid methyl ester To a solution of 150 mg 1H-pyrrolo[3,2-b]pyridine-2-carboxylic acid methyl ester in 2 mL N,N-dimethylformamide 20.4 mg sodium hydride (95%) were added at 0° C. After stirring at 0° C. for 10 minutes 261 mg 3-bromoethyl-5-(5-chloror-thiophen-2-yl)-isoxazole were added. The reaction mixture was allowed to warm up to room temperature and stirred for 2 hours. After removing of the solvent under reduced pressure the residue was purified by chromatography on silica gel eluting with a dichloromethane/methanol gradient.

Yield: 80 mg MS(ES$^+$): m/e=374, chloro pattern.
1H-NMR (400 MHz, DMSO/TMS): δ=8.54 (d, 1H); 8.13 (d, 1H); 7.58 (d, 1H); 7.43 (s, 1H); 7.39 (dd, 1H); 7.26 (d, 1H); 7.73 (s, 1H); 5.98 (s, 2H); 3.90 (s, 3H).

(iv) 1-[5-(5-Chloro-thiophen-2-yl)-isoxazol-3-ylmethyl]-1H-pyrrolo[3,2-b]pyridine-2-carboxylic acid A solution of 75 mg 1H-pyrrolo[3,2-b]pyridine-2-carboxylic acid methyl ester and 9.6 mg lithium hydroxide in a mixture of 3 mL tetrahydrofuran and 1 mL water was stirred for 2 hours at room temperature. After acidifying with 6 N hydrochloric acid to pH 2 the solvent of the mixture was removed under reduced pressure. The resulting residue was purified by chromatography on silica gel eluting with a ethyl acetate/methanol gradient with 0.1% water.

Yield: 50 mg MS(ES$^+$): m/e=360, chloro pattern.
1H-NMR (400 MHz, DMSO/TMS): δ=8.45 (d, 1H); 7.84 (d, 1H); 7.53 (d, 1H); 7.22 (d, 1H); 7.15 (dd, 1H); 6.94 (s, 1H); 6.60 (s, 1H); 6.14 (s, 2H).

(v) 1-[5-(5-Chloro-thiophen-2-yl)-isoxazol-3-ylmethyl]-1H-pyrrolo[3,2-b]pyridine-2-carboxylic acid (1-isopropyl-piperidin-4-yl)-amide To a suspension of 50 mg 1-[5-(5-chloro-thiophen-2-yl)-isoxazol-3-ylmethyl]-1H-pyrrolo[3,2-b]pyridine-2-carboxylic acid, 36 mg 1-isopropyl-piperidin-4-ylamine hydrochloride and 35 mg bis(2-oxo-3-oxazolidinyl)phosphinic chloride in 1 mL dichloromethane, 77 μl triethylamine were added at room temperature and the mixture was stirred for 16 hours. After removing of the solvent under reduced pressure, the residue was purified by preparative HPLC (C18 reverse phase column, elution with a water/acetonitrile gradient with 0.1% trifluoroacetic acid). The fractions containing the product were evaporated and lyophilized to yield a white residue which was partitioned between 5 mL aqueous 0.1 N sodium hydroxide solution and 5 mL ethyl acetate.

The organic layer was washed with additional water and then dried over sodium sulphate. After filtration and removal of the solvent under reduced pressure, a white solid was obtained.

Yield: 10 mg MS(ES$^+$): m/e=484, chloro pattern. 1H-NMR (500 MHz, DMSO/TMS): δ=8.53 (d, 1H); 8.46 (d, 1H); 8.03 (d, 1H); 7.57 (d, 1H); 7.32 (s, 1H); 7.28 (dd, 1H); 7.26 (d, 1H); 6.65 (s, 1H); 5.93 (s, 2H); 3.75 (m, 1H); 2.80 (m, 2H); 2.70 (m, 1H); 2.17 (m, 2H); 1.80 (m, 2H); 1.53 (m, 2H); 0.96 (d, 6H)

Example 6

1-[5-(5-Chloro-thiophen-2-yl)-isoxazol-3-ylmethyl]-2-(1-isopropyl-piperidin-4-ylcarbamoyl)-1H-pyrrolo[3,2-b]pyridine-5-carboxylic acid (i) 5-Amino-6-bromo-pyridine-2-carboxylic acid methyl ester To a solution of 5.00 g 5-amino-pyridine-2-carboxylic acid methyl ester in 75 mL of a 48% aqueous solution of hydrobromic acid, 3.39 mL of a 32% aqeous solution of hydrogen peroxide were added. The mixture was stirred at room temperature for 2 hours, then additional 0.80 mL hydrogen peroxide solution were added. After stirring for 1 hour the reaction mixture was cooled down and brought to pH 8 by addition of concentrated aqueous ammonia. The mixture was extracted with 300 mL ethyl acetate. The aqueous layer was washed with additional ethyl acetate and then the combined organic phases were dried over sodium sulfate. After filtration the solvent was removed under reduced pressure and the residue was purified by chromatography on silica gel eluting with a n-heptane/ethyl acetate gradient. Yield: 2.83 g MS(ES$^+$): m/e=231.

1H-NMR (400 MHz, DMSO/TMS): δ=7.80 (d, 1H); 7.10 (d, 1H); 6.37 (s, 2H); 3.80 (s, 3H)

(ii) 1H-Pyrrolo[3,2-b]pyridine-2,5-dicarboxylic acid 5-methyl ester

The following compound was prepared in analogy to example 5 by using 5-amino-6-bromo-pyridine-2-carboxylic acid methyl ester instead of 2-bromo-pyridin-3-ylamine.

MS(ES$^+$): m/e=221. 1H-NMR (400 MHz, DMSO/TMS): δ=11.80 (s, 1H); 7.89 (d, 1H); 7.84 (d, 1H); 6.93 (s, 1H); 3.88 (s, 3H).

(iii) 2-(1-Isopropyl-piperidin-4-ylcarbamoyl)-1H-pyrrolo[3,2-b]pyridine-5-carboxylic acid methyl ester To a solution of 140 mg 1H-pyrrolo[3,2-b]pyridine-2,5-dicarboxylic acid 5-methyl ester in 1.4 mL N,N-dimethylformamide and 0.35 mL triethylamine, 164 mg 1-isopropyl-piperidin-4-ylamine hydrochloride and 161 mg bis(2-oxo-3-oxazolidinyl)phophinic chloride were added at room temperature and the mixture was stirred for 1 hour. After removing of the solvent under reduced pressure the residue was purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt.

Yield: 112 mg MS(ES$^+$): m/e=345. 1H-NMR (400 MHz, DMSO/TMS): δ=12.20 (s, 1H); 9.10 (s, 1H); 8.79 (d, 1H); 7.93 (m, 2H); 7.42 (s, 1H); 4.14 (m, 1H); 3.90 (s, 3H); 3.47 (m, 3H); 3.15 (m, 2H); 2.15 (m, 2H); 1.88 (m, 2H); 1.28 (d, 6H).

(iv) 1-[5-(5-Chloro-thiophen-2-yl)-isoxazol-3-ylmethyl]-2-(1-isopropyl-piperidin-4-ylcarbamoyl)-1H-pyrrolo[3,2-b]pyridine-5-carboxylic acid methyl ester To a solution of 60 mg 2-(1-isopropyl-piperidin-4-ylcarbamoyl)-1H-pyrrolo[3,2-b]pyridine-5-carboxylic acid methyl ester in 2 mL N,N-dimethylformamide, 4 mg sodium hydride (95%) were added at 0° C. After stirring at 0° C. for 10 minutes 53 mg 3-bromomethyl-5-(5-chloro-thiophen-2-yl)-isoxazole were added and the mixture was stirred for 2 hours at room temperature. After removing the solvent under reduced pressure the residue was purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt. Yield: 50 mg MS(ES$^+$): m/e=542, chloro pattern.

1H-NMR (400 MHz, DMSO/TMS): δ=8.93 (m, 2H); 8.25 (d, 1H); 8.04 (d, 1H); 7.55 (d, 1H); 7.42 (s, 1H); 7.28 (d, 1H); 6.69 (s, 1H); 5.97 (s, 2H); 4.07 (m, 1H); 3.91 (s, 3H); 3.45 (m, 2H); 3.10 (m, 2H); 2.10 (m, 3H); 1.83 (m, 2H); 1.25 (d, 6H).

(v) 1-[5-(5-Chloro-thiophen-2-yl)-isoxazol-3-ylmethyl]-2-(1-isopropyl-piperidin-4-ylcarbamoyl)-1H-pyrrolo[3,2-b]pyridine-5-carboxylic acid To a solution of 50 mg 1-[5-(5-chloro-thiophen-2-yl)-isoxazol-3-ylmethyl]-2-(1-isopropyl-piperidin-4-ylcarbamoyl)-1H-pyrrolo[3,2-b]pyridine-5-carboxylic acid methyl ester in 2 mL THF and 1 mL water 3.6 mg lithium hydroxide were added and the mixture was stirred at room temperature for 2 hours. Then the reaction mixture was acidified with 6 N hydrochloric acid to pH 3 and the solvent was removed under reduced pressure. The resulting residue was purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt.

Yield: 25 mg MS(ES+): m/e=528, chloro pattern. 1H-NMR (500 MHz, DMSO/TMS): δ=13.00 (s, 1H); 8.90 (m, 2H); 8.23 (d, 1H); 8.03 (d, 1H); 7.56 (d, 1H); 7.42 (s, 1H); 7.28 (d, 1H); 6.69 (s, 1H); 5.98 (s, 2H); 4.07 (m, 1H); 3.45 (m, 2H); 3.10 (m, 2H); 2.10 (m, 3H); 1.83 (m, 2H); 1.25 (d. 6H).

Example 7

1-[5-(5-Chloro-thiophen-2-yl)-isoxazol-3-ylmethyl]-5-oxo-4,5-dihydro-1H-pyrrolo[3,2-b]pyridine-2-carboxylic acid (1-isopropyl-piperidin-4-yl)-amide (i) 1-[5-(5-Chloro-thiophen-2-yl)-isoxazol-3-ylmethyl]4-oxy-1H-pyrrolo[3,2-b]pyridine-2-carboxylic acid methyl ester To a solution of 80 mg 1-[5-(5-Chloro-thiophen-2-yl)-isoxazol-3-ylmethyl]-1H-pyrrolo[3,2-b]pyridine-2-carboxylic acid methyl ester in 1 mL dichloromethane a solution of 52.8 mg 3-chloroperoxybenzoic acid (70%, wet with water) in 1 mL dichloromethane were added at 0° C. After stirring at 0° C. for 1 hour the reaction mixture was allowed to warm up to room temperature and stirred for 16 hours. The solution was washed with an aqueous 0.1 N solution of sodium hydroxide. The organic layer was washed with additional water and then dried over anhydrous sodium sulfate. After concentration under reduced pressure the residue was directly subjected to the subsequent reaction without further purification.

Yield: 100 mg MS(ES+): m/e=390, chloro pattern (ii) 1-[5-(5-Chloro-thiophen-2-yl)-isoxazol-3-ylmethyl]-5-oxo-4,5-dihydro-1H-pyrrolo[3,2-b]pyridine-2-carboxylic acid methyl ester A solution of 100 mg 1-[5-(5-Chloro-thiophen-2-yl)-isoxazol-3-ylmethyl]-4-oxy-1H-pyrrolo[3,2-b]pyridine-2-carboxylic acid methyl ester in 5 mL acetic anhydride was heated for 4 hours at 100° C. After cooling to room temperature the solvent of the mixture was removed under reduced pressure. After coevaporating twice with 5 mL toluene the residue was dissolved in 5 mL methanol and 17.6 mg potassium carbonate were added. The suspension was stirred for 16 hours at room temperature. After concentration under reduced pressure the residue was purified by preparative HPLC (C18 reverse phase column, elution with a water/acetonitrile gradient with 0.1% trifluoroacetic acid). The product was obtained as its trifluoroacetate salt.

Yield: 20 mg MS(ES+): m/e=390, chloro pattern. 1H-NMR (400 MHz, DMSO/TMS): δ=11.65 (s, 1H), 7.90 (d, 1H); 7.60 (d, 1H); 7.28 (d, 1H); 6.71 (s, 1H); 6.67 (s, 1H); 6.35. (d, 1H); 5.87 (s, 2H); 3.81 (s, 3H).

(iii) 1-[5-(5-Chloro-thiophen-2-yl)-isoxazol-3-ylmethyl]-5-oxo-4,5-dihydro-1H-pyrrolo[3,2-b]pyridine-2-carboxylic acid A solution of 20 mg) 1-[5-(5-Chloro-thiophen-2-yl)-isoxazol-3-ylmethyl]-5-oxo-4,5-dihydro-1H-pyrrolo[3,2-b]pyridine-2-carboxylic acid methyl ester and 1.9 mg lithium hydroxide in a mixture of 2 ml tetrahydrofuran and 1 mL water was stirred for 2 hours at room temperature. The solvent was removed under reduced pressure and the residue was coevaporated twice with toluene. The residue was directly subjected to the subsequent reaction without further purification.

Yield: 20 mg MS(ES+): m/e=376, chloro pattern.

(iv) 1-[5-(5-Chloro-thiophen-2-yl)-isoxazol-3-ylmethyl]-5-oxo-4,5-dihydro-1H-pyrrolo[3,2-b]pyridine-2-carboxylic acid (1-isopropyl-piperidin-4-yl)-amide To a suspension of 19.9 mg 1-[5-(5-chloro-thiophen-2-yl)-isoxazol-3-ylmethyl]-5-oxo-4,5-dihydro-1H-5-pyrrolo[3,2-b]pyridine-2-carboxylic acid and 13.5 mg bis(2-oxo-3-oxazolidinyl)phosphinic chloride in 1 mL dichloromethane 7.4 μl triethylamine were added at room temperature and the mixture was stirred for 2 hours. The reaction mixture was treated with 5 mL of a aqueous 0.1 N sodium hydroxide solution and washed with acetyl acetate. The organic layer was dried over anhydrous sodium sulfate. After filtration and removal of the solvent under reduced pressure the residue was dissolved in a mixture of 2 mL acetonitrile and 1 mL water. Lyophilization of the solution yielded a white solid.

Yield: 8 mg MS(ES+): m/e=500, chloro pattern. 1H-NMR (500 MHz, DMSO/MS): δ=11.70 (s, 1H); 8.36 (d, 1H); 7.83 (d, 1H); 7.59 (d, 1H); 7.28 (d, 1H); 6.76 (s, 1H); 6.63 (s, 1H); 6.22 (d, 1H); 5.85 (s, 2H); 3.68 (s, 1H); 2.78 (m, 2H); 2.68 (m, 1H); 2.14 (m, 2H); 1.75 (m, 2H); 1.51 (m, 2H); 0.98 (d, 6H).

Example 8

1-[5-(5-Chloro-thiophen-2-yl)-isoxazol-3-ylmethyl]-2-(3,4,5,6-tetrahydro-2H-[1,4']bipyridyl-4-ylcarbamoyl)-1H-pyrrolo[3,2-b]pyridine-5-carboxylic acid methyl ester (i) 2-(3,4,5,6-Tetrahydro-2H-[1,4']bipyridyl-4-ylcarbamoyl)-1H-pyrrolo[3,2-b]pyridine-5-carboxylic acid methyl ester To a solution of 450 mg 1H-pyrrolo[3,2-b]pyridine-2,5-dicarboxylic acid 5-methyl ester in 9 mL dichloromethane and 1.13 mL triethylamine, 614 mg 3,4,5,6-tetrahydro-2H-[1,4']bipyridyl-4-ylamine dihydrochloride and 520 mg bis(2-oxo-3-oxazolidinyl)phosphinic chloride were added at room temperature and the mixture was stirred for 2 hours. After treatment of the reaction mixture with 5 mL saturated aqueous solution of potassium carbonate the precipitate was collected by filtration and coevaporated twice with toluene. The residue was directly subjected to the subsequent reaction without further purification.

Yield: 300 mg MS(ES+): m/e=380. 1H-NMR (400 MHz, DMSO/TMS): δ=8.30 (m, 1H); 8.15 (d, 2H); 7.68 (m, 2H); 7.04 (s, 1H); 6.85 (d, 2H); 4.10 (m, 1H); 3.95 (m, 2H); 3.84 (s, 3H); 3.00 (m, 2H); 1.91 (m, 2H); 1.53 (m, 2H).

(ii) 1-[5-(5-Chloro-thiophen-2-yl)-isoxazol-3-ylmethyl]-2-(3,4,5,6-tetrahydro-2H-[1,4']bipyridyl-4-ylcarbamoyl)-1H-pyrrolo[3,2-b]pyridine-5-carboxylic acid methyl ester To a solution of 150 mg 2-(3,4,5,6-tetrahydro-2H-[1,4']bipyridyl-4-ylcarbamoyl)-1H-pyrrolo[3,2-b]pyridine-5-carboxylic acid methyl ester 2 mL N,N-dimethylformamide, 9.5 mg sodium hydride (96%) were added at 0° C. After stirring at 0° C. for 10 minutes 121 mg 3-bromomethyl-5-(5-chloro-thiophen-2-yl)-isoxazole were added and the mixture was stirred for 50 hours at room temperature. 2 mL water were added to the reaction mixture and the resulting precipitate was collected by filtration. The residue was dissolved in 2 mL N,N-dimethylformamide and purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt.

Yield: 27 mg MS(ES+): m/e=577, chloro pattern.

Example 9

1-[5-(5-Chloro-thiophen-2-yl)-isoxazol-3-ylmethyl]-2-(3,4,5,6-tetrahydro-2H-[1,4']bipyridyl-4-ylcarbamoyl)-1H-pyrrolo[3,2-b]pyridine-5-carboxylic acid To a solution of 35 mg 1-[5-(5-chloro-thiophen-2-yl)-isoxazol-3-ylmethyl]-2-(1-isopropyl-piperidin-4-ylcarbamoyl)-1H-pyrrolo[3,2-b]pyridine-5-carboxylic acid methyl ester in 0.5 mL tetrahydrofuran and 0.25 mL water 2.4 mg lithium hydroxide were added and the mixture was stirred at room temperature for 16 hours. After removing of the solvent under reduced pressure the resulting residue was purified by preparative HPLC (C18 reverse phase column, elution with a water/acetonitrile gradient with 0.1% trifluoroacetic acid). The fractions containing the product were evaporated and lyophilized to yield a white solid. The product was obtained as its trifluoroacetate salt.

Yield: 14.3 mg MS(ES+): m/e=563, chloro pattern. 1H-NMR (500 MHz, DMSO/TMS): δ=13.25 (s, 1H); 13.00 (s, 1H); 8.73 (d, 1H); 8.24 (m, 3H); 8.03 (d, 1H); 7.57 (d, 1H); 7.39 (s, 1H); 7.26 (m, 3H); 6.69 (s, 1H); 5.98 (s, 2H); 4.25 (m, 3H); 2.00 (m, 2H); 1.59 (m, 2H).

Example 10

1-[5-(5-Chloro-thiophen-2-yl)-isoxazol-3-ylmethyl]-5-(2-methoxy-ethoxy)-1H-pyrrolo[2,3-c]pyridine-2-carboxylic acid (1-isopropyl-piperidin-4-yl)-amide (i) 2-(2-Methoxy-ethoxy)-4-methyl-5-nitro-pyridine To 20 mL of 2-Methoxy-ethanol 243 mg of NaH (6.09 mmol, 60% suspension in oil) were added and the mixture was stirred for 15 min. in an argon atmosphere. 1 g (5.8 mmol) 2-Chloro-4-methyl-5-nitro-pyridine were added and the reaction mixture was stirred for 3 h at room temperature.

After addition of 40 mL water and methyl-tertbutyl ether, the phases were separated and the organic phase was washed with saturated NaHCO$_3$ solution and water and was dried over Na$_2$SO$_4$. After filtration, the solvent was removed in vacuo and the residue was purified by flash chromatography on silica gel using heptane/ethyl acetate=8/2. 2-(2-Methoxy-ethoxy)-4-methyl-5-nitro-pyridine was isolated as colourless oil. Yield: 0.73 g.

(ii) 3-[2-(2-Methoxy-ethoxy)-5-nitro-pyridin-4-yl]-2-oxo-propionic acid ethylester potassium salt To 265 mg (6.78 mmol) potassium in 20 mL absolute diethylether, 2.5 mL ethanol were slowly added. The mixture is cooled to 0° C. and a solution of 720 mg (3.39 mmol) 2-(2-Methoxy-ethoxy)-4-methyl-5-nitro-pyridine in 2.5 mL of absolute diethylether and 0.5 mL ethanol were added. 3.966 g (27.14 mmol) oxalic acid diethylester in 15 mL toluene were added tropwise over 45 min. The reaction mixture was stirred at room temperature for 4 h. The precipitate was filtered, washed with diethyl ether/n-heptane 1/1 and dried in vacuo. 1.4 g of 3-[2-(2-Methoxy-ethoxy)-5-nitro-pyridin-4-yl]-2-oxo-propionic acid ethylester potassium salt were isolated as a red solid and used in the next step without further purification.

(iii) 5-(2-Methoxy-ethoxy)-1H-pyrrolo[2,3-c]pyridine-2-carboxylic acid ethyl ester 0.8 mL of acidic acid was added to a solution of dried 3-[2-(2-Methoxy-ethoxy)-5-nitro-pyridin-4-yl]-2-oxo-propionic acid ethylester potassium salt in 20 mL methanol and the solution was hydrogenated using 199 mg of Pd(OH)$_2$ (20% on charcoal). After 3 h the mixture was concentrated and the residue distributed between saturated NaHCO$_3$ solution and ethyl acetate. The phases were separated and the organic phase was dried over MgSO$_4$. After filtration, the solvent was removed in vacuo the desired product as a pale yellow solid.

Yield: 660 mg.

(iv) 1-[5-(5-Chloro-thiophen-2-yl)-isoxazol-3-ylmethyl]-5-(2-methoxy-ethoxy)-1H-pyrrolo[2,3-c]pyridine-2-carboxylic acid ethyl ester 105 mg (4.16 mmol) NaH (96%) were added to a solution of 5-(2-Methoxy-ethoxy)-1H-pyrrolo[2,3-c]pyridine-2-carboxylic acid ethyl ester in 50 mL absolute DMF and the mixture was stirred for 30 min. at room temperature. 1.05 g (3.78 mmol) 3-Bromomethyl-5-(5-chloro-thiophen-2-yl)-isoxazole were added and the the mixture and stirring was continued for 3 h. After addition of 21 mg (0.832 mmol) NaH (96%) and 210 mg (0.756 mmol) 3-Bromomethyl-5-(5-chloro-thiophen-2-yl)-isoxazole and standing overnight the mixture was concentrated in vacuo. The residue was dissolved in CH$_2$Cl$_2$ and the solution washed with saturated NaHCO$_3$ solution. The solvent was removed in vacuo and the residue purified by flash chromatography over silica gel using n-heptane/ethyl acetate=3/2 as solvent. The fractions containing the product were concentrated.

Yield 1.3 g.

(v) 1-[5-(5-Chloro-thiophen-2-yl)-isoxazol-3-ylmethyl]-5-(2-methoxy-ethoxy)-1H-pyrrolo[2,3-c]pyridine-2-carboxylic acid To a solution of 1.3 g (2.814 mmol) 1-[5-(5-Chloro-thiophen-2-yl)-isoxazol-3-ylmethyl]-5-(2-methoxy-ethoxy)-1H-pyrrolo[2,3-c]pyridine-2-carboxylic acid ethyl ester in 30 mL THF and 15 mL MeOH 11.26 mL 1M LiOH solution were added and the mixture was stirred at 50° C. for 3 h. The organic solvents were removed in vacuo, 50 mL of water were added and the pH was adjusted to pH 2 with 1N HCl solution. The desired product precipitated and was filtered, washed with water and dried over P$_2$O$_5$. Yield 1.11 g.

(vi) 1-[5-(5-Chloro-thiophen-2-yl)-isoxazol-3-ylmethyl]-5-(2-methoxy-ethoxy)-1H-pyrrolo[2,3-c]pyridine-2-carboxylic acid (1-isopropyl-piperidin-4-yl)-amide hydrochloride To a solution of 1.11 g (2.55 mmol) 1-[5-(5-Chloro-thiophen-2-yl)-isoxazol-3-ylmethyl]-5-(2-methoxy-ethoxy)-1H-pyrrolo[2,3-c]pyridine-2-carboxylic acid and 0.55 g (2.55 mmol) 1-isopropyl-piperidin-4-ylamine dihydrochloride in 20 mL absolute DMF 837 mg (2.55 mmol) TOTU and 1.34 mL (7.67 mmol) DIPEA were added and the mixture was stirred at room temperature for 4 h. The solvent was removed in vacuo, the residue dissolved in CH$_2$Cl$_2$ and the CH$_2$Cl$_2$ phase washed with a saturated NaHCO$_3$ solution. The organic phase was concentrated and the residue purified by chromatography over silica gel using CH$_2$Cl$_2$/MeOH/HOAc/H$_2$O=90/10/1/1 as eluent. The fractions containing the product were combined and concentrated. The product was isolated as its hydrochloride salt by lyophilization using 2.5 equivalents of 1N HCl in H$_2$O/AcCN.

Yield 1.2 g MS (LC-MS-ES$^+$): m/e=558, chloro pattern.

Example 11

1-[5-(5-Chloro-thiophen-2-yl)-isoxazol-3-ylmethyl]-5-(2-hydroxy-ethoxy)-1H-pyrrolo[2,3-c]pyridine-2-carboxylic acid (1-isopropyl-piperidin-4-yl)-amide To a solution of 600 mg (1.01 mmol) of 1-[5-(5-Chloro-thiophen-2-yl)-isoxazol-3-ylmethyl]-5-(2-methoxy-ethoxy)-1H-pyrrolo[2,3-c]pyridine-2-carboxylic acid (1-isopropyl-piperidin-4-yl)-amide hydrochloride (example 10 (vi)) in 50 mL CH$_2$Cl$_2$ 2 mL (2.02 mmol) of a 1M solution of BBr$_3$ in CH$_2$Cl$_2$ were added. The mixture was stirred at room temperature for 6 h. After standing over night the solvent was removed in vacuo and the residue was purified by preparative HPLC (eluent: CH$_3$CN/H$_2$O/0.1% CF$_3$COOH). The fractions containing the product were combined and concentrated in vacuo. The residue was dissolved in CH$_2$Cl$_2$ an washed with 0.1N NaOH solution. The solvent was removed in vacuo and the residue lyophilized with 2.5 equivalents of 1N HCl yielding 464 mg (79%) of the hydrochloride salt of the desired product.

MS (LC-MS-ES$^+$): m/e=544, chloro pattern.

Example 12

1-[(5-Chloro-pyridin-2-ylcarbamoyl)-methyl]-5-(2-methoxy-ethoxy)-1H-pyrrolo[2,3-c]pyridine-2-carboxylic acid (1-isopropyl-piperidin-4-yl)-amide (i) 5-(2-Methoxy-ethoxy)-1H-pyrrolo[2,3-c]pyridine-2-carboxylic acid To a solution of 1 g (3.784 mmol) 5-(2-Methoxy-ethoxy)-1H-pyrrolo[2,3-c]pyridine-2-carboxylic acid ethyl ester (example 10 (iii)) in 50 mL THF and 25 mL MeOH 15.14 mL of a 1M LiOH solution were added. The mixture was stirred for 2 h at room temperature. The organic solvents were removed in vacuo, the solution acidified and concentrated in vacuo. The residue was purified by flash chromatography over silica gel using H$_2$Cl$_2$/MeOH/HOAc/H$_2$O=90/10/1/1 as eluent. The product fractions were combined, concentrated in vacuo and lyophilized.

Yield: 820 mg.

(ii) 5-(2-Methoxy-ethoxy)-1H-pyrrolo[2,3-c]pyridine-2-carboxylic acid (1-isopropyl-piperidin-4-yl)-amide To a solution of 820 mg (3.47 mmol) of 5-(2-Methoxy-ethoxy)-1H-pyrrolo[2,3-c]pyridine-2-carboxylic acid and 745 mg (3.47 mmol) 1-isopropyl-piperidin-4-ylamine dihydrochloride in 30 mL absolute DMF 1.13 g (3.47 mmol) TOTU and 1.81 mL (10.41 mmol) DIPEA were added and the mixture was stirred for 4 h at room temperature. The solvent was removed in vacuo, the residue dissolved in $CH_2Cl_2$ and the $CH_2Cl_2$ phase washed with a saturated $NaHCO_3$ solution. The organic phase was concentrated and the residue purified by chromatography over silica gel using $CH_2Cl_2$/MeOH/HOAc/$H_2O$=90/10/1/1 as eluent. The fractions containing the product were combined and concentrated. The residue was dissolved in $CH_2Cl_2$ and the $CH_2Cl_2$ phase was washed with a saturated $NaHCO_3$ solution. The phases were separated and the organic phase dried over $Na_2SO_4$. After filtration the solvent was removed in vacuo. Yield: 461 mg.

(iii) 2-Bromo-N-(5-chloro-pyridin-2-yl)-acetamide

To a solution of 5 g 5-Chloro-pyridin-2-ylamine and 1.5 mL pyridine in 30 mL toluene, 8 g bromo-acetyl bromide dissolved in 10 mL toluene was added dropwise under ice cooling. After 2 h the precipitate was isolated by filtration and recrystallized from toluene to yield a white solid.

Yield: 12 g.

(iv) 1-[(5-Chloro-pyridin-2-ylcarbamoyl)-methyl]-5-(2-methoxy-ethoxy)-1H-pyrrolo[2,3-c]pyridine-2-carboxylic acid (1-isopropyl-piperidin-4-yl)-amide To a solution of 461 mg (1.27 mmol) ) 5-(2-Methoxy-ethoxy)-1H-pyrrolo[2,3-c]pyridine-2-carboxylic acid (1-isopropyl-piperidin-4-yl)-amide in 20 mL absolute DMF 46 mg (1.91 mmol) NaH (96%) were added in an argon atmosphere. The mixture was stirred for 15 min. at room temperature. 479 mg (1.91 mmol) 2-Bromo-N-(5-chloro-pyridin-2-yl)-acetamide were added and the mixture stirred for 3 h at room temperature. The solvent was removed in vacuo, the residue dissolved in $CH_2Cl_2$ and the $CH_2Cl_2$ phase washed with $H_2O$ and dried over $Na_2SO_4$. After filtration, the organic phase was concentrated and the residue purified by chromatography over silica gel using $CH_2Cl_2$/MeOH/HOAc/$H_2O$=90/10/1/1 as eluent followed by preparative HPLC (eluent: $CH_3CN$/$H_2O$/0.1% $CF_3COOH$). The fractions containing the product were combined and concentrated in vacuo. The residue was lyophilized with 2 equivalents 1N HCl in a $H_2O$/$CH_3CN$ mixture yielding the hydrochloride salt of the desired product.

Yield: 545 mg MS (LC-MS-ES$^+$): m/e=529, chloro pattern.

Example 13

1-[(5-Chloro-pyridin-2-ylcarbamoyl)-methyl]-5-(2-hydroxy-ethoxy)-1H-pyrrolo[2,3-c]pyridine-2-carboxylic acid (1-isopropyl-piperidin-4-yl)-amide The compound was prepared as described in example 11. From 446 mg (0.789 mmol) of 1-[(5-Chloro-pyridin-2-ylcarbamoyl)-methyl]-5-(2-methoxy-ethoxy)-1H-pyrrolo[2,3-c]pyridine-2-carboxylic acid (1-isopropyl-piperidin-4-yl)-amide hydrochloride 286 mg of the desired product were obtained. MS (LC-MS-ES$^+$): m/e=515, chloro pattern.

Example 14

1-(6-Chloro-benzo[b]thiophen-2-ylmethyl)-5-(2-methoxy-ethoxy)-1H-pyrrolo[2,3-c]pyridine-2-carboxylic acid (1-isopropyl-piperidin-4-yl)-amide (i) 1-(6-Chloro-benzo[b]thiophen-2-ylmethyl)-5-(2-methoxy-ethoxy)-1H-pyrrolo[2,3-c]pyridine-2-carboxylic acid ethyl ester To a solution of 660 mg (2.497 mmol) 5-(2-Methoxy-ethoxy)-1H-pyrrolo[2,3-c]pyridine-2-carboxylic acid ethyl ester in 15 mL absolute DMF 24 mg (2.497 mmol) NaH (96%) were added in an argon atmosphere. The mixture was stirred for 30 min. at room temperature. 623 mg (2.497 mmol) 2-Bromomethyl-6-chloro-benzo[b]thiophene [prepared by adopting a procedure described by Ewing, William R. et al. in; PCT Int. Appl. (1999), 300 pp. WO 9937304 A1; and Ewing, William R. et al. PCT Int. Appl. (2001), 460 pp. WO 0107436 A2] were added and the mixture stirred for 1 h at room temperature. The solvent was removed in vacuo and the residue purified by preparative HPLC (eluent: $CH_3CN$/$H_2O$/0.1% $CF_3COOH$). The fractions containing the product were combined, concentrated in vacuo and lyophilized. Yield: 900 mg.

(ii) 1-(6-Chloro-benzo[b]thiophen-2-ylmethyl)-5-(2-methoxy-ethoxy)-1H-pyrrolo[2,3-c]pyridine-2-carboxylic acid 8 mL of a 1M LiOH solution in water were added to solution of 890 mg (2 mmol) 1-(6-Chloro-benzo[b]thiophen-2-ylmethyl)-5-(2-methoxy-ethoxy)-1H-pyrrolo[2,3-c]pyridine-2-carboxylic acid ethyl ester in 30 mL THF and 15 mL MeOH and the mixture was stirred for 1 h at 50° C. 16 mL of 1N HCl were added, the organic solvent removed in vacuo and the residue extracted with ethyl acetate. The organic phase was dried over $MgSO_4$. After filtration the solvent was evaporated yielding the desired product. Yield: 810 mg.

(iii) 1-(6-Chloro-benzo[b]thiophen-2-ylmethyl)-5-(2-methoxy-ethoxy)-1H-pyrrolo[2,3-c]pyridine-2-carboxylic acid (1-isopropyl-piperidin-4-yl)-amide To a solution of 800 mg (1.92 mmol) 1-(6-Chloro-benzo[b]thiophen-2-ylmethyl)-5-(2-methoxy-ethoxy)-1H-pyrrolo[2,3-c]pyridine-2-carboxylic acid and 413 mg (1.92 mmol) 1-isopropyl-piperidin-4-ylamine dihydrochloride in 20 mL absolute DMF 628 mg (1.92 mmol) TOTU and 1.0 mL (5.757 mmol) DIPEA were added and the mixture was stirred at room temperature for 1 h. The solvent was removed in vacuo and the residue purified by preparative HPLC (eluent: $CH_3CN$/$H_2O$/0.1% $CF_3COOH$) and chromatography over silica gel using $CH_2Cl_2$/MeOH/HOAc/$H_2O$=85/15/1.5/1.5 as eluent. The fractions containing the product were combined and concentrated. Yield 870 mg (69%), corresponding trifluoro acetate. 60 mg of the trifluoro acetate were lyophilized using 2.5 equivalents of 1N HCl in $H_2O$ and isolated as its hydrochloride salt.

MS (LC-MS-ES$^+$): m/e=541, chloro pattern.

Example 15

1-(6-Chloro-benzo[b]thiophen-2-ylmethyl)-5-(2-hydroxy-ethoxy)-1H-pyrrolo[2,3-c]pyridine-2-carboxylic acid (1-isopropyl-piperidin-4-yl)-amide To a solution of 810 mg (1.236 mmol) of 1-(6-Chloro-benzo[b]thiophen-2-ylmethyl)-5-(2-methoxy-ethoxy)-1H-pyrrolo[2,3-c]pyridine-2-carboxylic acid (1-isopropyl-piperidin-4-yl)-amide hydrochloride in 80 mL $CH_2Cl_2$ 2.472 mL of a 1M solution of $BBr_3$ in $CH_2Cl_2$ were added. The mixture was stirred at room temperature for 30 min. The solvent was removed in vacuo and lyophilized. The residue was purified by preparative HPLC (eluent: $CH_3CN/H_2O/$ 0.1% $CF_3COOH$). The fractions containing the product were combined, concentrated in vacuo and lyophilized with 2.5 equivalents of 1N HCl yielding the hydrochloride salt of the desired product.

Yield: 594 mg MS (LC-MS-ES$^+$): m/e=527, chloro pattern.

Pharmacological Testing

The ability of the compounds of the formula I to inhibit factor Xa or factor VIIa or other enzymes like thrombin, plasmin, or trypsin can be assessed by determining the concentration of the compound of the formula I that inhibits enzyme activity by 50%, i. e. the IC50 value, which was related to the inhibition constant Ki. Purified enzymes were used in chromogenic assays. The concentration of inhibitor that causes a 50% decrease in the rate of substrate hydrolysis was determined by linear regression after plotting the relative rates of hydrolysis (compared to the uninhibited control) versus the log of the concentration of the compound of formula I. For calculating the inhibition constant Ki, the IC50 value was corrected for competition with substrate using the formula $Ki=IC50/\{1+(\text{substrate concentration}/Km)\}$ wherein Km is the Michaelis-Menten constant (Chen and Prusoff, Biochem. Pharmacol. 22 (1973), 3099-3108; I. H. Segal, Enzyme Kinetics, 1975, John Wiley & Sons, New York, 100-125; which were incorporated herein by reference).

a) Factor Xa Assay

In the assay for determining the inhibition of factor Xa activity TBS-PEG buffer (50 mM Tris-HCl, pH 7.8, 200 mM NaCl, 0.05% (w/v) PEG-8000, 0.02% (w/v) NaN3) was used. The IC50 was determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N(α)-benzyloxycarbonyl-D-Arg-Gly-L-Arg-p-nitroanilide; Kabi Pharmacia, Inc.; Franklin, Ohio) in TBS-PEG.

The assay was performed by pre-incubating the compound of formula I plus enzyme for 10 min. Then the assay was initiated by adding substrate to obtain a final volume of 100 µl. The initial velocity of chromogenic substrate hydrolysis was measured by the change in absorbance at 405 nm using a Biotek Instruments kinetic plate reader (Ceres UV900HDi) at 25° C. during the linear portion of the time course (usually 1.5 min after addition of substrate). The enzyme concentration was 0.5 nM and substrate concentration was 140 µM.

b) Factor VIIa Assay

The inhibitory activity towards factor VIIa/tissue factor activity was determined using a chromogenic assay essentially as described previously (J. A. Ostrem et al., Biochemistry 37 (1998) 1053-1059 which was incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 µl human factor VIIa and TF (5 nM and 10 nM, respective final concentration) combined with 40 µl of inhibitor dilutions in 10% DMSO/TBS-PEG buffer (50 mM Tris, 15 mM NaCl, 5 mM CaCl2, 0.05% PEG 8000, pH 8.15). Following a 15 minutes preincubation period, the assay was initiated by the addition of 35 µl of the chromogenic substrate S-2288 (D-Ile-Pro-Arg-p-nitroanilide, Pharmacia Hepar Inc., 500 µM final concentration). The results (inhibition constants Ki (FXa) for inhibition of factor Xa) are shown in Table 1.

TABLE 1

| Example | Ki(FXa) [µM] |
|---------|--------------|
| 1 | 0.006 |
| 2 | 0.055 |
| 3 | 0.067 |
| 4 | 0.070 |
| 5 | 0.004 |
| 6 | 0.010 |
| 7 | 0.023 |
| 9 | 0.085 |
| 11 | 0.047 |
| 13 | 0.044 |

We claim:
1. A compound of formula I,

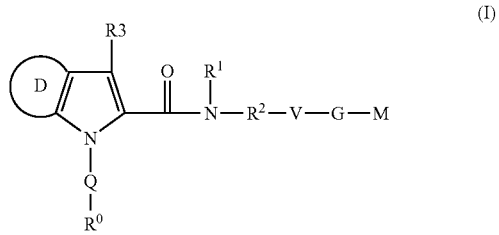

wherein
R$^0$ is
1) a monocyclic or bicyclic 6- to 14-membered aryl, wherein the aryl is mono-, di or trisubstituted independently of one another by R8,
2) pyridyl, which is unsubstituted or mono-, di- or trisubstituted independently of one another by R8, or
3) isoxazolyl, which is unsubstituted or mono-, di- or trisubstituted independently of one another by R8, and is additionally substituted by thienyl, wherein the thienyl is unsubstituted or mono-, di- or trisubstituted independently of one another by R8;
R8 is
1) halogen,
2) —NO$_2$,
3) —CN,
4) —C(O)—NH$_2$,
5) —OH,
6) —NH$_2$,
7) —O—CF$_3$, 8) a monocyclic or bicyclic 6- to 14-membered aryl, wherein the aryl is mono-, di- or trisubstituted independently of one another by halogen or —O—($C_1$-$C_8$)-alkyl,
9) —($C_1$-$C_8$)-alkyl, wherein the alkyl is unsubstituted or mono-, di- or trisubstituted independently of one another by halogen, $NH_2$, —OH or methoxy,
10) —O—($C_1$-$C_8$)-alkyl, wherein the alkyl is unsubstituted or mono-, di- or trisubstituted independently of one another by halogen, $NH_2$, —OH or methoxy,
11) —$SO_2$—$CH_3$ or
12) —$SO_2$—$CF_3$,
provided that when $R^0$ in a monocyclic or bicycle 6- to 14-membered aryl, then R8 is at least one halogen, —C(O)—$NH_2$ or —O—($C_1$-$C_8$)-alkyl;
the substructure

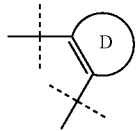

in formula I is pyridyl, and is unsubstituted or substituted 1, 2, 3, 4, 5 or 6 times by R3, or substituted 1 or 2 times by=O;
Q is a direct bond, —($C_0$-$C_2$)-alkylene-C(O)—$NR^{10}$—, —$NR^{10}$—C(O)—$NR^{10}$—, —$NR^{10}$—C(O)—, —$SO_2$—, —($C_1$-$C_6$)-alkylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$-$C_3$)-alkylene-O—($C_0$-$C_3$)-alkylene-, —($C_2$-$C_3$)-alkylene-S(O)—, —($C_2$-$C_3$)-alkylene-S(O)$_2$—, —$(CH_2)_m$—$NR^{10}$—C(O)—O—$(CH_2)_n$—, —($C_2$-$C_3$)-alkylene-S(O)$_2$—NH—($R^{10}$)—, —($C_2$-$C_3$)-alkylene-N($R^{10}$)— or —($C_0$-$C_3$)-alkylene-C(O)—O—$(CH_2)_m$—,
wherein —$(CH_2)_m$— or —$(CH_2)_n$— are alkylene that is unsubstituted or mono-, di- or trisubstituted independently of one another by halogen, —$NH_2$ or —OH, or —($C_3$-$C_6$)-cycloalkylene, which is unsubstituted or mono-, di- or trisubstituted independently of one another by halogen, —$NH_2$ or —OH;
$R^1$ is hydrogen, —($C_1$-$C_4$)-alkyl, wherein the alkyl is unsubstituted or substituted one to three times by R13, —($C_1$-$C_3$)-alkylene-C(O)—NH—$R^0$, —($C_1$-$C_3$)-alkylene-C(O)—O—$R^{15}$, a monocyclic or bicyclic 6- to 14-membered aryl, wherein the aryl is mono-, di- or trisubstituted independently of one another by R8; —($C_1$-$C_3$)-perfluoroalkylene, —($C_1$-$C_3$)-alkylene-S(O)—($C_1$-$C_4$)-alkyl, —($C_1$-$C_3$)-alkylene-S(O)$_2$—($C_1$-$C_3$)-alkyl, —($C_1$-$C_3$)-alkylene-S(O)$_2$—N($R^{4'}$)—$R^{5'}$, —($C_1$-$C_3$)-alkylene-O—($C_1$-$C_4$)-alkyl, or —($C_0$-$C_3$)-alkylene-($C_3$-$C_8$)-cycloalkyl;
$R^{4'}$ and $R^{5'}$ are independent of one another are identical or different and are hydrogen atom or —($C_1$-$C_4$)-alkyl;
$R^2$ is a direct bond or —($C_1$-$C_4$)-alkylene,
R14 is halogen, —OH, =O, —($C_1$-$C_8$)-alkyl, —($C_1$-$C_4$)-alkoxy, —$NO_2$, —C(O)—OH, —CN, —$NH_2$—C(O)—O—($C_1$-$C_4$)-alkyl, —($C_0$-$C_8$)-alkyl-$SO_2$—($C_1$-$C_4$)-alkyl, —($C_0$-$C_8$)-alkyl-$SO_2$—($C_1$-$C_3$)-perfluoroalkyl, —($C_0$-$C_8$)-alkyl-$SO_2$—N($R^{18}$)—$R^{21}$, —C(O)—NH—($C_1$-$C_8$)-alkyl, —C(O)—N—[($C_1$-$C_8$)-alkyl]$_2$, —$NR^{18}$—C(O)—NH—($C_1$-$C_8$)-alkyl, —C(O)—$NH_2$, —S—$R^{18}$, or —$NR^{18}$—C(O)—NH—[($C_1$-$C_8$)-alkyl]$_2$,
wherein $R^{18}$ and $R^{21}$ are independently from each other hydrogen, —($C_1$-$C_3$)-perfluoroalkyl or —($C_1$-$C_6$)-alkyl;
V is
2) a 6- to 14-membered aryl, wherein the aryl is unsubstituted or mono-, di- or trisubstituted independently of one another by R14, or
piperidinyl, pyridyl, imidazolyl, isothiazolyl, oxazolyl, pyrrolidinyl, tetrazolyl, or thiazolyl, each of which is unsubstituted of mono-, di- or trisubstituted independently of one another by R14;
G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— or —$(CH_2)_m$—$NR^{10}$—C(O)—O—$(CH_2)_n$—;
n and m are independently of one another identical or different and are the integers zero, 1, 2, 3, 4, 5 or 6;
M is
1) hydrogen,
2) —($C_1$-$C_8$)-alkyl, wherein the alkyl is unsubstituted or mono-, di- or trisubstituted independently of one another by R14,
3) —C(O)—N($R^{11}$)-$R^{12}$,
4) —$(CH_2)_m$—$NR^{10}$,
5) a 6- to 14-membered aryl, wherein the aryl is unsubstituted or mono-, di- or trisubstituted independently of one another by R14,
piperidinyl, pyridyl, imidazolyl, isothiazolyl, oxazolyl, pyrrolidinyl, tetrazolyl, or thiazolyl, each of which is unsubstituted or mono-, di or trisubstituted independently of one another by R14, or
7) —($C_3$-$C_8$)-cycloalkyl, wherein the cycloalkyl is unsubstituted or mono-, di- or trisubstituted independently of one another by R14
R3 is
1) hydrogen,
2) halogen,
3) —($C_1$-$C_4$)-alkyl, wherein the alkyl is unsubstituted or mono-, di- or trisubstituted independently of one another by R13,
4) —($C_1$-$C_3$)-perfluoroalkyl,
5) phenyl, wherein the phenyl is unsubstituted or mono-, di- or trisubstituted independently of one another by R13,
6) —($C_0$-$C_4$)-alkylene-O—R19,
7) —$NO_2$,
8) —CN,
9) —$SO_s$—$R^{11}$, wherein s is 1 or 2,
10) —$SO_t$—N($R^{11}$)—$R^{12}$, wherein t is 1 or 2,
11) —($C_0$-$C_4$)-alkylene-C(O)—$R^{11}$,
12) —($C_0$-$C_4$)-alkylene-C(O)—O—$R^{11}$,
13) —($C_0$-$C_4$)-alkylene-C(O)—N($R^{11}$)—$R_{12}$,
14) —($C_0$-$C_4$)-alkylene-N($R^{11}$)—$R^{12}$,
15) —$NR^{10}$—$SO_2$—$R^{10}$,
16) —S—$R^{10}$, 17) —(C₀-C₂)alkylene-C(O)—O—(C₂-C₄)-alkylene-O—C(O)—(C₁-C₄)-alkyl,
18) —C(O)—O—C(R15, R16)-O—C(O)—R17,
19) —(C₀-C₂)alkylene-C(O)—O—(C₂-C₄)-alkylene-O—C(O)—O—(C₁-C₆)-alkyl,
20) —C(O)—O—C(R15, R16)-O—C(O)—O—R17,
21) —(C₀-C₄)-alkylene-(C₆-C₁₄)-aryl, wherein aryl is mono-, di- or trisubstituted independently of one another by R13,
23) —(C₀-C₄)-alkylene-(C₃-C₈)-cycloalkyl, wherein the cycloalkyl is unsubstituted or mono-, di- or trisubstituted independently of one another by R13,
25) —(C₀-C₄)-alkylene-O—CH₂—(C₁-C₃)-perfluoroalkylene-CH₂—O—(C₀-C₄)-alkyl,
26) —SO_w—N(R¹¹)—R¹³, wherein w is 1 or 2,
27) —(C₀-C₄)-alkylene-C(O)—N(R¹¹)—R¹³,
28) —(C₀-C₄)-alkylene-N(R¹¹)—R¹³, or
29) a residue selected from the group consisting of

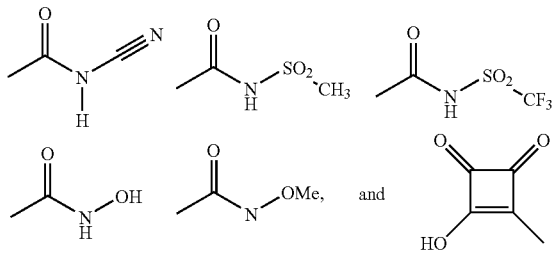

wherein Me is methyl;
R19 is
  a) hydrogen,
  b) —(C₁-C₄)-alkyl, wherein the alkyl is unsubstituted or mono-, di- or trisubstituted independently of one another by halogen, —NO₂, —CN, =O, —OH, —CF₃, —C(O)—O—R¹⁰, —C(O)—N(R¹⁰)—R²⁰, —N(R¹⁰)—R²⁰, —(C₀-C₃)-alkylene-O—R¹⁰, —Si—(CH₃)₃, —N(R¹⁰)—S(O)_u—R¹⁰, wherein u is 1 or 2, —S—R¹⁰, —SO_r—R¹⁰, wherein r is 1 or 2, —S(O)_v—N(R¹⁰)—R²⁰, wherein v is 1 or 2, —C(O)—R¹⁰, —(C₁-C₈)-alkyl, —(C₁-C₈)-alkoxy, phenyloxy-, —O—CF₃, —(C₀-C₄)-alkyl-C(O)—O—C(R15, R16)-O—C(O)—R17, —(C₁-C₄)-alkoxy-phenyl, —(C₀-C₄)-alkyl-C(O)—O—C(R15, R16)-O—C(O)—O—R17, —(C₁-C₃)-perfluoroalkyl, —O—R15, —NH—C(O)—NH—R¹⁰, —NH—C(O)—O—R¹⁰ or a residue selected from the group consisting of

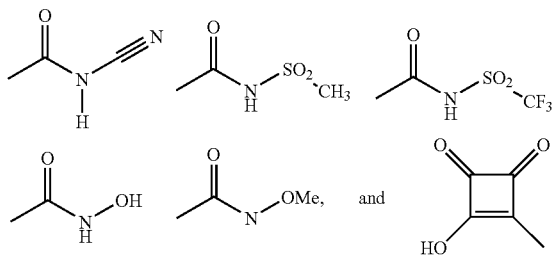

wherein Me is methyl,
  c) —CF₃, or
  d) —CHF₂—

R11 and R12 are independently of one another identical or different and are
  1) hydrogen,
  2) —(C₁-C₆)-alkyl, wherein the alkyl is unsubstituted or mono-, di- or trisubstituted independently of one another by R13,
  3) —(C₀-C₆)-alkyl-(C₃-C₈)-cycloalkyl,
  4) —SO_t—R¹⁰, wherein t is 1 or 2,
  5) —(C₀-C₆)-alkyl-(C₆-C₁₄)-aryl, wherein the alkyl and aryl independently from one another are unsubstituted or mono-, di- or trisubstituted by R13,
  6) —(C₁-C₃)-perfluoroalkyl, or
  7) —O—R¹⁷,
R13 is halogen, —NO₂, —CN, =O, —OH, —CF₃, —C(O)—O—R¹⁰, —C(O)—N(R¹⁰)—R²⁰, —N(R¹⁰)—R²⁰, —(C₃-C₈)-cycloalkyl, —(C₀-C₃)-alkylene-O—R¹⁰, —Si—(CH₃)₃, —N(R¹⁰)—S(O)_u—R¹⁰, wherein u is 1 or 2, —S—R¹⁰, —SO_r—R¹⁰, wherein r is 1 or 2, —S(O)_v—N(R¹⁰)—R²⁰, wherein v is 1 or 2, —C(O)—R¹⁰, —(C₁-C₈)-alkyl, —(C₁-C₈)-alkoxy, phenyl, phenyloxy-, —O—CF₃, —(C₀-C₄)-alkyl-C(O)—O—C(R15, R16)-O—C(O)—R17, —(C₁-C₄)-alkoxy-phenyl, —(C₀-C₄)-alkyl-C(O)—O—C(R15, R16)-O—C(O)—O—R17, —(C₁-C₃)-perfluoroalkyl, —O—R15, —NH—C(O)—NH—R¹⁰, —NH—C(O)—O—R¹⁰ or a residue selected from the group consisting of

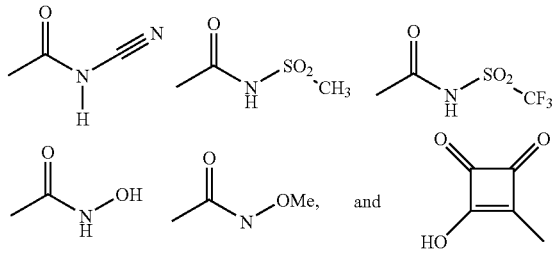

wherein Me is methyl;
R¹⁰ and R²⁰ are independently of one another hydrogen, —(C₁-C₆)-alkyl, —(C₀-C₄)-alkyl-OH, —(C₀-C₄)-alkyl-O—(C₁-C₄)-akyl or —(C₁-C₃)-perfluoroalkyl;
R15 and R16 are independently of one another hydrogen, —(C₁-C₆)-alkyl, or together with the carbon atom to which they are bonded form a 3- to 6 membered carbocyclic ring which is unsubstituted or substituted one to three times by R¹⁰' and
R17 is —(C₁-C₆)-alkyl, —(C₁-C₆)-alkyl-OH, —(C₁-C₆)-alkyl-O—(C₁-C₆)-alkyl, —(C₃-C₈)-cycloalkyl, —(C₁-C₆)-alkyl-O—(C₁-C₈)-alkyl-(C₃-C₈)-cycloalkyl, —(C₁-C₆)-alkyl-(C₃-C₈)-cycloalkyl, wherein the cycloalkyl is unsubstituted or substituted one, two or three times by —OH, —O—(C₁-C₄)-alkyl or R¹⁰;
or a stereoisomer or a mixture of stereoisomers thereof in any ratio, or a physiologically acceptable salt thereof.

2. The compound according to claim 1, wherein R⁰ as
  1) is phenyl, naphthyl, biphenylyl, anthryl or fluorenyl, each of which is mono-, di- or trisubstituted independently of one another by R8, or
  3) is isoxazolyl, which is unsubstituted or mono-, di- or trisubstituted independently of one another by R8, and is additionally substituted by thienyl, wherein the thienyl is unsubstituted or mono-, di- or trisubstituted independently of one another by R8;

R¹ as a monocyclic or bycyclic 6- to 14-membered ary is phenyl, naphthyl, biphenylyl, anthryl or fluorenyl, each of which is mono-, di- or trisubstituted independently of one another by R8

V is 2) phenyl, naphthyl, biphenylyl, anthryl or fluorenyl, each of which is mono-, di- or trisubstituted independently of one another by R14, or imidazolyl, isothiazolyl, oxazolinyl, piperindinyl, pyridyl, pyrrolidinyl, tetrazolyl, or thiazolyl, each of which is mono-, di- or trisubstituted independently of one another by R14;

R3 as 25) is —($C_0$-$C_3$)-alkylene-O—$CH_2$—($C_1$-$C_3$)-perfluoroalkylene-$CH_2$-O—($C_0$-$C_3$)-alkyl;

R15 and R16 are independently of one another hydrogen, or —($C_1$-$C_6$)-alkyl, or together with the carbon atom to which they are bonded form cyclopropyl, cyclobutyl, cyclopentyl or cyclohexyl, wherein each ring is unsubstituted or substituted one to three times by $R^{10}$; and R17 is —($C_1$-$C_6$)-alkyl, —($C_1$-$C_6$)-alkyl-OH, —($C_1$-$C_6$)-alkyl-O—($C_1$-$C_6$)-alkyl, —($C_1$-$C_6$)-alkyl-O—($C_1$-$C_8$)-alkyl-($C_3$-$C_8$)-cycloalkyl, —($C_0$-$C_6$)-alkyl-($C_3$-$C_8$)-cycloalkyl, wherein the cycloalkyl is unsubstituted or substituted one, two or three times by —OH, —O—($C_1$-$C_4$)-alkyl or $R^{10}$.

or a stereoisomer or a mixture of stereoisomers thereof in any ratio, or a physiologically acceptable salt thereof.

3. The compound according to claim 1, wherein
R⁰ as
1) is phenyl, naphthyl, biphenyl, anthryl or fluorenyl, each of which is mono-, di- or trisubstituted independently of one another by R8, or
3) is isoxazolyl, which is additionally substituted by thienyl, wherein the thienyl is unsubstituted or mono-, di- or trisubstituted independently of one another by R8;

R8 as
1) is fluorine, chlorine or bromine,
provided R8 is at least one halogen, —C(O)—$NH_2$ or —O—($C_1$-$C_8$)-alkyl residue;

substructure D is pyridyl, and is unsubstituted or substituted 1, 2, 3 or 4 times by R3, or is substituted 1 or 2 times by =O;

Q is a direct bond, —($C_0$-$C_2$)-alkylene-C(O)—$NR^{10}$—, —$NR^{10}$—C(O)—$NR^{10}$—, —$NR^{10}$—C(O)—, —$SO_2$— or —($C_1$-$C_6$)-alkylene;

R¹ is hydrogen, —($C_1$-$C_4$)-alkyl, wherein the alkyl is unsubstituted or substituted one to three times by R13, —($C_1$-$C_3$)-alkylene-C(O)—NH—R⁰, —($C_1$-$C_3$)-alkylene-C(O)—O—R15, —($C_1$-$C_3$)-perfluoroalkylene, —($C_1$-$C_3$)-alkylene-S(O)—($C_1$-$C_4$)-alkyl, —($C_1$-$C_3$)-alkylene-S($O)_2$—($C_1$-$C_3$)-alkyl, —($C_1$-$C_3$)-alkylene-S$(O)_2$—N($R^{4'}$)—$R^{5'}$, —($C_1$-$C_3$)-alkylene-O—($C_1$-$C_4$)-alkyl, or —($C_0$-$C_3$)-alkylene-($C_3$-$C_8$)-cycloalkyl, V is
2) phenyl, wherein the phenyl is unsubstituted or mono-, di- or trisubstituted independently of one another by R14, or
3) imidazole, isothiazole, oxazole, piperidine, pyridine, pyrrolidine, tetrazole, or thiazole, each of which is unsubstituted or mono-, di- or trisubstituted independently of one another by R14;

M is
1) hydrogen,
2) —($C_1$-$C_8$)-alkyl, wherein the alkyl is unsubstituted or mono-, di- or trisubstituted independently of one another by R14,
3) —C(O)—N(R11)-R12,
4) —$(CH_2)_m$—$NR^{10}$,
5) phenyl or naphthyl, wherein the phenyl or naphthyl is unsubstituted or mono-, di- or trisubstituted independently of one another by R14,
6) imidazole, isothiazole, oxazole, piperidine, pyridine, pyrrolidine, tetrazole, or thiazole, each of which is unsubstituted or mono-, di- or trisubstituted independently of one another by R14, or
7) —($C_3$-$C_8$)-cycloalkyl, wherein the cycloalkyl is unsubstituted or mono-, di- or trisubstituted independently of one another by R14;

R3 is
1) hydrogen,
2) halogen,
3) —($C_1$-$C_4$)-alkyl, wherein the alkyl is unsubstituted or mono-, di- or trisubstituted independently of one another by R13,
4) —($C_1$-$C_3$)-perfluoroalkyl,
5) phenyl, wherein the phenyl is unsubstituted or mono-, di- or trisubstituted independently of one another by R13,
6) —($C_0$-$C_4$)-alkylene-O—R19,
8) —CN,
9) —$SO_s$—$R^{11}$, wherein s is 1 or 2,
10) —$SO_t$—N($R^{11}$)—$R^{12}$, wherein t is 1 or 2,
11) —($C_0$-$C_4$)-alkylene-C(O)—$R^{11}$,
12) —($C_0$-$C_4$)-alkylene-C(O)—O—$R^{11}$,
13) —($C_0$-$C_4$)-alkylene-C(O)—N($R^{11}$)—$R^{12}$,
14) —($C_0$-$C_4$)-alkylene-N($R^{11}$)—$R^{12}$,
15) —$NR^{10}$—$SO_2$—$R^{10}$,
17) —($C_0$-$C_2$)-alkylene-C(O)—O—($C_2$-$C_4$)-alkylene-O—C(O)—($C_1$-$C_4$)-alkyl,
18) —C(O)—O—C(R15, R16)-O—C(O)—R17,
19) —($C_0$-$C_2$)-alkylene-C(O)—O—($C_2$-$C_4$)-alkylene-O—C(O)—O—($C_1$-$C_6$)-alkyl,
20) —C(O)—O—C(R15, R16)-O—C(O)—O—R17,
21) —($C_0$-$C_4$)-alkylene-($C_6$-$C_{14}$)-aryl, wherein aryl is as defined above and is mono-, di- or trisubstituted independently of one another by R13,
23) —($C_0$-$C_4$)-alkylene-($C_3$-$C_8$)-cycloalkyl, wherein cycloalkyl is unsubstituted or mono-, di- or trisubstituted independently of one another by R13,
25) —($C_0$-$C_3$)-alkylene-O—$CH_2$—$CF_2$—$CH_2$—O—($C_0$-$C_3$)-alkyl, —($C_0$-$C_3$)-alkylene-O—$CH_2$—$CF_2$—$CF_2$—$CH_2$—O—($C_0$-$C_3$)-alkyl, or —($C_0$-$C_3$)-alkylene-O—$CH_2$—($C_1$-$C_3$)-perfluoroalkylene-$CH_2$—OH,
26) —$SO_w$—N($R^{11}$)—$R^{13}$, wherein w is 1 or 2,
27) —($C_0$-$C_4$)-alkylene-C(O)—N($R^{11}$)—$R^{13}$,
28) —($C_0$-$C_4$)-alkylene-N($R^{11}$)—$R^{13}$, or
29) a residue selected from the group consisting of

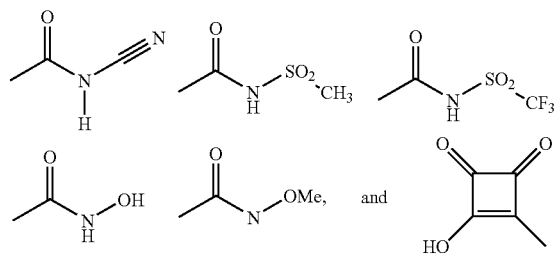

wherein Me is methyl,
R11 and R12 are independently of one another identical or different and are 1) hydrogen,
2) —(C$_1$-C$_6$)-alkyl, wherein the alkyl is unsubstituted or mono-, di- or trisubstituted independently of one another by R13,
5) —(C$_0$-C$_6$)-alkyl-(C$_6$-C$_{14}$)-aryl, wherein the alkyl and aryl are independently from one another unsubstituted or mono-, di- or trisubstituted by R13, or
7) —O—R$^{17}$ R13 is fluorine, chlorine, bromine, iodine, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_0$-C$_3$)-alkylene-O—R$^{10}$, —Si—(CH$_3$)$_3$, —N(R$^{10}$)—S(O)$_2$—R$^{10}$, —S—R$^{10}$, —SO$_2$—R$^{10}$, —S(O)$_2$—N(R$^{10}$)—R$^{20}$, —C(O)—R$^{10}$, —(C$_1$-C$_8$)-alkyl, —(C$_1$-C$_8$)-alkoxy, phenyl, phenyloxy-, —O—CF$_3$, —(C$_1$-C$_3$)-perfluoroalkyl, —(C$_0$-C$_4$)-alkyl-C(O)—O—C(R15, R16)-O—C(O)—R17, —(C$_1$-C$_4$)-alkoxy-phenyl, —(C$_0$-C$_4$)-alkyl-C(O)—O—C(R15, R16)-O—C(O)—O—R17, —O—R15, —NH—C(O)—NH—R$^{10}$, —NH—C(O)—O—R$^{10}$, or a residue selected from the group consisting of

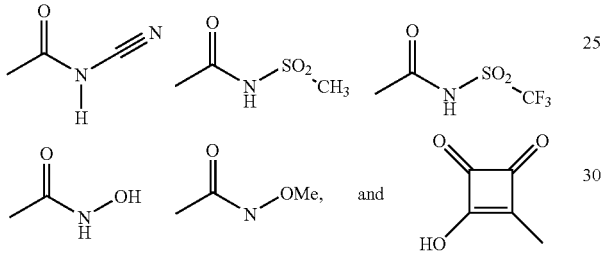

wherein Me is methyl;
R15 and R16 are independently of one another hydrogen, —(C$_1$-C$_6$)-alkyl, or together form cyclopropyl, cyclobutyl, cyclopentyl or cyclohexyl, wherein each ring is unsubstituted or substituted one to three times by R$^{10}$; and
R17 is —(C$_1$-C$_6$)-alkyl, —(C$_1$-C$_6$)-alkyl —OH, —(C$_1$-C$_6$)-alkyl-O—(C$_1$-C$_6$)-alkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein the cycloalkyl is unsubstituted or substituted one, two or three times by —OH, —O—(C$_1$-C$_4$)-alkyl or R$^{10}$, or a stereoisomer or a mixture of stereoisomers thereof in any ration, or a physiologically acceptable salt thereof.

4. The compound according claim 1, wherein
R0 as
1) is phenyl, wherein phenyl is unsubstituted or mono-, di- or trisubstituted independently of one another by R8, or
3) is isoxazolyl, which is unsubstituted or mono-, di- or trisubstituted independently of one another by R8, and in addition is substituted by thienyl, 2-thienyl, or 3-thienyl, each of which is unsubstituted or mono-, di- or trisubstituted independently of one another by R8;
R8 is
1) F, Cl, Br or I,
4) —C(O)—NH$_2$,
9) —(C$_1$-C$_4$)-alkyl, wherein the alkyl is unsubstituted or mono-, di- or trisubstituted independently of one another by halogen, —OH or methoxy, or
10) —O—(C$_1$-C$_4$)-alkyl, wherein the alkyl is unsubstituted or mono-, di- or trisubstituted independently of one another by halogen or methoxy, provided that R8 is at least one halogen, —C(O)—NH$_2$ or —O—(C$_1$-C$_8$)-alkyl;
substructure D is pyridyl, and is unsubstituted or substituted 1, 2, 3 or 4 times by R3, or is substituted 1 or 2 times by =O;
Q is a direct bond, —C(O)—, —SO$_2$— or —(C$_1$-C$_6$)-alkylene, —(C$_0$-C$_2$)-alkylene-C(O)—NR$^{10}$—;
R$^1$ is hydrogen, —(C$_1$-C$_2$)-alkyl, —(C$_1$-C$_3$)-alkylene-C(O)—NH—R$^0$, —(C$_1$-C$_3$)-perfluoroalkylene, —(C$_1$-C$_3$)-alkylene-C(O)—O—R$^{15}$, —(C$_1$-C$_3$)-alkylene-S(O)$_2$—(C$_1$-C$_3$)-alkyl or —(C$_1$-C$_3$)-alkylene-S(O)$_2$—N(R$^{4'}$)—R$^{5'}$, wherein R$^{4'}$ and R$^{5'}$ independently of one another are hydrogen atom or —(C$_1$-C$_4$)-alkyl,
R$^2$ is a direct bond or —(C$_1$-C$_2$)-alkylene,
R14 is fluorine, chlorine, —OH, =O, —(C$_1$-C$_8$)-alkyl, —C(O)—OH, —CN, —NH$_2$, —C(O)—O—(C$_1$-C$_4$)-alkyl, —C(O)—NH—(C$_1$-C$_8$)-alkyl, —C(O)—N—[(C$_1$-C$_8$)-alkyl]$_2$, —C(O)—NH$_2$ or —N(R$^{18}$)—R$^{21}$, wherein R$^{18}$ and R$^{21}$ are independently from each other hydrogen, —(C$_1$-C$_3$)-perfluoroalkyl or —(C$_1$-C$_4$)-alkyl;
V is
2) phenyl, wherein the phenyl is unsubstituted or mono-, di- or trisubstituted independently of one another by R14, or
3) pyrrolidine, imidazole, tetrazole, pyridine, piperidine, oxazole, thiazole, or isothiazole, each of which is unsubstituted or mono-, di- or trisubstituted independently of one another by R14;
G is a direct bond, —(CH$_2$)$_m$—, or —(CH$_2$)$_m$—NR$^{10}$—;
m is zero, 1, 2, 3 or 4;
M is
1) hydrogen,
2) —(C$_1$-C$_6$)-alkyl, wherein the alkyl is unsubstituted or mono-, di- or trisubstituted independently of one another by R14,
3) —C(O)—N(R$^{11}$)—R$^{12}$,
6) imidazole, isothiazole, oxazole, piperidine, pyridine, pyrrolidine, tetrazole, or thiazole, each of which is unsubstituted or mono-, di- or trisubstituted independently of one another by R14, or
7) (C$_3$-C$_6$)-cycloalkyl;
R3 is
1) hydrogen,
2) halogen,
3) —(C$_1$-C$_4$)-alkyl, wherein the alkyl is unsubstituted or mono-, di- or trisubstituted independently of one another by R13,
4) —(C$_1$-C$_3$)-perfluoroalkyl,
5) phenyl, wherein the phenyl is unsubstituted or mono-, di- or trisubstituted independently of one another by R13,
6) —(C$_0$-C$_4$)-alkylene-O—R19,
8) —CN,
8) —NR$^{10}$—SO$_2$—R$^{10}$,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
17) —(C$_0$-C$_2$)alkylene-C(O)—O—(C$_2$-C$_4$)-alkylene-O—C(O)—(C$_1$-C$_4$)-alkyl,
18) —C(O)—O—C(R15, R16)-O—C(O)—R17,
19) —(C$_0$-C$_2$)alkylene-C(O)—O—(C$_2$-C$_4$)-alkylene-O—C(O)—O—(C$_1$-C$_6$)-alkyl, 20) —C(O)—O—C(R15, R16)-O—C(O)—O—R17,
25) —(C$_0$-C$_3$)-alkylene-O—CH$_2$—CF$_2$—CH$_2$—O—(C$_0$-C$_3$)-alkyl, —(C$_0$-C$_3$)-alkylene-O—CH$_2$—CF$_2$—CF$_2$—CH$_2$—O—(C$_0$-C$_3$)-alkyl, or —(C$_0$-C$_3$)-alkylene-O—CH$_2$—(C$_1$-C$_3$)-perfluoroalkylene-CH$_2$—OH,
26) —SO$_w$—N(R$^{11}$)—R$^{13}$, wherein w is 1 or 2,
27) —(C$_0$-C$_4$)-alkylene-C(O)—N(R$^{11}$)—R$^{13}$,
28) —(C$_0$-C$_4$)-alkylene-N(R$^{11}$)—R$^{13}$, or
29) a residue selected from the group consisting of

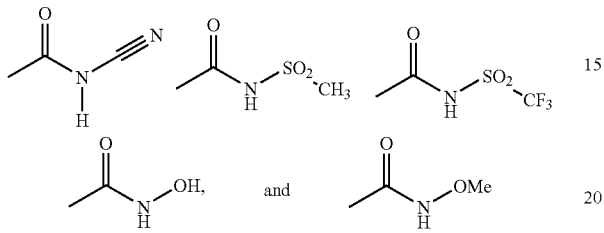

wherein Me is methyl;
R13 is fluorine, chlorine, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_0$-C$_3$)-alkylene-O—R$^{10}$, —Si—(CH$_3$)$_3$, —N(R$^{10}$)—S(O)$_2$—R$^{10}$, —S—R$^{10}$, —SO$_2$—R$^{10}$, —S(O)$_2$—N(R$^{10}$)—R$^{20}$, —C(O)—R$^{10}$, —(C$_1$-C$_8$)-alkyl, —(C$_1$-C$_8$)-alkoxy, phenyl, phenyloxy-, —O—CF$_3$, —(C$_1$-C$_3$)-perfluoroalkyl, —NH—C(O)—NH—R$^{10}$, —(C$_0$-C$_4$)-alkyl-C(O)—O—C(R15, R16)-O—C(O)—R17, —(C$_1$-C$_4$)-alkoxy-phenyl, —(C$_0$-C$_4$)-alkyl-C(O)—O—C(R15, R16)-O—C(O)—O—R17, —O—R15, —NH—C(O)—O—R$^{10}$, or a residue selected from the group consisting of

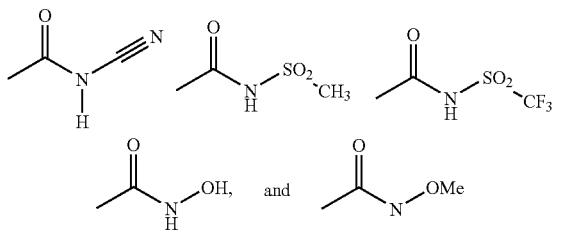

wherein Me is methyl;
R15 and R16 are independently of one another hydrogen, —(C$_1$-C$_6$)-alkyl, or together form cyclopropyl, cyclobutyl, cyclopentyl or cyclohexyl, wherein each ring is unsubstituted or substituted one to three times by R$^{10}$; and
R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_1$-C$_6$)-alkyl-O—(C$_1$-C$_8$)-alkyl-(C$_3$-C$_8$)-cycloalkyl, —(C$_0$-C$_6$)-alkyl-(C$_3$-C$_8$)-cycloalkyl, wherein the cycloalkyl is unsubstituted or substituted one, two or three times by —OH, —O—(C$_1$-C$_4$)-alkyl or R$^{10}$.
or a stereoisomer or a mixture of stereoisomers thereof in any ration, or a physiologically acceptable salt thereof.

5. The compound according to claim 1, wherein
R0 is
1) phenyl, wherein the phenyl is unsubstituted or mono-, di- or trisubstituted independently of one another by R8,
2) pyridyl, which is unsubstituted or mono-, di- or trisubstituted independently of one another by R8,
3) isoxazolyl, which is unsubstituted or mono-, di- or trisubstituted independently of one another by R8, and in addition is substituted by thienyl, 2-thienyl, or 3-thienyl, each of which is unsubstituted or mono-, di- or trisubstituted independently of one another by R8;
R8 is
1) F, Cl, Br, or I,
4) —C(O)—NH$_2$,
9) —(C$_1$-C$_4$)-alkyl, wherein the alkyl is unsubstituted or mono-, di- or trisubstituted independently of one another by halogen, —OH or methoxy, or
10) —O—(C$_1$-C$_4$)-alkyl, wherein the alkyl is unsubstituted or mono-, di- or trisubstituted independently of one another by halogen or methoxy, provided that R8 is at least one halogen, —C(O)—NH$_2$ or —O—(C$_1$-C$_8$)-alkyl residue;
substructure D is pyridyl, and is unsubstituted or substituted 1, 2, 3 or 4 times by R$^3$, or is substituted 1 or 2 times by =O;
Q is a direct bond, —C(O)—, —SO$_2$—, —(C$_1$-C$_6$)-alkylene or —(C$_0$-C$_2$)-alkylene-C(O)—NR$^{10}$—;
R$^1$ is hydrogen or —(C$_1$-C$_2$)-alkyl,
R$^2$ is a direct bond or —(C$_1$-C$_2$)-alkylene,
R14 is fluorine, chlorine, =O, —(C$_1$-C$_4$)-alkyl or —NH$_2$;
V is
2) phenyl, wherein the phenyl is unsubstituted or mono-, di- or trisubstituted independently of one another by R14, or
3) imidazole, isothiazole, oxazole, piperidine, pyridine, pyrrolidine, tetrazole, or 1,3-thiazole, each of which is unsubstituted or mono-, di- or trisubstituted independently of one another by R14;
G is a direct bond, —(CH$_2$)$_m$—, or —(CH$_2$)$_m$—NR$^{10}$—;
m is zero, 1, 2, 3 or 4;
M is
1) hydrogen,
2) —(C$_1$-C$_6$)-alkyl, wherein the alkyl is unsubstituted or mono-, di- or trisubstituted independently of one another by R14,
6) piperidine, pyridine, pyrrolidine, imidazole, oxazole, thiazole, or isothiazole, each of which is unsubstituted or mono-, di- or trisubstituted independently of one another by R14, or
7) (C$_3$-C$_6$)-cycloalkyl;
R3 is
1) hydrogen,
2) halogen,
3) —(C$_1$-C$_4$)-alkyl, wherein the alkyl is unsubstituted or mono-, di- or trisubstituted independently of one another by R13,
4) —(C$_1$-C$_3$)-perfluoroalkyl,
5) phenyl, wherein the phenyl is unsubstituted or mono-, di- or trisubstituted independently of one another by R13,
6) —(C$_0$-C$_4$)-alkylene-O—R19,
8) —CN,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —NR$^{10}$—SO$_2$—R$^{10}$, 17) —(C₀-C₂)alkylene-C(O)—O—(C₂-C₄)-alkylene-O—C(O)—(C₁-C₄)-alkyl,
18) —C(O)—O—C(R15, R16)-O—C(O)—R17,
19) —(C₀-C₂)alkylene-C(O)—O—(C₂-C₄)-alkylene-O—C(O)—(C₁-C₆)-alkyl,
20) —C(O)—O—C(R15, R16)-O—C(O)—O—R17, or
29) a residue selected from the group consisting of

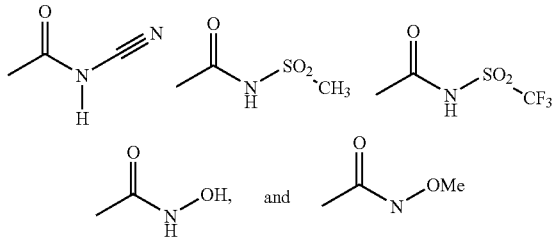

wherein Me is methyl;
R19 is
  a) hydrogen,
  b) —(C₁-C₄)-alkyl, wherein the alkyl is unsubstituted or mono-, di- or trisubstituted independently of one another by R13,
  c) —CF₃, or
  d) —CHF₂;
R11 and R12 are independently of one another identical or different and are
  1) hydrogen,
  2) —(C₁-C₄)-alkyl, wherein the alkyl is unsubstituted or mono-, di- or trisubstituted independently of one another by R13,
  3) —(C₀-C₆)-alkyl-(C₃-C₆)-cycloalkyl, or
  7) —O—R¹⁷,
R13 is fluorine, —CN, =O, —OH, —CF₃, —C(O)—O—R¹⁰, —C(O)—N(R¹⁰)—R²⁰, —N(R¹⁰)—R²⁰, —(C₃-C₆)-cycloalkyl, —(C₀-C₃)-alkylene-O—R¹⁰, —Si—(CH₃)₃, —S—R¹⁰, —SO₂—R¹⁰, —(C₁-C₃)-perfluoroalkyl, or a residue selected from the group consisting of

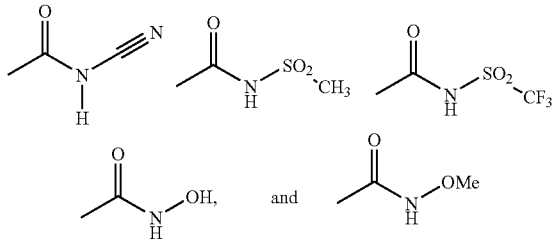

wherein Me is methyl;
R¹⁰ and R²⁰ are independently of one another hydrogen, —(C₁-C₄)-alkyl or —(C₁-C₃)-perfluoroalkyl;
R¹⁵ and R¹⁶ are independently of one another hydrogen, —(C₁-C₄)-alkyl, or together form cyclopropyl, cyclobutyl, cyclopentyl or cyclohexyl, wherein each ring is unsubstituted or substituted one to three times by R¹⁰, and
R17 is —(C₁-C₆)-alkyl, —(C₁-C₆)-alkyl-OH, —(C₁-C₆)-alkyl-O—(C₁-C₆)-alkyl, —(C₁-C₆)-alkyl-O—(C₁-C₈)-alkyl-(C₃-C₈)-cycloalkyl, —(C₀-C₆)-alkyl-(C₃-C₈)-cycloalkyl, wherein the cycloalkyl is unsubstituted or substituted one, two or three times by —OH, —O—(C₁-C₄)-alkyl or R¹⁰,
or a stereoisomer or a mixture of stereoisomers thereof in any ration, or a physiologically acceptable salt thereof.

6. The compound according to claim 1, wherein
R0 is
  1) phenyl, wherein the phenyl is unsubstituted or mono- or disubstituted independently of one another by R8,
  2) pyridyl wherein the pyridyl is unsubstituted or mono- or disubstituted independently of one another by R8, or
  3) isoxazolyl, which is substituted by thienyl, 2-thienyl or 3-thienyl, wherein the thienyl, 2-thienyl or 3-thienyl is unsubstituted or mono- or disubstituted independently of one another by R8;
R8 is F, Cl, Br, —OCH₃ or —C(O)—NH₂;
substructure D is pyridyl, and is unsubstituted or substituted 1, 2, 3 or 4 times by R3, or is substituted 1 or 2 times by =O;
Q is a direct bond, —C(O)—, —SO₂—, —CH₂—C(O)—NH—, methylene or ethylene;
R¹ is hydrogen,
R² is a direct bond or methylene,
R14 is fluorine, chlorine, =O, methyl, ethyl or —NH₂;
V is
  2) phenyl, wherein the phenyl is unsubstituted or mono- or disubstituted independently of one another by R14, or
  3) piperidine, or pyrrolidine, each of which is unsubstituted or mono- or disubstituted independently of one another by R14;
G is a direct bond, —(CH₂)ₘ—, or —(CH₂)ₘ—NR¹⁰—;
m is zero, 1 or 2;
M is
  1) hydrogen,
  2) (C₂-C₄)-alkyl, wherein the alkyl is unsubstituted or mono- or disubstituted independently of one another by R14,
  6) imidazolyl, piperidinyl, pyridyl, or pyrrolidinyl, each of which is unsubstituted or mono- or disubstituted independently of one another by R14, or
  7) cyclopropyl, cyclobutyl, cyclopentyl, or cyclohexyl, each of which is unsubstituted or mono- or disubstituted independently of one another by R14;
R3 is
  1) hydrogen,
  2) F or Cl,
  3) —(C₁-C₄)-alkyl, wherein alkyl is unsubstituted or mono-, di- or trisubstituted independently of one another by R13,
  4) —(C₁-C₃)-perfluoroalkyl,
  5) phenyl, wherein the phenyl is unsubstituted or mono-, di- or trisubstituted independently of one another by R13,
  6) —(C₀-C₂)-alkylene-O—R19,
  8) —CN,
  9) —SOₛ—R¹¹, wherein s is 1 or 2,
  10) —SOₜ—N(R¹¹)—R¹², wherein t is 1 or 2,
  11) —(C₀-C₄)-alkylene-C(O)—R¹¹,
  12) —(C₀-C₄)-alkylene-C(O)—O—R¹¹,
  13) —(C₀-C₄)-alkylene-C(O)—N(R¹¹)—R¹²,
  14) —(C₀-C₄)-alkylene-N(R¹¹)—R¹²,
  15) —NR¹⁰—SO₂—R¹⁰,
  17) —(C₀-C₂)alkylene-C(O)—O—(C₂-C₄)-alkylene-O—C(O)—(C₁-C₄)-alkyl, 18) —C(O)—O—C(R15, R16)-O—C(O)—R17,
19) —(C$_0$-C$_2$)alkylene-C(O)—O—(C$_2$-C$_4$)-alkylene-O—C(O)—O—(C$_1$-C$_6$)-alkyl or
20) —C(O)—O—C(R15, R16)-O—C(O)—O—R17;

R11 and R12 are independently of one another identical or different and are
1) hydrogen,
2) —(C$_1$-C$_4$)-alkyl, wherein the alkyl is unsubstituted or mono-, di- or trisubstituted independently of one another by R13,
3) —(C$_0$-C$_6$)-alkyl-(C$_3$-C$_6$)-cycloalkyl, or
7) —O—R$^{17}$, R13 is fluorine, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_6$)-cycloalkyl, —(C$_0$-C$_3$)-alkylene-O—R$^{10}$, —Si—(CH$_3$)$_3$, —S—R$^{10}$, —SO$_2$—R$^{10}$, or —(C$_1$-C$_3$)-perfluoroalkyl;

R$^{10}$ and R$^{20}$ are independently of one another hydrogen, —(C$_1$-C$_4$)-alkyl or —(C$_1$-C$_3$)-perfluoroalkyl;

R$^{15}$ and R$^{16}$ are independently of one another hydrogen, —(C$_1$-C$_4$)-alkyl, or together form cyclopropyl, cyclobutyl, cyclopentyl or cyclohexyl, wherein each ring is unsubstituted or substituted one to three times by R$^{10}$; and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_1$-C$_6$)-alkyl-O—(C$_1$-C$_8$)-alkyl-(C$_3$-C$_8$)-cycloalkyl, —(C$_0$-C$_6$)-alkyl-(C$_3$-C$_8$)-cycloalkyl, wherein the cycloalkyl is unsubstituted or substituted one, two or three times by —OH, —O—(C$_1$-C$_4$)-alkyl or R$^{10}$, or a stereoisomer or a mixture of stereoisomers thereof in any ration, or a physiologically acceptable salt thereof.

7. The compound according to claim 1, wherein
R0 is
2) pyridyl wherein the pyridyl is unsubstituted or mono- or disubstituted independently of one another by R8, or
3) isoxazolyl which is substituted by thienyl, 2-thienyl and 3-thienyl, wherein the thienyl, 2-thienyl or 3-thienyl is unsubstituted or mono- or disubstituted independently of one another by R8;

R8 is F, Cl, Br, —OCH$_3$ or —C(O)—NH$_2$;
substructure D is pyridyl and is unsubstituted or substituted 1, 2, 3 or 4 times by R3, or is substituted 1 or 2 times by =O;
Q is —CH$_2$—C(O)—NH— or methylene;
R$^1$ is hydrogen atom;
R$^2$ is a direct bond;
R14 is fluorine, chlorine, =O, methyl, ethyl or —NH$_2$;
V is piperidine, wherein the piperidine is unsubstituted or mono- or disubstituted independently of one another by R14;
G is a direct bond;
M is hydrogen, (C$_2$-C$_4$)-alkyl, or pyridyl, wherein the alkyl or pyridyl is unsubstituted or mono- or disubstituted independently of one another by R14;
R3 is
1) hydrogen,
2) fluorine, or chlorine,
3) —(C$_1$-C$_4$)-alkyl, wherein the alkyl is unsubstituted or mono-, di- or trisubstituted independently of one another by R13,
6) —(C$_0$-C$_2$)-alkylene-O—R19,
12) —(C$_0$-C$_4$)-alkylene-C(O)—O—R$^{11}$ or
13) —(C$_0$-C$_4$)-alkylene-C(O)—N(R$^{11}$)—R$^{12}$;

R19 is
a) hydrogen or
b) —(C$_1$-C$_4$)-alkyl, wherein the alkyl is unsubstituted or mono-, di- or trisubstituted independently of one another by R13;

R11 and R12 are independently of one another identical or different and are
1) hydrogen, or
2) —(C$_1$-C$_4$)-alkyl, wherein the alkyl is unsubstituted or mono-, di- or trisubstituted independently of one another by R13, R13 is fluorine, =O, —OH, —CF$_3$, —C(O)—O—R$^{10}$, —C(O)—N(R$^{10}$)—R$^{20}$, —N(R$^{10}$)—R$^{20}$, or —(C$_0$-C$_3$)-alkylene-O—R$^{10}$; and R$^{10}$ and R$^{20}$ are independently of one another hydrogen, —(C$_1$-C$_4$)-alkyl or —(C$_1$-C$_3$)-perfluoroalkyl, or a stereoisomer or a mixture of stereoisomers thereof in any ration, or a physiologically acceptable salt thereof.

8. The compound according to claim 1, wherein the compound is
1-[5-(5-Chloro-thiophen-2-yl)-isoxazol-3-ylmethyl]-1H-pyrrolo[2,3-b]pyridine-2-carboxylic acid (1-isopropyl-piperidin-4-yl)-amide,
1-[5-(5-Chloro-thiophen-2-yl)-isoxazol-3-ylmethyl]-2-(1-isopropyl-piperidin-4-ylcarbamoyl)-1H-pyrrolo[2,3-b]pyridine-5-carboxylic acid methyl ester,
1-[5-(5-Chloro-thiophen-2-yl)-isoxazol-3-ylmethyl]-2-(1-isopropyl-piperidin-4-ylcarbamoyl)-1H-pyrrolo[2,3-b]pyridine-5-carboxylic acid,
1-[5-(5-Chloro-thiophen-2-yl)-isoxazol-3-ylmethyl]-1H-pyrrolo[2,3-b]pyridine-2,5-dicarboxylic acid 5-amide 2-[(1-isopropyl-piperidin-4-yl)-amide],
1-[5-(5-Chloro-thiophen-2-yl)-isoxazol-3-ylmethyl]-1H-pyrrolo[3,2-b]pyridine-2-carboxylic acid (1-isopropyl-piperidin-4-yl)-amide,
1-[5-(5-Chloro-thiophen-2-yl)-isoxazol-3-ylmethyl]-2-(1-isopropyl-piperidin-4-ylcarbamoyl)-1H-pyrrolo[3,2-b]pyridine-5-carboxylic acid,
1-[5-(5-Chloro-thiophen-2-yl)-isoxazol-3-ylmethyl]-5-oxo-4,5-dihydro-1H-pyrrolo[3,2-b]pyridine-2-carboxylic acid (1-isopropyl-piperidin-4-yl)-amide,
1-[5-(5-Chloro-thiophen-2-yl)-isoxazol-3-ylmethyl]-2-(3,4,5,6-tetrahydro-2H-[1,4']bipyridinyl-4-ylcarbamoyl)-1H-pyrrolo[3,2-b]pyridine-5-carboxylic acid methyl ester,
1-[5-(5-Chloro-thiophen-2-yl)-isoxazol-3-ylmethyl]-2-(3,4,5,6-tetrahydro-2H-[1,4']bipyridinyl-4-ylcarbamoyl)-1H-pyrrolo[3,2-b]pyridine-5-carboxylic acid,
1-[5-(5-Chloro-thiophen-2-yl)-isoxazol-3-ylmethyl]-5-(2-methoxy-ethoxy)-1H-pyrrolo[2,3-c]pyridine-2-carboxylic acid (1-isopropyl-piperidin-4-yl)-amide,
1-[5-(5-Chloro-thiophen-2-yl)-isoxazol-3-ylmethyl]-5-(2-hydroxy-ethoxy)-1H-pyrrolo[2,3-c]pyridine-2-carboxylic acid (1-isopropyl-piperidin-4-yl)-amide,
1-[(5-Chloro-pyridin-2-ylcarbamoyl)-methyl]-5-(2-methoxy-ethoxy)-1H-pyrrolo[2,3-c]pyridine-2-carboxylic acid (1-isopropyl-piperidin-4-yl)-amide,
1-[(5-Chloro-pyridin-2-ylcarbamoyl)-methyl]-5-(2-hydroxy-ethoxy)-1H-pyrrolo[2,3-c]pyridine-2-carboxylic acid (1-isopropyl-piperidin-4-yl)-amide,
1-(6-Chloro-benzo[b]thiophen-2-ylmethyl)-5-(2-methoxy-ethoxy)-1H-pyrrolo[2,3-c]pyridine-2-carboxylic acid (1-isopropyl-piperidin-4-yl)-amide or
1-(6-Chloro-benzo[b]thiophen-2-ylmethyl)-5-(2-hydroxy-ethoxy)-1H-pyrrolo[2,3-c]pyridine-2-carboxylic acid (1-isopropyl-piperidin-4-yl)-amide.

or a stereoisomer or a mixture of stereoisomers thereof in any ration, or a physiologically acceptable salt thereof.

9. A process for the preparation of a compound according to claim 1, which comprises condensing a compound of formula 29 with a compound of the formula HR$^{8'}$ to give a compound of formula 30 and converting the compound of the formula 30 into a compound of the formula I,

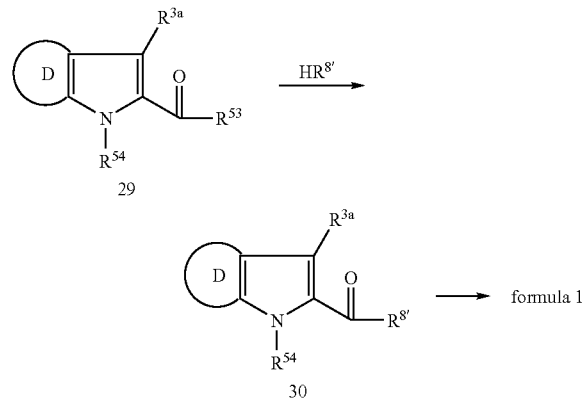

wherein the residue R$^{8t}$ has the donation of —N(R$^1$)—R$^2$—V-G-M as indicated claim 1, but where in R$^{8t}$ functional groups can also be present in the form of groups that are subsequently transformed into the final functional groups present in —N(R$^1$)—R$^2$—V-G-M, and where the residue R$^{54}$ denotes the group -Q-R$^o$ or can denote a group which is subsequently transformed into the group -Q-R$^o$, and where the group —C(O)—R$^{53}$ can be a carboxylic acid group or derivatives thereof, and where the groups R$^{3a}$ in the formulae 29 and 30 have the corresponding definitions of R$^3$ in formula I as defined in claim 1 or functional groups in them can also be present in protected form or in the form of precursor groups.

10. A pharmaceutical composition, comprising at least one compound according to claim 1 or a stereoisomer or a mixture of stereoisomers thereof in any ratio, or a physiologically acceptable salt thereof, and a pharmaceutically acceptable carrier.

* * * * *